(12) United States Patent
Kovacs

(10) Patent No.: US 10,923,217 B2
(45) Date of Patent: Feb. 16, 2021

(54) CONDITION OR TREATMENT ASSESSMENT METHODS AND PLATFORM APPARATUSES

(71) Applicant: Physiowave, Inc., Santa Clara, CA (US)

(72) Inventor: Gregory T. Kovacs, Palo Alto, CA (US)

(73) Assignee: Physiowave, Inc., Menlo Park, CA (US)

( * ) Notice: Subject to any disclaimer, the term of this patent is extended or adjusted under 35 U.S.C. 154(b) by 1089 days.

(21) Appl. No.: 15/354,959

(22) Filed: Nov. 17, 2016

(65) Prior Publication Data

US 2017/0147754 A1    May 25, 2017

Related U.S. Application Data

(63) Continuation of application No. PCT/US2016/062484, filed on Nov. 17, 2016, and a
(Continued)

(51) Int. Cl.
| | |
|---|---|
| *G16H 10/60* | (2018.01) |
| *G06F 19/00* | (2018.01) |
| *A61B 5/00* | (2006.01) |
| *A61B 5/0402* | (2006.01) |
| *A61B 5/024* | (2006.01) |

(Continued)

(52) U.S. Cl.
CPC ............ *G16H 10/60* (2018.01); *A61B 5/024* (2013.01); *A61B 5/02007* (2013.01); *A61B 5/0402* (2013.01); *A61B 5/0537* (2013.01); *A61B 5/1102* (2013.01); *A61B 5/6887* (2013.01); *G01G 19/50* (2013.01); *G06F 19/326* (2013.01); *G06F 19/3456* (2013.01); *A61B 5/02055* (2013.01); *A61B 5/02125* (2013.01);
(Continued)

(58) Field of Classification Search
CPC . A61B 5/0205; A61B 5/0402; A61B 5/04023; A61B 5/053; A61B 5/0535; A61B 5/0537; A61B 5/6887; G01G 19/50; G01G 19/44; G01G 23/18; G01G 23/3728; G01G 23/3735
See application file for complete search history.

(56) References Cited

U.S. PATENT DOCUMENTS

| | | |
|---|---|---|
| 3,702,113 A | 11/1972 | Blockley et al. |
| 4,195,643 A | 4/1980 | Pratt, Jr. |

(Continued)

*Primary Examiner* — Tammie K Marlen
(74) *Attorney, Agent, or Firm* — Crawford Maunu PLLC

(57) ABSTRACT

Certain aspects of the disclosure are directed to an apparatus including a scale. The scale includes a platform in which a plurality of electrodes are integrated and configured and arranged for engaging a user and processing circuitry. The processing circuitry is electrically integrated with the plurality of electrodes to process user-corresponding data with physiologic parameter data obtained while the user is standing on the platform and therefrom derive and output derivation data indicative of a physiologic status of the user for assessment of a condition or treatment of the user that corresponds with the physiologic status, and store, in response to the derived derivation data, additional data in the memory circuit to supplement the user-corresponding data with information corresponding to the physiologic parameter data obtained while the user is standing on the platform.

20 Claims, 33 Drawing Sheets

Related U.S. Application Data continuation of application No. PCT/US2016/062505, filed on Nov. 17, 2016.

(60) Provisional application No. 62/266,523, filed on Dec. 11, 2015, provisional application No. 62/258,238, filed on Nov. 20, 2015, provisional application No. 62/258,253, filed on Nov. 20, 2015.

(51) Int. Cl.
*A61B 5/11* (2006.01)
*A61B 5/02* (2006.01)
*G01G 19/50* (2006.01)
*A61B 5/0537* (2021.01)
*A61B 5/0535* (2021.01)
*A61B 5/0205* (2006.01)
*A61B 5/021* (2006.01)

(52) U.S. Cl.
CPC ........... *A61B 5/0535* (2013.01); *A61B 5/7225* (2013.01); *A61B 2562/046* (2013.01)

(56) References Cited

U.S. PATENT DOCUMENTS

| | | | |
|---|---|---|---|
| 4,362,164 A | 12/1982 | Little et al. |
| 4,557,271 A | 12/1985 | Stoller et al. |
| 4,657,025 A | 4/1987 | Orlando |
| 4,679,569 A | 7/1987 | Lee |
| 4,765,321 A | 8/1988 | Mohri |
| 4,836,215 A | 6/1989 | Lee |
| 4,898,182 A | 2/1990 | Hawkins et al. |
| 4,947,857 A | 8/1990 | Albert et al. |
| 4,958,638 A | 9/1990 | Sharpe et al. |
| 5,314,389 A | 5/1994 | Dotan |
| 5,431,170 A | 7/1995 | Mathews |
| 5,620,003 A | 4/1997 | Sepponen |
| 5,678,562 A | 10/1997 | Sellers |
| 5,682,902 A | 11/1997 | Herleikson |
| 5,701,894 A | 12/1997 | Cherry et al. |
| 5,750,937 A | 5/1998 | Johnson et al. |
| 5,782,238 A | 7/1998 | Beitler |
| 5,833,623 A | 11/1998 | Mann et al. |
| 6,047,203 A | 4/2000 | Sackner et al. |
| 6,080,110 A | 6/2000 | Thorgersen |
| 6,168,563 B1 | 1/2001 | Brown |
| 6,198,394 B1 | 3/2001 | Jacobsen et al. |
| 6,205,547 B1 | 3/2001 | Davis |
| 6,228,033 B1 | 5/2001 | Koobi et al. |
| 6,292,690 B1 | 9/2001 | Petrucelli |
| 6,331,162 B1 | 12/2001 | Mitchell |
| 6,454,708 B1 | 9/2002 | Ferguson et al. |
| 6,454,719 B1 | 9/2002 | Greenhut |
| 6,516,221 B1 | 2/2003 | Hirouchi et al. |
| 6,551,252 B2 | 4/2003 | Sackner et al. |
| 6,594,759 B1 | 7/2003 | Wang |
| 6,640,134 B2 | 10/2003 | Raymond et al. |
| 6,685,634 B1 | 2/2004 | Fry |
| 6,702,754 B2 | 3/2004 | Ogura et al. |
| 6,705,990 B1 | 3/2004 | Gallant |
| 6,734,856 B2 | 5/2004 | Ishikawa et al. |
| 6,755,783 B2 | 6/2004 | Cosentino et al. |
| 6,783,498 B2 | 8/2004 | Sackner et al. |
| 6,790,178 B1 | 9/2004 | Mault et al. |
| 6,814,705 B2 | 11/2004 | Kawaguchi |
| 6,847,892 B2 | 1/2005 | Zhou et al. |
| 6,875,174 B2 | 4/2005 | Braun et al. |
| 6,898,299 B1 | 5/2005 | Brooks |
| 6,962,566 B2 | 11/2005 | Quistgaard et al. |
| 6,963,035 B2 | 11/2005 | Honda et al. |
| 7,137,955 B2 | 11/2006 | Bartels et al. |
| 7,257,438 B2 | 8/2007 | Kinast |
| 7,313,435 B2 | 12/2007 | Nakada et al. |
| 7,316,648 B2 | 1/2008 | Kelly et al. |
| 7,336,266 B2 | 2/2008 | Hayward et al. |
| 7,382,247 B2 | 6/2008 | Welch et al. |
| 7,384,410 B2 | 6/2008 | Eggers et al. |
| 7,417,536 B2 | 8/2008 | Lakshmanan et al. |
| 7,459,644 B2 | 12/2008 | Kenmochi |
| 7,502,643 B2 | 3/2009 | Farringdon et al. |
| 7,593,632 B2 | 9/2009 | Schnell |
| 7,668,588 B2 | 2/2010 | Kovacs |
| 7,787,946 B2 | 8/2010 | Stahmann et al. |
| 7,796,013 B2 | 9/2010 | Murakami et al. |
| 7,846,104 B2 | 12/2010 | MacQuarrie et al. |
| 7,899,522 B1 | 3/2011 | Koh et al. |
| 8,200,320 B2 | 6/2012 | Kovacs |
| 8,332,026 B2 | 12/2012 | Cha et al. |
| 8,369,936 B2 | 2/2013 | Farringdon et al. |
| 8,452,390 B2 | 5/2013 | Jensen |
| 8,473,041 B2 | 6/2013 | Bartnik et al. |
| 8,475,367 B1 | 7/2013 | Yuen et al. |
| 8,475,368 B2 | 7/2013 | Tran et al. |
| 8,529,409 B1 | 9/2013 | Lesea-Ames |
| 8,548,556 B2 | 10/2013 | Jensen |
| 8,639,226 B2 | 1/2014 | Hutchings et al. |
| 8,682,424 B2 | 3/2014 | Tsoglin et al. |
| 8,698,014 B1 | 4/2014 | Walstad |
| 8,858,449 B2 | 10/2014 | Inan et al. |
| 8,870,780 B2 | 10/2014 | Inan et al. |
| 9,011,346 B2 | 4/2015 | Wiard et al. |
| 9,055,871 B2 | 6/2015 | Inan et al. |
| 9,215,991 B2 | 12/2015 | Inan et al. |
| 9,241,637 B2 | 1/2016 | Wiard et al. |
| 2001/0030546 A1 | 10/2001 | Yamada et al. |
| 2001/0044588 A1 | 11/2001 | Mault |
| 2002/0002326 A1 | 1/2002 | Causey, III et al. |
| 2002/0062090 A1 | 5/2002 | Chai et al. |
| 2002/0188205 A1 | 12/2002 | Mills |
| 2003/0050537 A1 | 3/2003 | Wessel |
| 2003/0088196 A1 | 5/2003 | Steve |
| 2003/0126593 A1 | 7/2003 | Mault |
| 2003/0130567 A1 | 7/2003 | Mault et al. |
| 2003/0130595 A1 | 7/2003 | Mault |
| 2003/0149349 A1 | 8/2003 | Jensen |
| 2003/0197614 A1 | 10/2003 | Smith et al. |
| 2003/0233034 A1 | 12/2003 | Varri et al. |
| 2004/0068379 A1 | 4/2004 | Morgan et al. |
| 2004/0073127 A1 | 4/2004 | Istvan et al. |
| 2004/0097802 A1 | 5/2004 | Cohen |
| 2004/0138517 A1 | 7/2004 | Osorio et al. |
| 2004/0211599 A1 | 10/2004 | Kasinoff |
| 2004/0249258 A1 | 12/2004 | Tupin, Jr. et al. |
| 2005/0004483 A1 | 1/2005 | Lin |
| 2005/0017602 A1 | 1/2005 | Arms et al. |
| 2005/0033124 A1 | 2/2005 | Kelly et al. |
| 2005/0043645 A1 | 2/2005 | Ono et al. |
| 2005/0113703 A1 | 5/2005 | Farringdon et al. |
| 2005/0119711 A1 | 6/2005 | Cho et al. |
| 2005/0171451 A1 | 8/2005 | Yeo et al. |
| 2005/0203349 A1 | 9/2005 | Nanikashvili |
| 2005/0206518 A1 | 9/2005 | Welch et al. |
| 2005/0215868 A1 | 9/2005 | Kenjou et al. |
| 2005/0247494 A1 | 11/2005 | Montagnino |
| 2005/0283198 A1 | 12/2005 | Haubrich et al. |
| 2006/0049955 A1 | 3/2006 | Blum et al. |
| 2006/0079942 A1 | 4/2006 | Deno et al. |
| 2006/0106646 A1 | 5/2006 | Squilla et al. |
| 2006/0111641 A1 | 5/2006 | Manera et al. |
| 2006/0116589 A1 | 6/2006 | Park |
| 2006/0122525 A1 | 6/2006 | Shusterman |
| 2006/0149139 A1 | 7/2006 | Bonmassar et al. |
| 2006/0154642 A1 | 7/2006 | Scannell |
| 2006/0155589 A1 | 7/2006 | Lane et al. |
| 2007/0055324 A1 | 3/2007 | Thompson et al. |
| 2007/0069887 A1 | 3/2007 | Welch et al. |
| 2007/0161913 A1 | 7/2007 | Farrell et al. |
| 2007/0167286 A1 | 7/2007 | Roes |
| 2007/0197878 A1 | 8/2007 | Shklarski |
| 2007/0208232 A1 | 9/2007 | Kovacs |
| 2007/0208233 A1 | 9/2007 | Kovacs |
| 2007/0287928 A1 | 12/2007 | Kiviniemi et al. |
| 2007/0293770 A1 | 12/2007 | Bour et al. |
| 2008/0027679 A1 | 1/2008 | Shklarski |

(56) References Cited

U.S. PATENT DOCUMENTS

| | | |
|---|---|---|
| 2008/0073128 A1 | 3/2008 | Umemoto |
| 2008/0154645 A1 | 6/2008 | Takehara |
| 2008/0161700 A1 | 7/2008 | Sachanandani et al. |
| 2008/0183090 A1 | 7/2008 | Farringdon et al. |
| 2008/0194975 A1 | 8/2008 | MacQuarrie et al. |
| 2008/0208009 A1 | 8/2008 | Shklarski |
| 2008/0221404 A1 | 9/2008 | Tso |
| 2008/0246629 A1 | 10/2008 | Tsui et al. |
| 2008/0281222 A1 | 11/2008 | Fukada |
| 2008/0306393 A1 | 12/2008 | Ting et al. |
| 2009/0016582 A1 | 1/2009 | Penn et al. |
| 2009/0024044 A1 | 1/2009 | Virtanen et al. |
| 2009/0102296 A1 | 4/2009 | Greene et al. |
| 2009/0182204 A1 | 7/2009 | Semler et al. |
| 2009/0203972 A1 | 8/2009 | Heneghan et al. |
| 2009/0240194 A1 | 9/2009 | Keimel et al. |
| 2009/0284496 A1 | 11/2009 | Oki |
| 2009/0287933 A1 | 11/2009 | Beckwith et al. |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 | 4/2010 | Inan et al. |
| 2010/0174205 A1 | 7/2010 | Wegerif |
| 2010/0210921 A1 | 8/2010 | Park et al. |
| 2010/0262044 A1 | 10/2010 | Siegler |
| 2011/0040352 A1 | 2/2011 | Gerber et al. |
| 2011/0054359 A1 | 3/2011 | Sazonov et al. |
| 2011/0080181 A1 | 4/2011 | Sato et al. |
| 2011/0152695 A1 | 6/2011 | Granqvist et al. |
| 2011/0240379 A1 | 10/2011 | Forshaw et al. |
| 2011/0245710 A1 | 10/2011 | Jensen |
| 2011/0310005 A1 | 12/2011 | Chen |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1 | 6/2012 | Rodriguez et al. |
| 2012/0245476 A1 | 9/2012 | Skeri et al. |
| 2012/0266250 A1 | 10/2012 | Uhl |
| 2012/0283587 A1 | 11/2012 | Gosh et al. |
| 2012/0302843 A1 | 11/2012 | Otsubo et al. |
| 2012/0318869 A1 | 12/2012 | Edmonds |
| 2013/0006669 A1 | 1/2013 | Nakamura |
| 2013/0056285 A1 | 3/2013 | Meagher |
| 2013/0113506 A1 | 5/2013 | Poupyrev et al. |
| 2013/0226601 A1 | 8/2013 | Razmi et al. |
| 2013/0289889 A1 | 10/2013 | Yuen et al. |
| 2013/0310700 A1 | 11/2013 | Wiard et al. |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1 | 5/2014 | Ricks et al. |
| 2014/0142437 A1 | 5/2014 | Inan et al. |
| 2014/0172314 A1 | 6/2014 | Baarman et al. |
| 2014/0182952 A1 | 7/2014 | Yuen et al. |
| 2014/0221849 A1 | 8/2014 | Farringdon et al. |
| 2014/0221850 A1 | 8/2014 | Farringdon et al. |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0193497 A1 | 7/2015 | Tallamy et al. |
| 2015/0201844 A1 | 7/2015 | Nakagawa |
| 2015/0289802 A1 | 10/2015 | Thomas et al. |
| 2015/0331491 A1 | 11/2015 | Rumreich |
| 2015/0335291 A1 | 11/2015 | Saadi et al. |
| 2015/0338265 A1 | 11/2015 | Carreel et al. |
| 2016/0029905 A1 | 2/2016 | Kovacs |
| 2016/0116326 A1 | 4/2016 | Sharma |
| 2016/0317043 A1 | 11/2016 | Campo et al. |

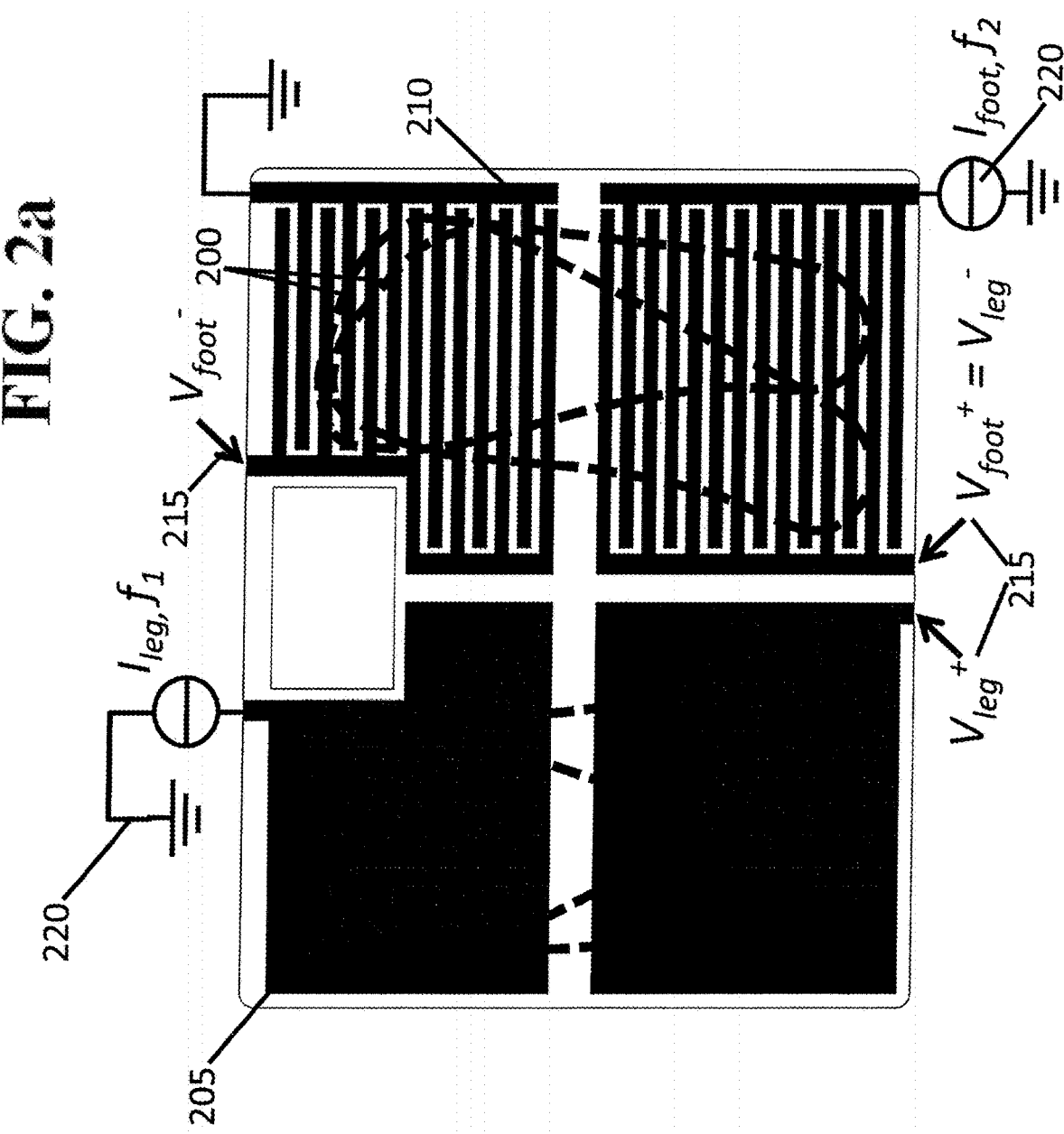

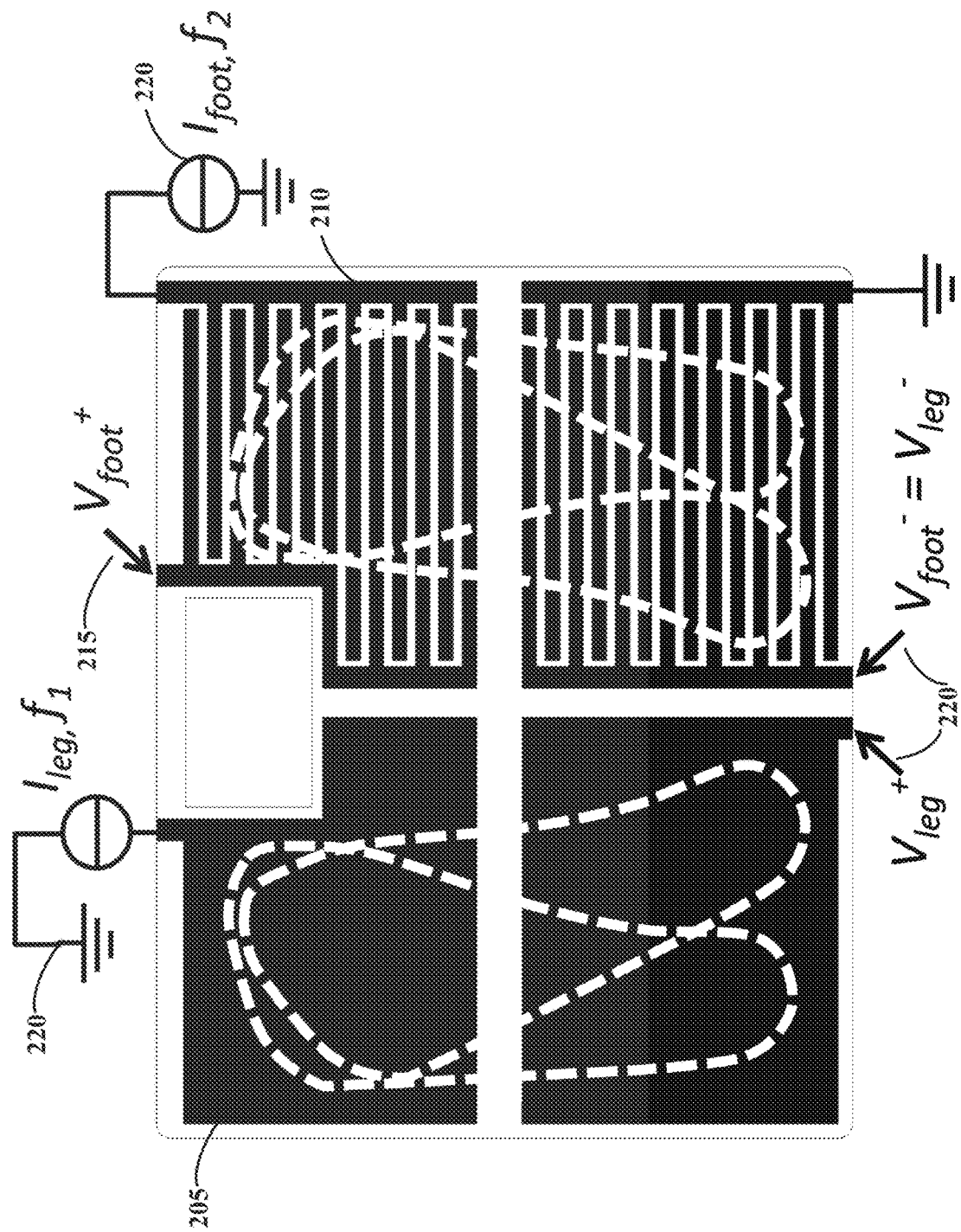

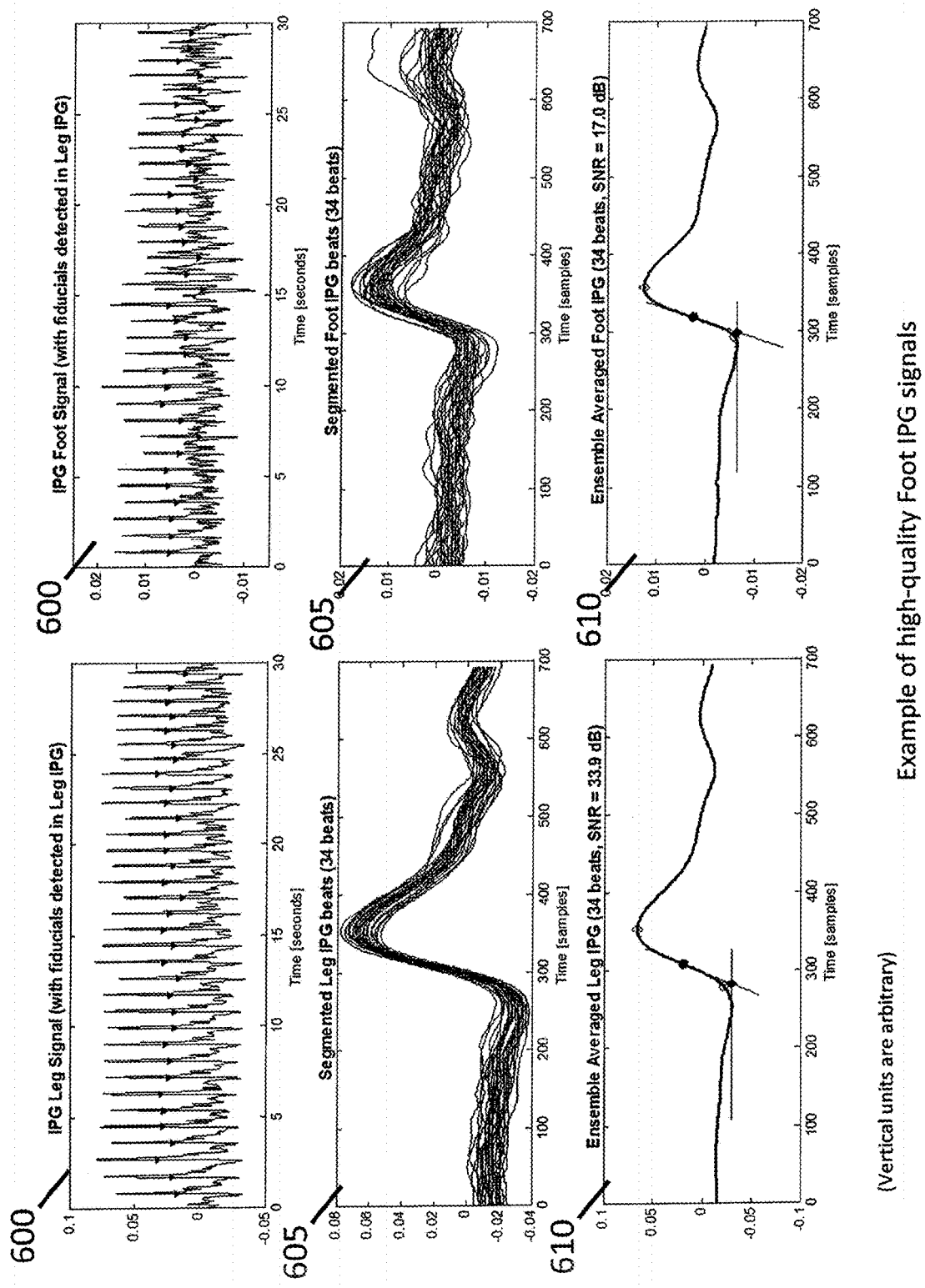

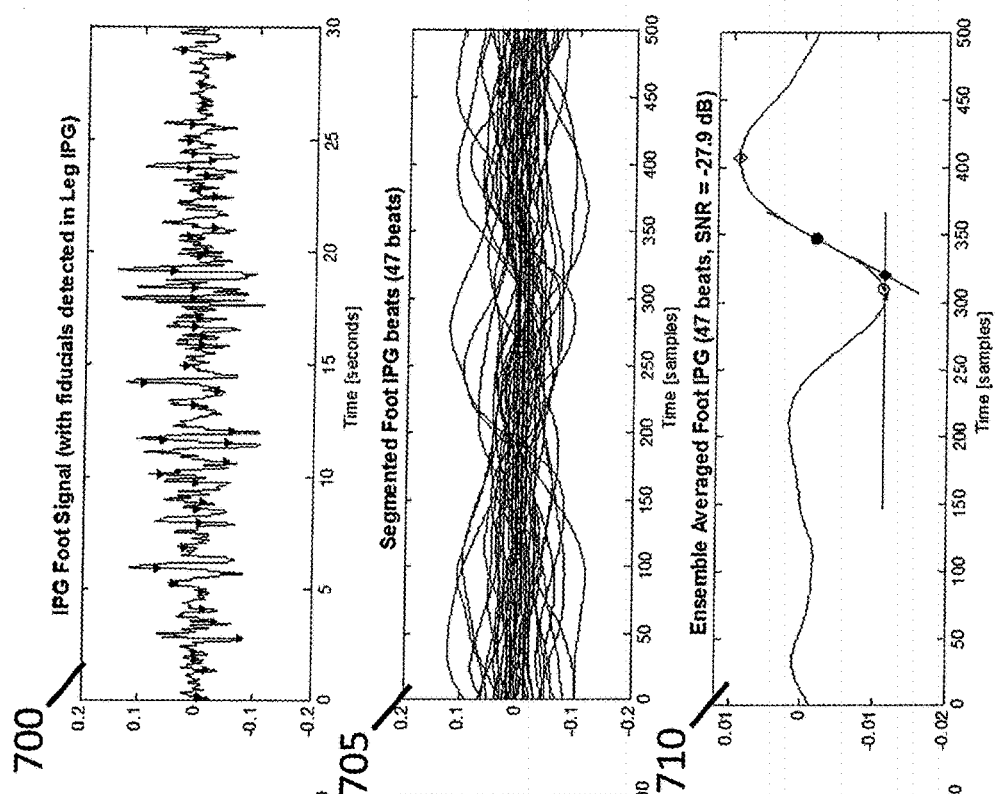
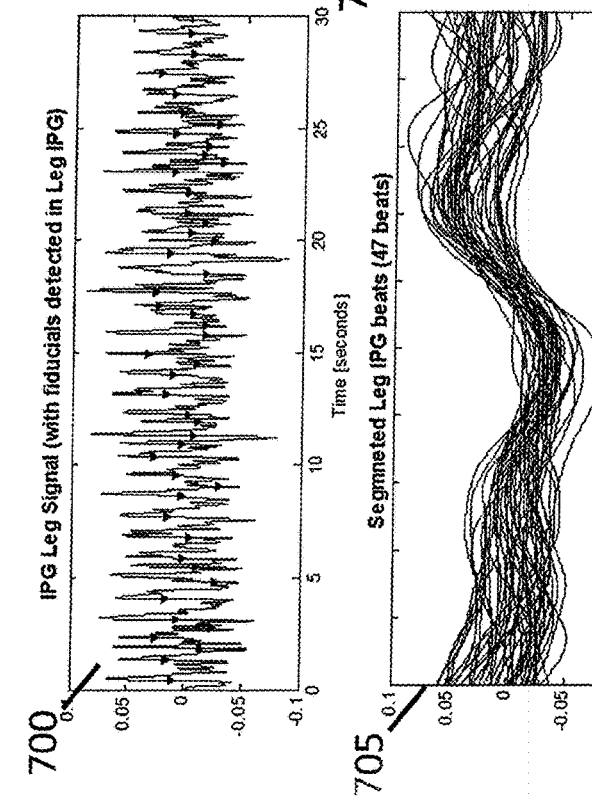
FIG.7a  Example of low-quality Foot IPG signals
FIG.7b
(Vertical units are arbitrary)

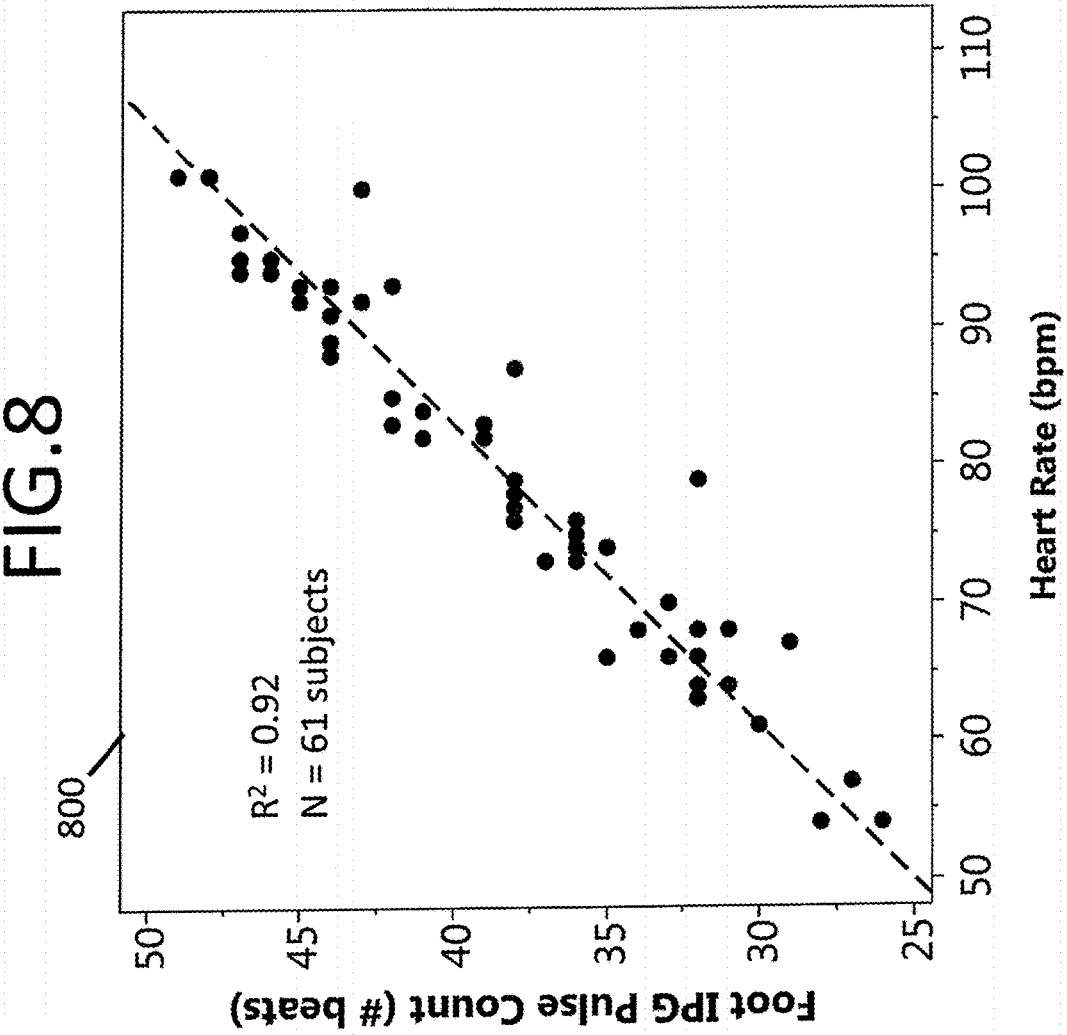

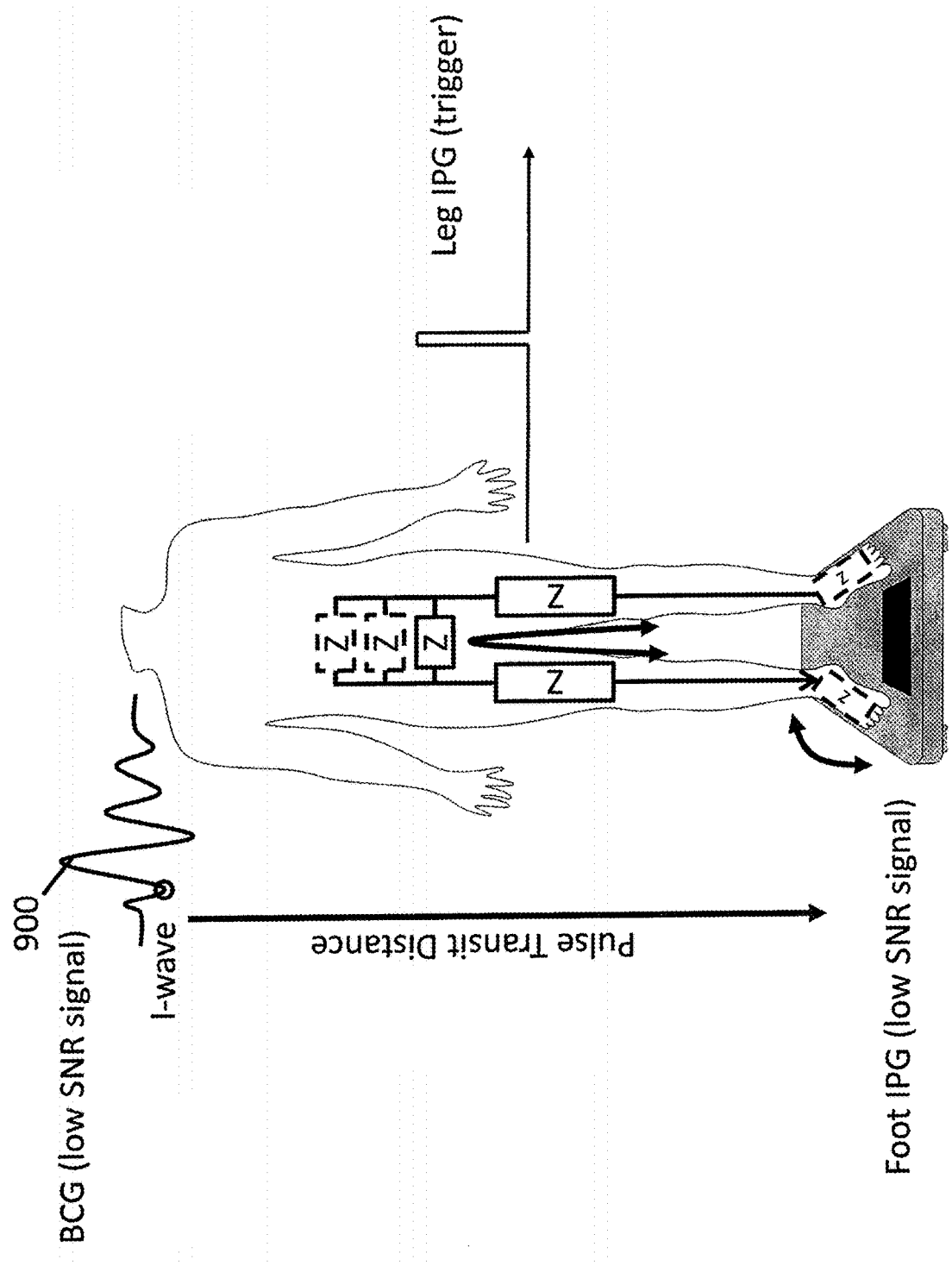

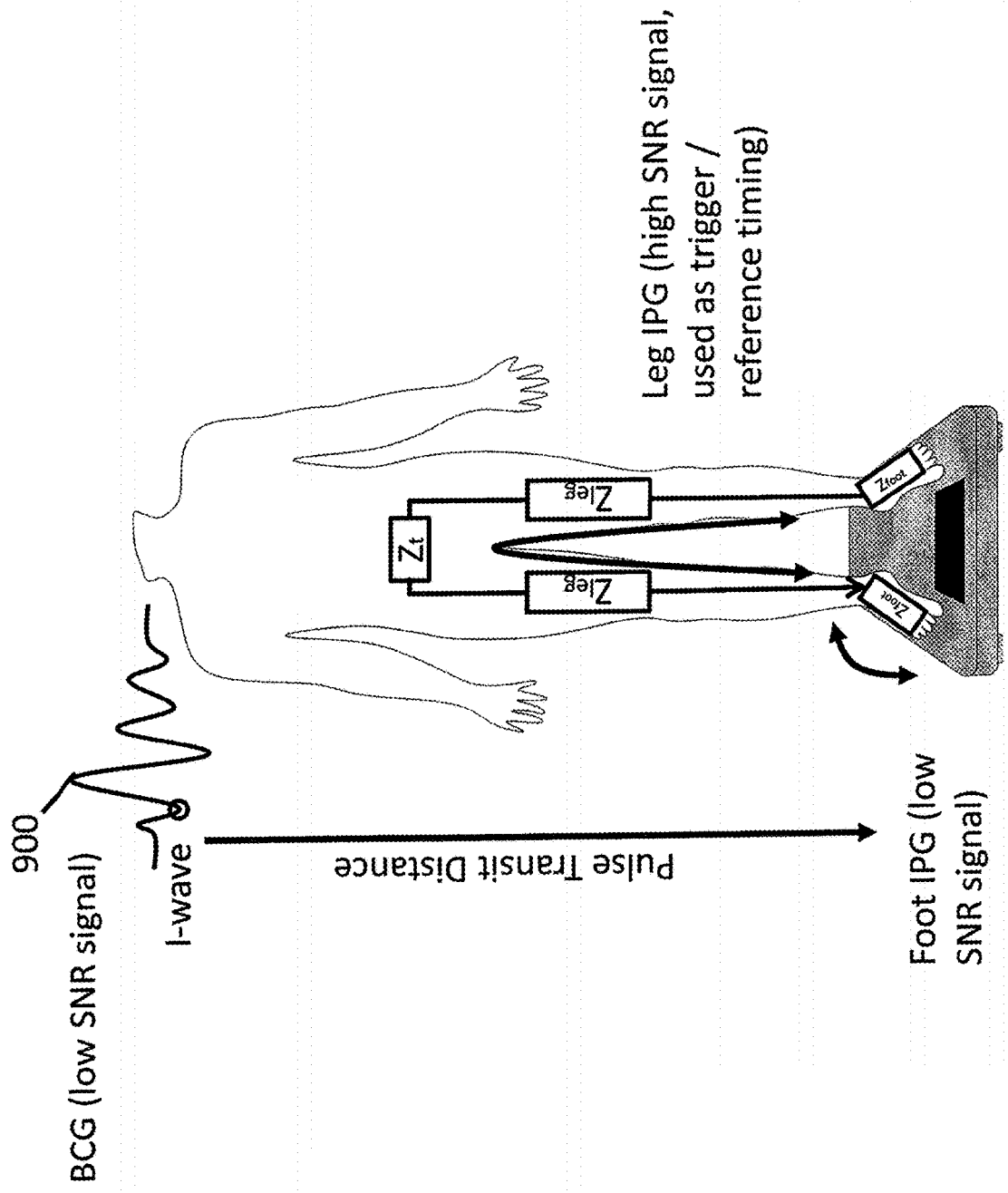

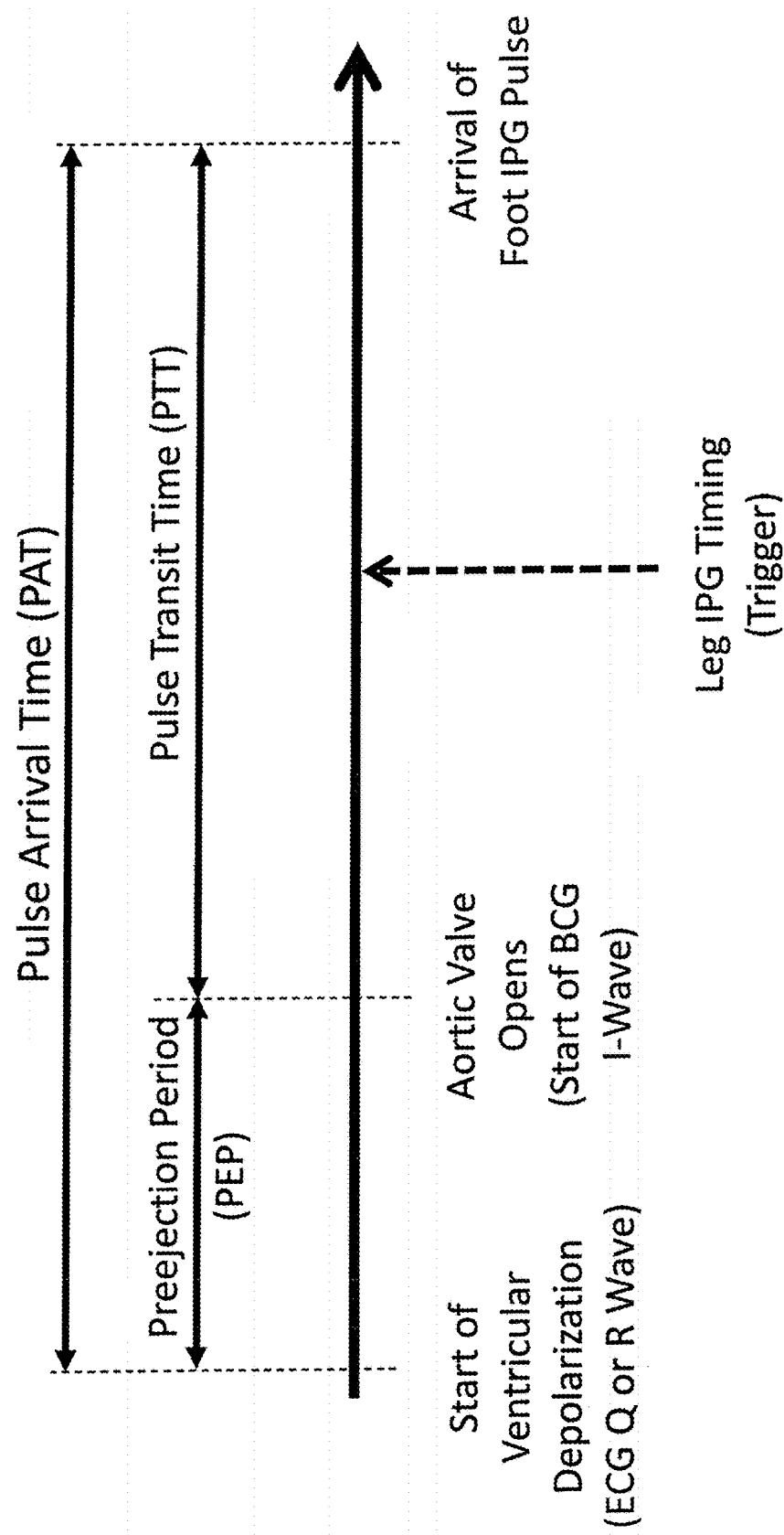

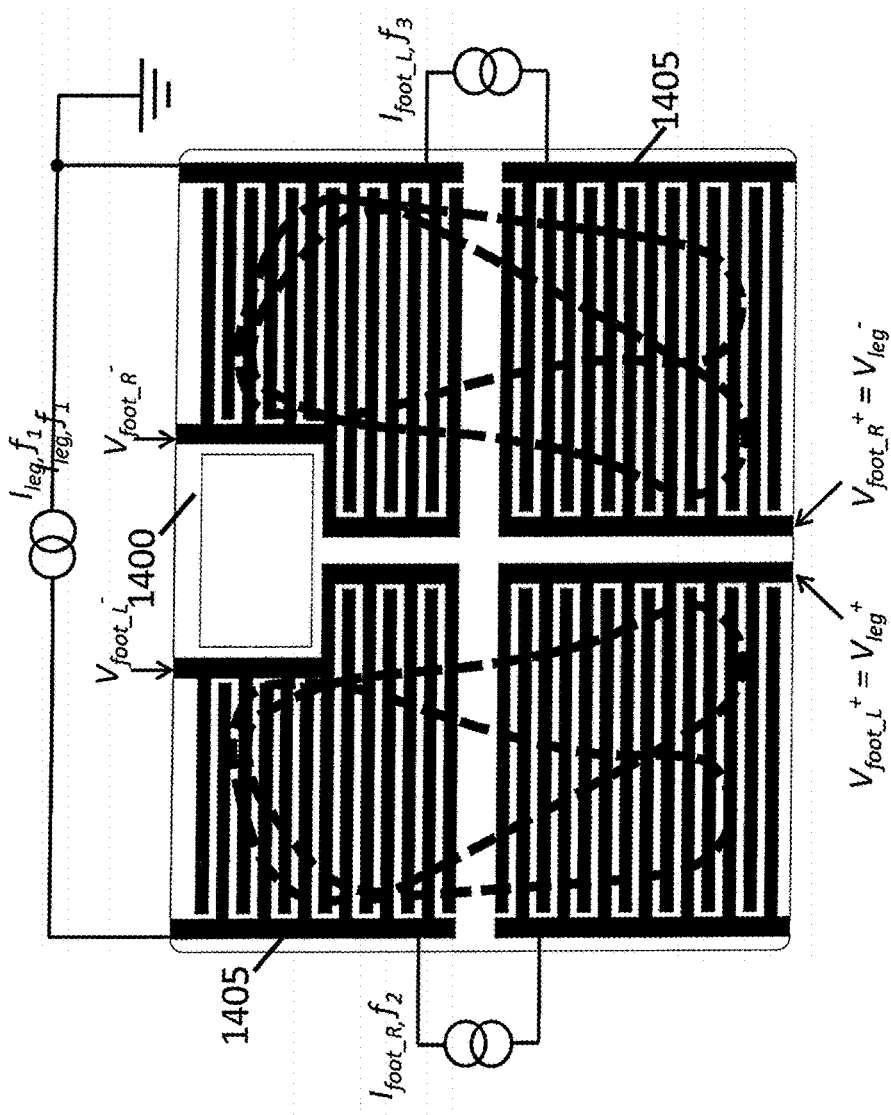

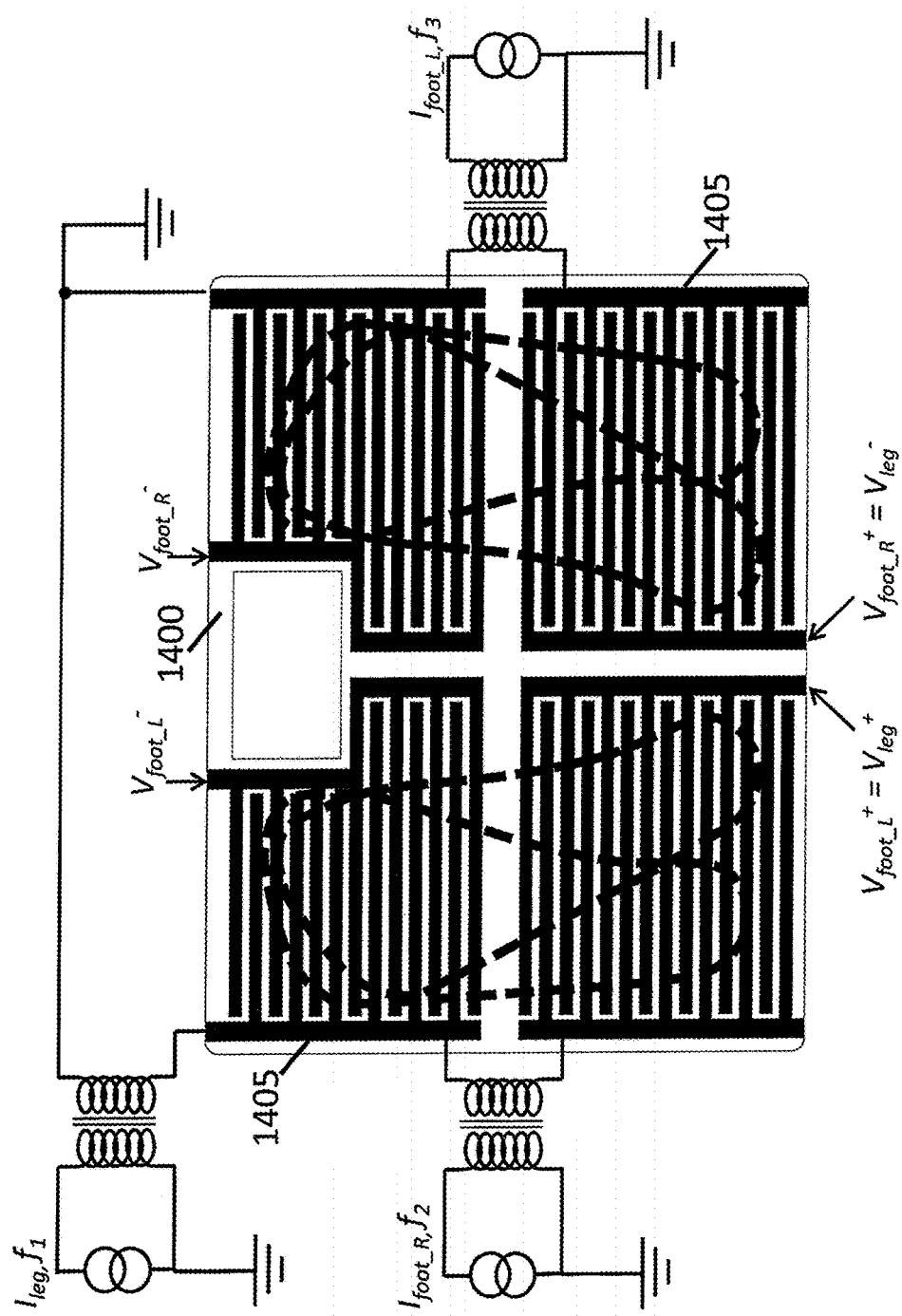

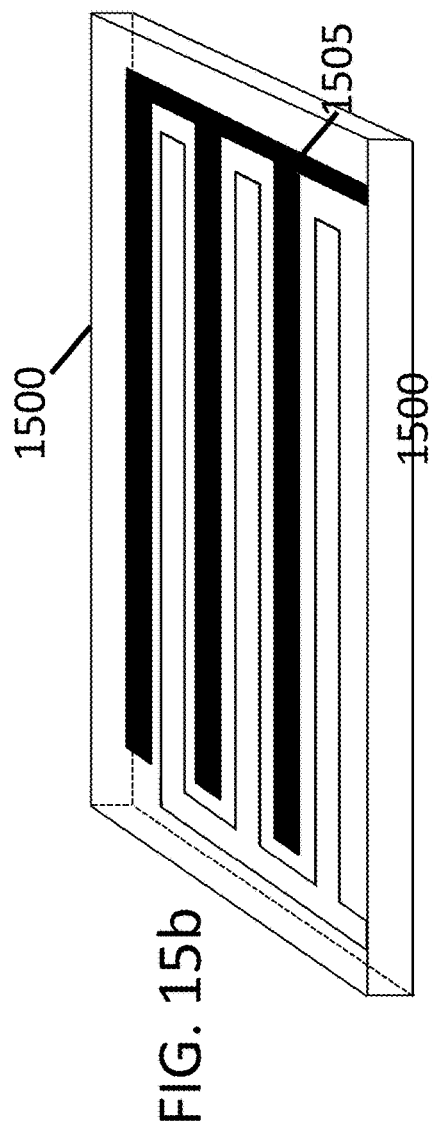
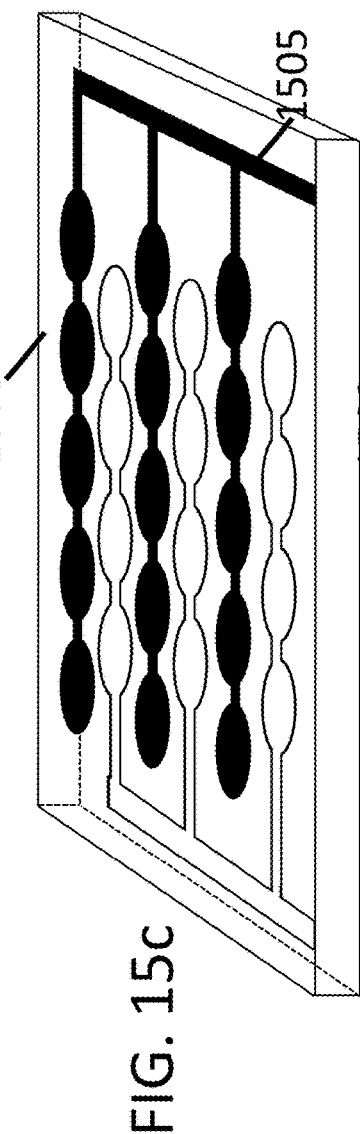
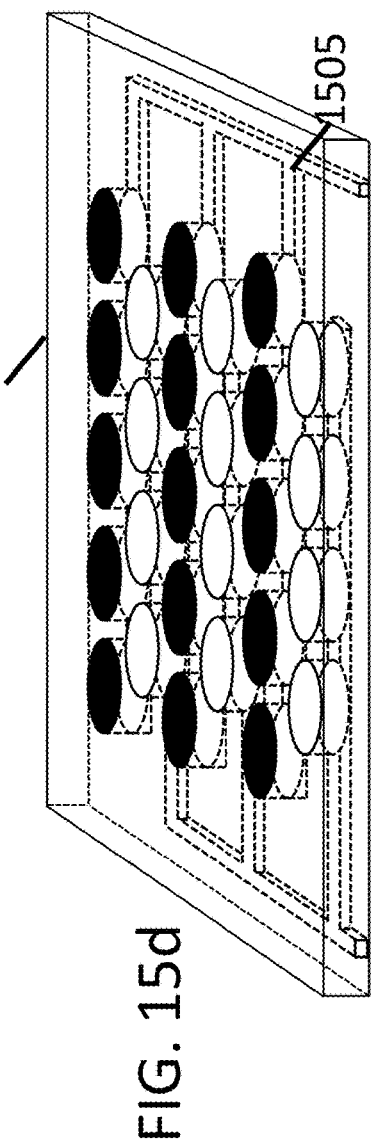
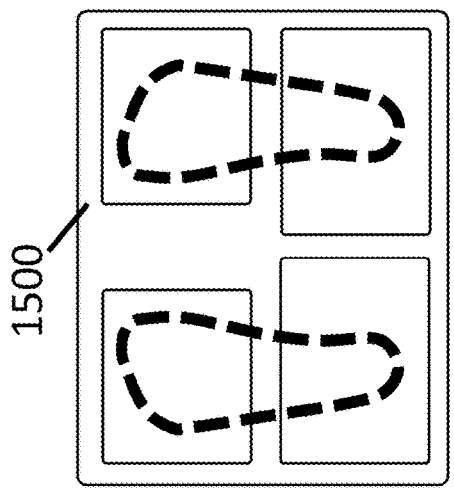
FIG. 15b
FIG. 15c
FIG. 15d
FIG. 15a

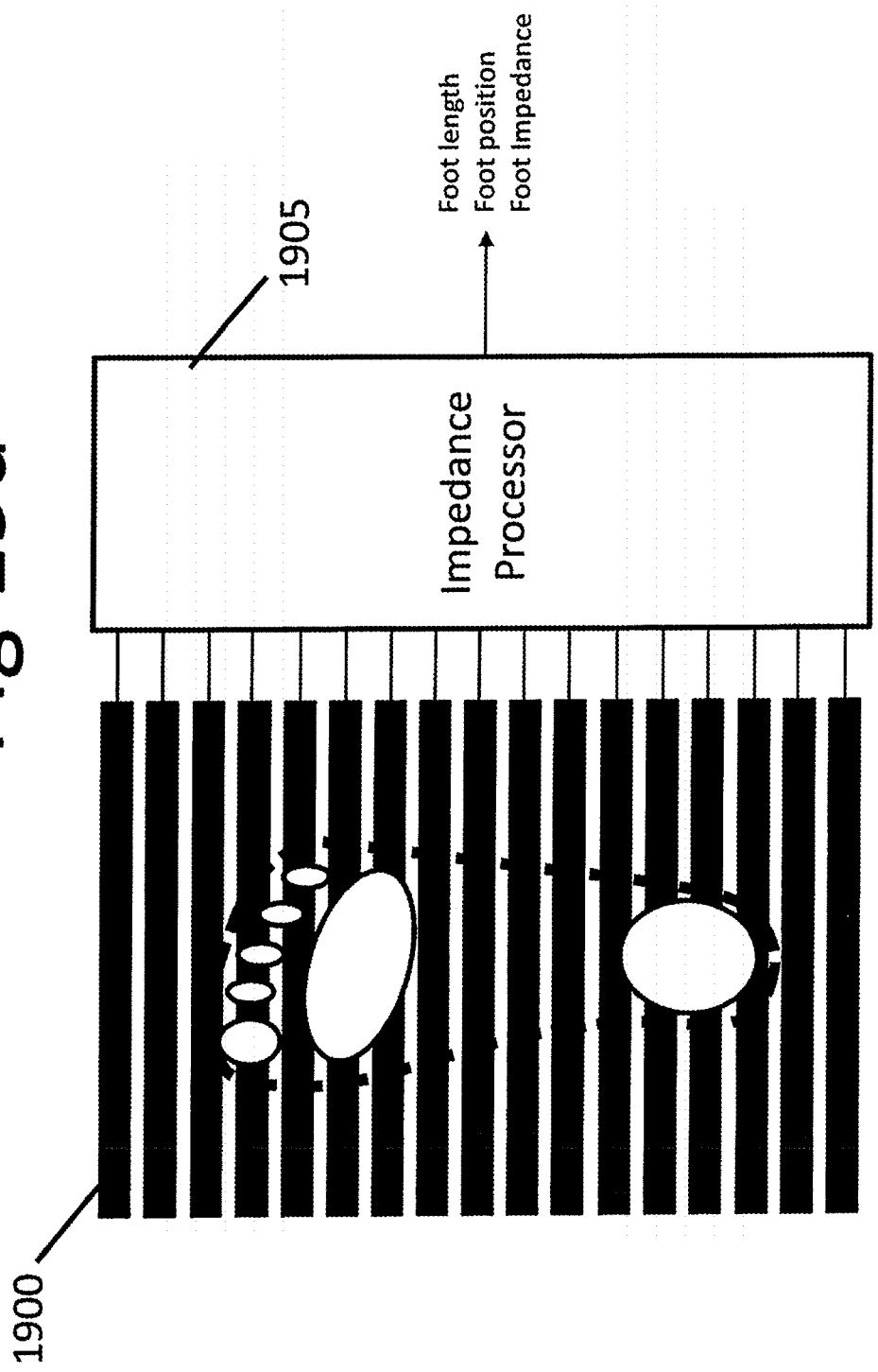

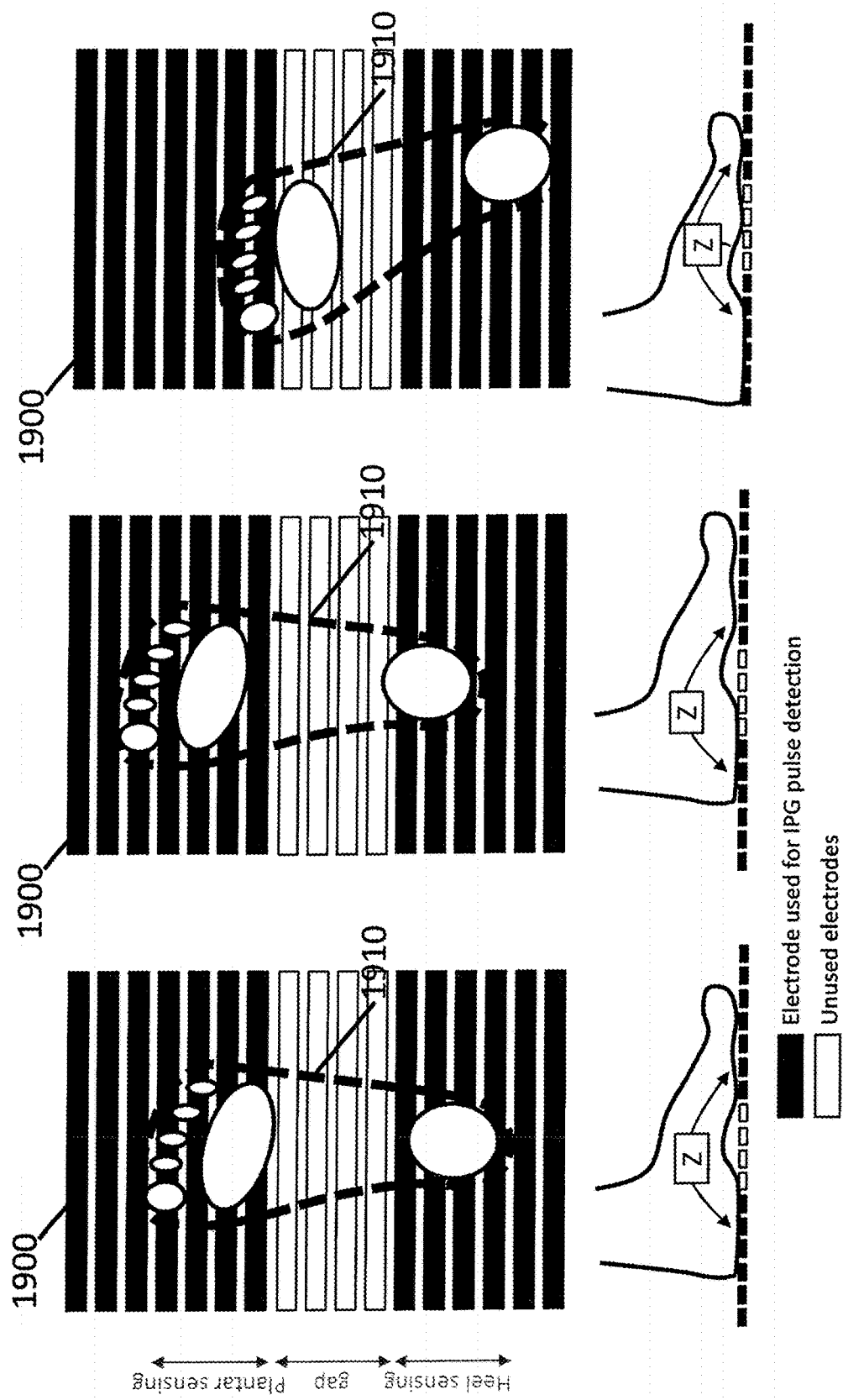

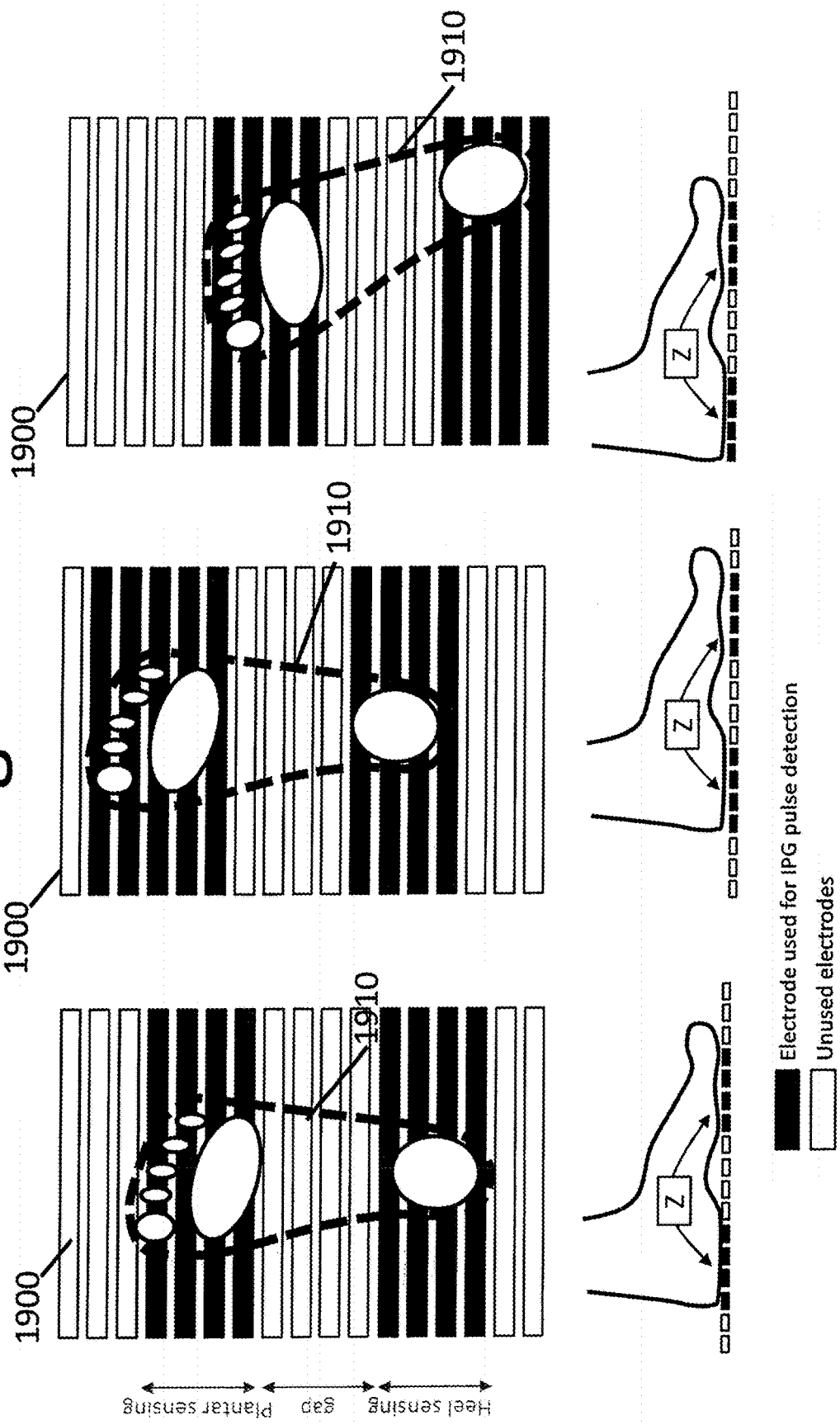

CONDITION OR TREATMENT ASSESSMENT METHODS AND PLATFORM APPARATUSES

RELATED APPLICATION DATA

This application is related to PCT Application (Ser. No. PCT/US2016/062484), entitled "Scale-Based Parameter Acquisition Methods and Apparatuses", filed on Nov. 17, 2016, PCT Application (Ser. No. PCT/US2016/062505), entitled "Remote Physiologic Parameter Assessment Methods and Platform Apparatuses", filed on Nov. 17, 2016, U.S. Provisional Application (Ser. No. 62/258,253), entitled "Initialization Methods and Device for User Physiological Platforms", filed Nov. 20, 2015, U.S. Provisional Application (Ser. No. 62/258,238), entitled "Condition or Treatment Assessment Methods and Platform Apparatuses", filed Nov. 20, 2015, and U.S. Provisional Application (Ser. No. 62/266,523) entitled "Social Grouping Using a User-Specific Scale-Based Enterprise System", filed Dec. 11, 2015", which are fully incorporated herein by reference.

OVERVIEW

Various aspects of the present disclosure are directed toward methods, systems and apparatuses that are useful in assessing a condition or treatment of a user using physiologic parameter data obtained using a platform apparatus.

Various aspects of the present disclosure are directed toward monitoring a variety of different physiological characteristics for many different applications. For instance, physiological monitoring instruments are often used to measure a number of patient vital signs, including blood oxygen level, body temperature, respiration rate and electrical activity for electrocardiogram (ECG) or electroencephalogram (EEG) measurements. For ECG measurements, a number of electrocardiograph leads may be connected to a patient's skin, and are used to obtain a signal from the patient.

Obtaining physiological signals (e.g., data) can often require specialty equipment and intervention with medical professionals. For many applications, such requirements may be costly or burdensome. These and other matters have presented challenges to monitoring physiological characteristics.

Various aspects of the present disclosure are directed toward multisensory biometric devices, systems and methods. Aspects of the present disclosure include user-interactive platforms, such as scales, large and/or full platform-area or dominating-area displays and related weighing devices, systems, and methods. Additionally, the present disclosure relates to electronic body scales that use impedance-based biometric measurements. Various other aspects of the present disclosure are directed to biometrics measurements such as body composition and cardiovascular information. Impedance measurements can be made through the feet to measure fat percentage, muscle mass percentage and body water percentage. Additionally, foot impedance-based cardiovascular measurements can be made for an ECG and sensing the properties of blood pulsations in the arteries, also known as impedance plethysmography (IPG), where both techniques can be used to quantify heart rate and/or pulse arrival timings (PAT). Cardiovascular IPG measures the change in impedance through the corresponding arteries between the sensing electrode pair segments synchronous to each heartbeat.

In certain embodiments, the present disclosure is directed to apparatuses and methods including a platform in which a plurality of electrodes are integrated and configured and arranged for engaging a user, a user-display configured with the platform and the plurality of electrodes to output user-specific information, and processing circuitry. The processing circuitry includes a CPU and a memory circuit with user data stored in the memory circuit. The processing circuitry is arranged with (e.g., electrically integrated with or otherwise in communication) the force sensor circuitry and the plurality of electrodes to collect physiologic parameter data from the user while the user is standing on the platform using signals obtained by the plurality of electrodes and the force sensor circuitry. In specific aspects, the processing circuitry is electrically integrated with the plurality of electrodes, configured and arranged to process the user-corresponding data with physiologic parameter data obtained while the user is standing on the platform and therefrom derive and output derivation data indicative of a physiologic status of the user for assessment of a condition or treatment of the user that corresponds with the physiologic status, and, store, in response to the derived derivation data, additional data in the memory circuit to supplement the user-corresponding data with information corresponding to the physiologic parameter data obtained while the user is standing on the platform.

In various embodiments, the electrodes are configured to obtain a plurality of measurement signals while the electrodes are concurrently contacting the user. While the plurality of electrodes is concurrently contacting a limb or other extremity of the user, a plurality of impendence-measurement signals is obtained from the plurality of electrodes. These impendence-measurement signals may (optionally) be the above-noted measurement signals. Based on biometrics of the user while approaching the platform, assessing who the user is while on the platform, and/or the plurality of measurement signals obtained from the plurality of electrodes, the CPU is used to access the user-corresponding data stored in the memory circuit, and thereby automatically recognize the user. This recognition is used for one or more of a variety of actions including, among others, transitioning from a low-power mode to a higher (power-up) mode, logging the user into the system and user-based logging of data and usages, and assessing which set of platform electrodes to use for obtaining the impendence-measurement signals. Based on a plurality of impedance-measurement signals being obtained from the electrodes while contacting the user, user-specific signals are generated and that correspond to the cardiovascular timings of the user.

In certain embodiments, aspects as described herein are implemented in accordance with and/or in combination with aspects of the underlying PCT Application (Ser. No. PCT/US2016/062484), entitled "Scale-Based Parameter Acquisition Methods and Apparatuses", filed on Nov. 17, 2016, PCT Application (Ser. No PCT/US2016/062505), entitled "Remote Physiologic Parameter Assessment Methods and Platform Apparatuses", filed on Nov. 17, 2016, U.S. Provisional Application (Ser. No. 62/258,253), entitled "Initialization Methods and Device for User Physiological Platforms", filed Nov. 20, 2015, Provisional Application (Ser. No. 62/258,238), entitled "Condition or Treatment Assessment Methods and Platform Apparatuses", filed Nov. 20, 2015, and Provisional Application (Ser. No. 62/266,523) entitled "Social Grouping Using a User-Specific Scale-Based Enterprise System", filed Dec. 11, 2015, to which benefit is claimed and which are fully incorporated herein by reference.

The above discussion/summary is not intended to describe each embodiment or every implementation of the present disclosure. The figures and detailed description that follow also exemplify various embodiments.

BRIEF DESCRIPTION OF THE DRAWINGS

Various example embodiments may be more completely understood in consideration of the following detailed description in connection with the accompanying drawings, in which:

FIG. 2a shows an example of the insensitivity to foot placement on scale electrodes with multiple excitation and sensing current paths, consistent with various aspects of the present disclosure;

FIGS. 2b-2c show examples of electrode configurations, consistent with various aspects of the disclosure;

FIG. 6a shows examples of the Leg IPG signal with fiducials; the segmented Leg IPG into beats; and the ensemble-averaged Leg IPG beat with fiducials and calculated SNR, for an exemplary high-quality recording, consistent with various aspects of the present disclosure;

FIG. 6b shows examples of the Foot IPG signal with fiducials derived from the Leg IPG fiducials; the segmented Foot IPG into beats; and the ensemble-averaged Foot IPG beat with fiducials and calculated SNR, for an exemplary high-quality recording, consistent with various aspects of the present disclosure;

FIG. 7a shows examples of the Leg IPG signal with fiducials; the segmented Leg IPG into beats; and the ensemble averaged Leg IPG beat with fiducials and calculated SNR, for an exemplary low-quality recording, consistent with various aspects of the present disclosure;

FIG. 7b shows examples of the Foot IPG signal with fiducials derived from the Leg IPG fiducials; the segmented Foot IPG into beats; and the ensemble-averaged Foot IPG beat with fiducials and calculated SNR, for an exemplary low-quality recording, consistent with various aspects of the present disclosure;

FIG. 8 shows an example correlation plot for the reliability in obtaining the low SNR Foot IPG pulse for a 30-second recording, using the first impedance signal as the trigger pulse, from a study including 61 test subjects with various heart rates, consistent with various aspects of the present disclosure;

FIGS. 9a-b show an example configuration to obtain the pulse transit time (PTT), using the first IPG as the triggering pulse for the Foot IPG and ballistocardiogram (BCG), consistent with various aspects of the present disclosure;

FIG. 10 shows nomenclature and relationships of various cardiovascular timings, consistent with various aspects of the present disclosure;

FIG. 14b shows another example of a scale with interleaved foot electrodes to inject and sense current from one foot to another foot, and measure Foot IPG signals in both feet, consistent with various aspects of the present disclosure;

FIG. 14c shows another example approach to floating current sources is the use of transformer-coupled current sources, consistent with various aspects of the present disclosure;

FIGS. 15a-d show an example breakdown of a scale with interleaved foot electrodes to inject and sense current from one foot to another foot, and within one foot, consistent with various aspects of the present disclosure;

FIGS. 19a-c show example impedance as measured through different parts of the foot based on the foot position, consistent with various aspects of the present disclosure.

Figure 1A:
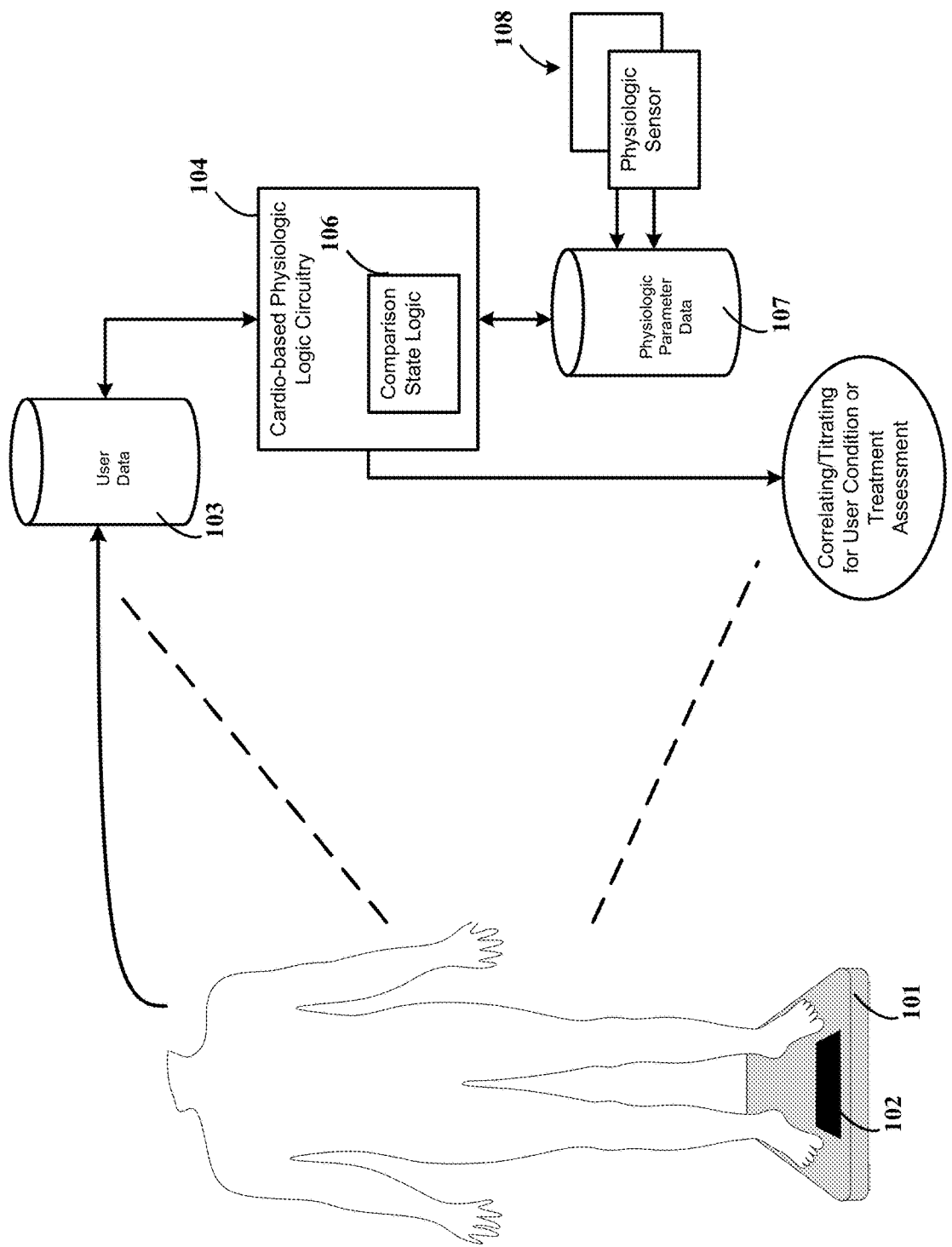
FIG. 1a shows an apparatus consistent with aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DESCRIPTION

Aspects of the present disclosure are believed to be applicable to a variety of different types of apparatuses, systems, and methods involving outputting derivation data indicative of a physiological status of a user for assessment of a condition or treatment of the user. In certain implementations, aspects of the present disclosure have been shown to be beneficial when used in the context of a weighing scale with electrodes configured for engaging with the user and collecting physiological parameter data, such as data indicative of a BCG or ECG of a user. In some embodiments, the weighing scale outputs the derivation data indicative of the physiological status to external circuitry that is at a remote location for assessment of the condition or treatment of the user. These and other aspects can be implemented to address challenges, including those discussed in the background above. While not necessarily so limited, various aspects may be appreciated through a discussion of examples using such exemplary contexts.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

In accordance with a number of embodiments, physiological parameter data is collected using an apparatus, such as a weighing scale or other platform that the user. The user (e.g., owner of the scale or persons related to the owner, such as co-workers, friends, roommates, colleagues), may use the apparatus in the home, office, doctors office, or other such venue on a regular and frequent basis, the present disclosure is directed to a substantially-enclosed apparatus, as would be a weighing scale, wherein the apparatus includes a platform which is part of a housing or enclosure and a user-display to output user-specific information for the user while the user is standing on the platform. The platform includes a surface area with electrodes that are integrated and configured and arranged for engaging a user as he or she steps onto the platform. Within the housing is processing circuitry that includes a CPU (e.g., one or more computer processor circuits) and a memory circuit with user-corresponding data stored in the memory circuit. The platform, over which the electrodes are integrated, is integrated and communicatively connected with the processing circuitry. The processing circuitry is programmed with modules as a set of integrated circuitry which is configured and arranged for automatically obtaining a plurality of measurement signals (e.g., physiological parameter data) from the plurality of electrodes.

The physiological parameter data collected, in various embodiments, is indicative of a physiological status of the user and is used for assessment of a condition or treatment of the user that corresponds with the physiologic status. The physiological parameter data includes signals obtained using the electrodes, force sensor circuitry, and the processing circuitry. In other embodiments and/or in addition, the physiologic parameter data includes an ECG, BCG, PWV, heartrate, balance, tremors, respiration, among other parameters and/or a combination thereof. For example, the physiological parameter data is processed by the processing circuitry, and therefrom, the processing circuitry derives and outputs derivation data indicative of the physiological status of the user. Example derivation data includes time-stamped raw signals obtained using the electrodes, physiological parameters determined using the physiological parameter data, and/or time-stamped physiological parameters, among other data that is correlated with various user-corresponding data. Example user-corresponding data includes age, weight, height, gender, exercise habits, cholesterol levels, etc. Further, the processing circuitry stores, in response to the derivation data, additional data in the memory circuit to supplement the user-corresponding data with information corresponding to the physiological parameter data obtained while the user is standing on the platform. The additional data can include physiological parameter data, additional user-corresponding data (e.g., age, weight, height, gender, cholesterol level), and/or other data.

In accordance with various embodiments, the processing circuitry and/or an external circuitry determines physiologic parameter data of the user using the derivation data and assesses the physiological parameter data of the user for a treatment or condition. The processing and/or external circuitry correlates the user with a condition or treatment by comparing the physiologic parameter data of the user to reference information. The reference information can include look up tables, rules, indexes, graphs, and/or a plurality of operations. For example, the reference information includes a range of values for the physiologic parameter of other users having corresponding condition or treatment indications and that have a similar demographic background of the user. In various embodiments, the processing and/or external circuitry determines the reference information, such as from a plurality of reference information, based on the user-corresponding data. The user-corresponding data is indicative of the demographic background of the user. In a number of embodiments, the assessed condition or treatment can then be sent to external circuitry. By assessing a condition or treatment of the user remotely from the apparatus and/or outputting the condition or treatment to the external circuitry, the appropriate personal, such as a physician, can view the condition or treatment assessment prior to the user and verify the accuracy of the condition or treatment. In various embodiments, the physician prescribes medication and/or uses the assessed condition or treatment to advice the user and/or further evaluate the user. In various embodiments, the user data is compared against historical user data for the same user and used to analyze if the user's condition/treatment and risk is getting better or worse over time.

In various specific embodiments, the scale can be used to enable prescription drug titration. Drug titration include identifying a dose (or amount) of the drug that controls or mitigates symptoms for a user. The scale can be used to perform drug titration based on and/or considering a dose of the drug that controls or effects optimization of symptoms and side effect minimization. For example, the dosage can be controlled to effect or mitigate symptoms with the fewest side effects. For example, a user can be given an initial dosage of a prescription drug and various physiological parameters are tracked over a period of time using the scale. The tracked physiological parameters are used to determine symptoms (or signs) the user is experiencing and/or side effects. The dosage is adjusted, depending on the results, and the physiological parameters are tracked to determine if the adjusted dosage is better (controls symptoms or mitigates side effects) than the initial dosage. The scale can be used as a feedback to determine the dose for the user that controls or mitigates symptoms with the fewest side effects. Such feedback can be particularly useful with user on multiple prescription drugs for different symptoms and prescription drugs that may interact.

In accordance with various embodiments, the collected physiologic parameter data is based on sensing, detection, and quantification of at least two simultaneously acquired impedance-based signals. The simultaneously acquired impedance-based signals are associated with quasi-periodic electro-mechanical cardiovascular functions, and simultaneous cardiovascular signals measured by the impedance sensors, due to the beating of an individual's heart, where the measured signals are used to determine at least one cardiovascular related characteristic of the user for determining the heart activity, health, or abnormality associated with the user's cardiovascular system. The sensors can be embedded in a user platform, such as a weighing scale-based platform, where the user stands stationary on the platform, with the user's feet in contact with the platform, where the impedance measurements are obtained where the user is standing with bare feet.

In certain embodiments, the plurality of impedance-measurement signals includes at least two impedance-measurement signals between the one foot and the other location. Further, in certain embodiments, a signal is obtained, based on the timing reference, which is indicative of synchronous information and that corresponds to information in a BCG. Additionally, the methods can include conveying modulated current between selected ones of the electrodes. The plurality of impedance-measurement signals may, for example, be carried out in response to current conveyed between selected ones of the electrodes. Additionally, the methods, consistent with various aspects of the present disclosure, include a step of providing an IPG measurement within the one foot. Additionally, in certain embodiments, the two electrodes contacting one foot of the user are configured in an inter-digitated pattern of positions over a base unit that contains circuitry communicatively coupled to the inter-digitated pattern. The circuitry uses the inter-digitated pattern of positions for the step of determining a plurality of pulse characteristic signals based on the plurality of impedance-measurement signals, and for providing an IPG measurement within the one foot. As discussed further herein, and further described in U.S. patent application Ser. No. 14/338,266 filed on Oct. 7, 2015, which is herein fully incorporated by reference for its specific teaching of inter-digitated pattern and general teaching of sensor circuitry, the circuitry can obtain the physiological data in a number of manners.

In medical (and security) applications, for example, the impedance measurements obtained from the plurality of integrated electrodes can then be used to provide various cardio-related information that is user-specific including, as non-limiting examples, synchronous information obtained from the user and that corresponds to information in a ballistocardiogram (BCG) and an impedance plethysmography (IPG) measurements. By ensuring that the user, for whom such data was obtained, matches other bio-metric data as obtained concurrently for the same user, medical (and security) personnel can then assess, diagnose and/or identify with high degrees of confidence and accuracy.

Turning now to the figures, FIG. 1a shows an apparatus consistent with aspects of the present disclosure. The apparatus includes a platform 101 and a user-display 102. The user, as illustrated by FIG. 1a is standing on the platform 101 of the apparatus. The user-display 102 is arranged with the platform 101. As illustrated by the dashed-lines of FIG. 1a, the apparatus includes processing circuitry 104 and physiologic sensors 108. That is, the dashed-lines illustrate a closer view of components of the apparatus.

The physiologic sensors 108, in various embodiments, include a plurality of electrodes and force sensor circuitry (e.g., strain gauges) integrated with the platform 101. The electrodes and corresponding force-sensor circuitry are configured to engage with the user and to collect signals. For example, the signals can be indicative of and/or include the physiological parameter data of the user, such as data indicative of a BCG or ECG and/or direct weight or heartrate data, among other data. As discussed further below, the signals can be force signals. The user display 102 is arranged with the platform 101 and the electrodes to output user-specific information for the user while the user is standing on the platform 101. The processing circuitry 104 includes a CPU and a memory circuit with user-corresponding data 103 stored in the memory circuit. The processing circuitry 104 is arranged under the platform 101, and is electrically integrated with the plurality of electrodes.

In various embodiments, the processing circuitry 104 is electrically integrated with the plurality of electrodes and force sensor circuitry and configured to process the user-corresponding data with physiologic parameter data. During the processing, the apparatus can be in a comparison state. In a number of embodiments, the processing circuitry includes logic, such as the comparison state logic 106, that is executed to perform one or more of the operations and/or activities regarding the derivation data, and/or assessment. The processing can include correlating the collected physiologic parameter data with user-corresponding data. In various embodiments, the user-corresponding data can include information such as height, weight, gender, age, ethnicity, exercise habits, eating habits, cholesterol levels, previous health conditions or treatments, family medical history, and/or a historical record of variations in one or more of the listed information. The processing circuitry 104 (e.g., the cardio-based physiologic logic circuit) derives and outputs, therefrom, derivation data indicative of a physiologic status of the user for assessment of a condition or treatment of the user that corresponds with the physiologic status. A physiologic status, as used herein, is status of cardio-health of the user, and can include risk factors and/or indicators.

The user-corresponding data includes information about the user (that is or is not obtained using the physiologic sensors 108) such as demographic information or historical information. Example user-corresponding data includes height, gender, age, ethnicity, exercise habits, eating habits, cholesterol levels, previous health conditions or treatments, family medical history, and/or a historical record of variations in one or more of the listed data. The user-corresponding data is obtained directly from the user (e.g., the user inputs to the scale) and/or from another circuit (e.g., a smart device, such a cellular telephone, smart watch and/or fitness device, cloud system, etc.). The user-corresponding data 103 is input and/or received prior to the user standing on the scale and/or in response to.

The physiologic parameter data, in accordance with various embodiments, includes force signals, PWV, weight, heartrate, BCG, balance, tremors, respiration, data indicative of one or more of the proceeding data, and/or a combination thereof. In some embodiments, the physiologic parameter data includes the raw force signals and additional physiologic parameter data is determined using external circuitry. Alternatively, the physiological parameter data can include physiologic parameters such as the PWV, BCG, ECG that are determined using the force signals from the electrodes and the external circuitry (or the processing circuitry 104 of the scale) can determine additional physiological parameter (such as determining the BCG using the ECG) and/or assess the user for a condition or treatment using the physiological parameter. An algorithm to determine the physiologic data from raw signals can be located on the scale, on another device (e.g., external circuitry, cellphone), and on a Cloud system. For example, the Cloud system can learn to optimize the determination and program the scale to subsequently perform the determination locally. The Cloud system can perform the optimization and programming for each user of the scale.

In some embodiments, the scale collects physiologic data from other devices, such as medical devices, user devices, wearable devices, and/or remote-physiological devices. The data can include glucose measurements, blood pressure, ECG or other cardio-related data, body temperature, among other physiologic data. Further, the scale can act as a hub to collect data from a variety of sources. The sources includes the above-noted user devices. The scale can incorporate a web server (URL) that allows secure, remote access to the collected data. For example, the secure access can be used to provide further analysis and/or services to the user.

The derivation data is used for assessment of a condition or treatment of the user that corresponds with the physiologic status. That is, using the processing circuitry 104, the apparatus outputs data indicative of correlation/titration of the user for condition or treatment assessment. The assessment, as discussed further herein, is performed by the processing circuitry 104 and/or external circuitry. The processing circuitry 104 can store, in response to the derivation data, additional data in the memory circuit to supplement the user-corresponding data with information corresponding to the physiologic parameter data obtained while the user is standing on the platform 101. The additional data includes suggestions to the user based on the assessment, in some embodiments.

The derivation data, in accordance with various embodiments, is output to the user display 102 for display and/or to external circuitry that is at a remote location and that is not integrated with the platform 101. In embodiments in which the derivation data is output to external circuitry, the external circuitry assesses the user for a condition or treatment that corresponds with the physiologic status. In some embodiments, the external circuitry determines additional physiological parameter data of the user using the derivation data, as discussed above (e.g., determine PWV using the force signals).

The external circuitry (and/or the processing circuitry) assesses the user for a condition or treatment, in various embodiments. For example, the external circuitry can correlate the user with the condition or treatment by comparing the physiological parameter data and/or the additional physiological parameter data of the user to reference information. Reference information, as used herein, includes a range of values of the physiological parameter data for other users having corresponding condition or treatment indicators and wherein the other users are of a demographic background of the user. A demographic background includes similar age, gender, exercise habits, weight, height, diet, cultural-norm, etc., and/or various combinations thereof. Example reference information includes a lookup table, rules, an index, a graph, a plurality of operations, and a combination thereof. The indicators, in some embodiments, include values of the physiological parameter, diagnosis, changes in demographic information (change in weight), etc.

In accordance with various embodiments, the respective reference information is determined using user-corresponding data that is indicative of the demographic background of the user. For example, the external circuitry and/or the processor circuitry of the apparatus include a database with a plurality of reference information. The user-corresponding data, such as the data processed with the physiologic parameter data and/or including the derivation data, can be used to select and/or determine the respective reference information by identifying the demographic background of the user (e.g., and identifying reference information using the demographic background and associated with physiological parameter data). In some embodiments, the external circuit receives the user-corresponding data from the processing circuitry, from the user, and/or from another circuitry corresponding to the user (e.g., the user's mobile cellular telephone).

In some specific embodiments, the correlation of the user with the condition or treatment includes using a PWV of the user as an indicator for arterial stiffness by referring to the reference information that reveals an appropriate range of arterial stiffness for other users having corresponding arterial-stiffness indicators. Another specific embodiment includes using a PWV of the user as an indicator for fluid retention levels by referring to the reference table that reveals an appropriate range of fluid retention level for other users having corresponding fluid retention level indicators.

In some specific embodiments, the scale is used as a feedback for prescription drug titration. For example, the output derivation data can include physiological parameters related to a symptom the user is being treated for with a prescription drug or side effects of the prescription drug. As previously discussed, drug titration includes identifying a dose (or amount) of the drug that controls or effects optimization of symptoms and side effect minimization. For example, the dosage can be controlled to effect or mitigate symptoms with the fewest side effects. In some embodiments, drug titration consider dosage that controls or mitigate symptoms with the fewest side effects. Using the output derivation data, the scale or external circuitry determines an adjusted dose for the prescription drug, as described further herein.

For example, a user can be given an initial dosage of a prescription drug and various physiological parameters are tracked over a period of time using the scale. Prior to the initial dose, the scale tracks the same physiological parameter to establish a pre-drug baseline. The user stands on the scale periodically (e.g., at the same time in the morning, multiple time throughout the day, among other times) and the scale measures physiologic data. The scale may prompt the user with audio from the scale and/or via a paired cellphone or other user device (e.g., via audio, an alert, a text or email) at periodic times to remind the user to stand on the scale. In some embodiments, the user may stand on the scale hourly to determine the effect of the drug over time. For instance, the prescription drug dose may be effective during the first three hours and become ineffective after. Such information can be useful to determine how often to give the user the prescription drug. Such tracked physiological parameters can include weight, PWV, heartrate, BCG, tremors, balance, respiratory, among other parameters. The tracked physiological parameters are used to determine symptoms the user is experiencing and/or side effects. The dosage can be adjusted, depending on the results, and the same physiological parameters can be tracked to determine if the adjusted dosage is better (controls symptoms or mitigates side effects) than the initial dosage. For example, if the initial dose indicates the user is still experiencing the symptoms, the dose is increased and the physiological parameters are measured to determine if the increase dosage is controlling the symptoms and/or causing side effects. Thereby, the scale is used as a feedback to determine the dose for the user that controls or mitigates symptoms with the fewest side effects.

In a number of embodiments, the user (e.g., a patient) may adjust the dose or provide a recommendation to adjust the dosage. The user may be experiencing unwanted side effects or unwanted symptoms (or signs) and provides the recommendation or adjustment based on the same. As a specific example, a user with Parkinson may adjust the dosage to control Parkinson tremor.

In various embodiments, the scale further includes an output circuit. The output circuit receives the user data (e.g., the physiologic parameter data and/or user-corresponding data, derivation data, and/or assessment), in response, sends the user data, including the data indicative of the user's identity and the generated cardio-related physiologic data, from the scale for reception at a remote location (e.g., to external circuitry for assessment). In various embodiments, the output circuit provides data to user via a user interface. The user interface can be integrated with the platform 101 (e.g., internal to the scale) and/or can be integrated with external circuitry that is not located under the platform 101. In some embodiments, the user interface is a plurality of user interfaces, in which at least one user interface is integrated with the platform 101 and at least one user interface is not integrated with the platform 101.

The output circuit receives the user data and, in response, sends the user data, including the data indicative of the user's identity and the generated cardio-related physiologic data, from the scale for reception at a remote location (e.g., to external circuitry for assessment). In various embodiments, the output circuit provides data to user via a user interface. The user interface can be integrated with the platform 101 (e.g., internal to the scale) and/or can be integrated with external circuitry that is not located under the platform 101. In some embodiments, the user interface is a plurality of user interfaces, in which at least one user interface is integrated with the platform 101 and at least one user interface is not integrated with the platform 101.

A user interface includes or refers to interactive components of a device (e.g., the scale) and circuitry configured to allow interaction of a user with the scale (e.g., hardware input/output components, such as a screen, speaker components, keyboard, touchscreen, etc., and circuitry to process the inputs). A user display includes an output surface (e.g., screen) that shows text and/or graphical images as an output from a device to a user (e.g., cathode ray tube, liquid crystal display, light-emitting diode, organic light-emitting diode, gas plasma, touch screens, etc.) The user interface can be and/or include a GUI, a FUI, and/or voice based input/output circuitry which is integrated with the platform of the scale (e.g., internal to the scale) or is integrated with external circuitry that is not located or integrated with the platform of the scale, as further described herein. Further, the user interface can include multiple user interfaces, one of which is integrated with the scale and one that is not, as further described herein.

A FUI is a user interface that allows for the user to interact with the scale via inputs using their foot and/or via graphic icons or visual indicators near the user's foot while standing on the platform. In specific aspects, the FUI receives inputs from the user's foot (e.g., via the platform) to allow the user to interact with the scale. The user interaction includes the user moving their foot relative to the FUI, the user contacting a specific portion of the user display, etc. In a specific example, when the user stands on the platform of the scale, and the scale detects touching of the toe, the scale can reject the toe touch (or tap) as a foot signal (e.g., similar to wrist rejection for capacitive tablets with stylus).

A GUI is a user interface that allows the user to interact with the scale through graphical icons and visual indicators. As an example, the external circuitry includes a GUI, processing circuitry, and output circuitry to communicate with the processing circuitry of the scale. The communication can include a wireless or wired communication. Example external circuitry can include a wired or wireless tablet, a cellphone (e.g., with an application), a smartwatch or fitness band, smartglasses, a laptop computer, among other devices. In other examples, the scale includes a GUI and voice input/output circuitry (as further described below) integrated in the platform 101. The user interact with the scale via graphical icons and visual indicators provided via the GUI and voice commands from the user to the scale.

Voice input/output circuitry (also sometimes referred to as speech input/output) can include a speaker, a microphone, processing circuitry, and other optional circuitry. The speaker outputs computer-generated speech (e.g., synthetic speech, instructions, messages) and/or other sounds (e.g., alerts, noise, recordings, etc.) The computer-generated speech can be predetermined, such as recorded messages, and/or can be based on a text-to-speech synthesis that generates speech from computer data. The microphone captures audio, such a voice commands from the user and produces a computer-readable signal from the audio. For example, the voice input/output circuitry can include an analog-to-digital converter (ADC) that translates the analog waves captured by the microphone (from voice sounds) to digital data. The digital data can be filtered using filter circuitry to remove unwanted noise and/or normalize the captured audio. The processing circuitry (which can include or be a component of the processing circuitry 104) translates the digital data to computer commands using various speech recognition techniques (e.g., pattern matching, pattern and feature matching, language modeling and statistical analysis, and artificial neural networks, among other techniques).

Although the present examples embodiments provided above are in reference to an external circuitry performing the assessment, embodiments in accordance with the present disclosure are not so limited. For example, the processing circuitry can determine the condition or treatment on based on the user-corresponding data and/or physiologic parameter data obtained while the user is standing on the platform 102. Specifically, the processing circuitry can determine the physiologic parameter data of the user using the derivation data and correlate the user with a condition or treatment by comparing the physiologic parameter data of the user to reference information. Further, in such embodiments, the processing circuitry optionally determines the reference information from a plurality of reference information using the user-corresponding data.

Figure 1B:
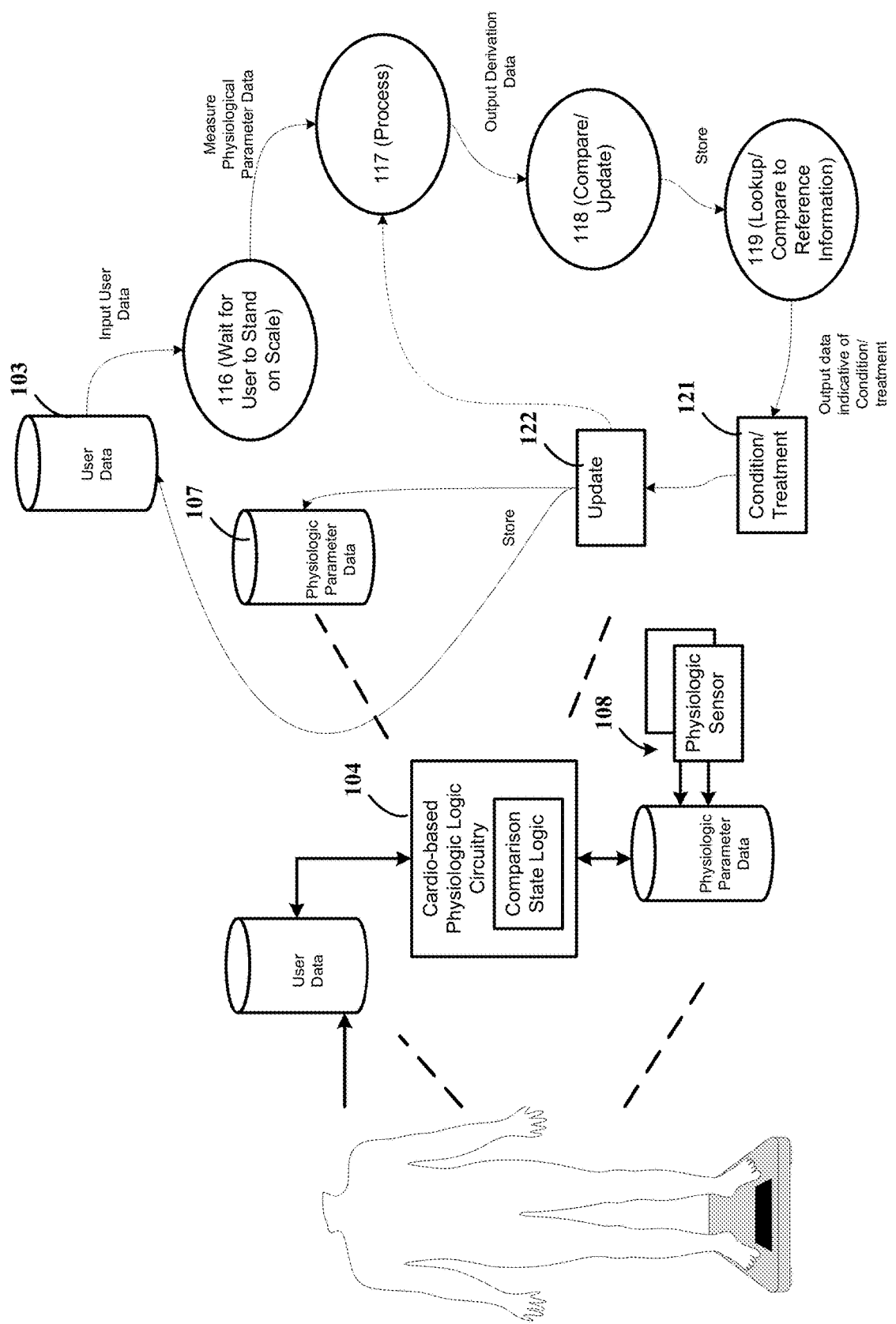
FIG. 1b shows an example of a user condition or treatment assessment using an apparatus consistent with aspects of the present disclosure.

FIG. 1b shows an example of a user condition or treatment assessment using an apparatus consistent with aspects of the present disclosure. The apparatus illustrated by FIG. 1b can include the apparatus, including the platform 101 and user display 102, as previously illustrated and discussed with regard to FIG. 1a. As illustrated, the apparatus includes a platform in which a plurality of electrodes (e.g., the physiologic sensors 108) are integrated, a user-display configured and arranged with the platform and the plurality of electrodes to output user-specific information for the user while the user is standing on the platform, and processing circuitry 104. The processing circuitry 104 includes a CPU and a memory circuit with user-corresponding data 103 stored in the memory circuit.

As previously discussed, the assessment of the condition or treatment can be a comparison state of the apparatus. The comparison state, in accordance with a number of embodiments, includes identifying the user is standing on the platform, confirming identification of the user, obtaining user-corresponding data 103 from the user and/or memory circuit, collecting physiologic parameter data 107, processing the user-corresponding data with the physiologic parameter data, and assessing the user for a condition or treatment. For example, as illustrated by FIG. 1B, during the comparison, the apparatus at block 116 waits for a user to stand on the platform apparatus. User-corresponding data 103 can be input and/or received prior to the user standing on the platform apparatus and/or in response to. Further, in response to the user standing on the apparatus, the apparatus obtains the physiologic parameter data 107. Example physiologic parameter data includes force signals, PWV, weight, heartrate, BCG, balance, tremors, respiration, and a combination thereof.

The processing circuitry 104, at block 117, processes the user-corresponding data 103 with the physiologic parameter data 107, and derives and outputs therefrom derivation data. The output, in various embodiments can be to the external circuitry and/or to the memory circuit of the processing circuitry 104. The derivation data is indicative of a physiological status of the user. In various embodiments the processing includes adding (and later storing) data with a time stamp indicating a time at about when the physiologic parameter data is obtained.

At block 118, the processing circuitry 104 stores, in response to the derivation data, additional data in the memory circuit to supplement the user-corresponding data 103 with information corresponding to the physiological parameter data 107 obtained while the user is standing on the platform. The additional data can include information about the user physiological state, portions or all of the physiological parameter data, advice for the user, an indication that data has been collected, among other information.

As illustrated, at block 119, the derivation data and/or additional physiologic parameter data determined is compared to reference information. The comparison, as previous discussed, can occur using the processing circuitry 104 and/or external circuitry. Further, in response to the comparison, assessment data is generated and output that is indicative of the condition or treatment 121. The output can be to the external circuitry, the memory circuit of the processing circuitry 104, and/or a memory circuit of the external circuitry for later access and/or further assessment. In various embodiments, the condition and/or treatment is used to update 122 the memory circuit of the processing circuitry 104. The update can include an indication of the treatment or condition, or symptoms or side effects, which may be displayed to the user on the user-display, and/or generic information or advice to provide the user that is indicative of a person with the physiologic status corresponding to the treatment or condition.

In accordance with various embodiments, based on the comparison of the user data to the reference information, the scale and/or external circuitry can determine various advice. Such advice can include suggested treatments, prescriptions, and life-style changes (e.g., diet, exercise, sleeping habits). The advice may be provided to the user and/or stored. For example, in some embodiments, the advice may be provided to a physician associated with the user for further medical assessment and for potential treatment purposes.

In various embodiment, the comparison state can include repeated acts of processing the user-corresponding data 103 and physiologic parameter data 107. For example, the processing circuitry 104, as discussed above, can process the user-corresponding data and store, in response to the derived derivation data, additional data with a time stamp indicating a time at about when the physiological parameter data is obtained. Further, the processing circuitry 104 repeats the acts of processing the user-corresponding data and storing, in response to the derived derivation data at another subsequent time, and therefrom generate a refined set of derived derivation data to further supplement the user-corresponding data with information corresponding to the physiologic parameter data. Alternatively and/or in addition, the processing circuitry 104, in various embodiments, determines the condition or treatment of the user based on at least one of an updated measurement associated with the physiologic parameter data obtained while the user is standing on the platform, wherein the updated measurement is updated relative to a previous measurement corresponding to and/or stored with the user-corresponding data.

The scale can be used by multiple different users. A subset or each of the different users can have derivation data and/or condition or treatment determination performed by the scale and/or by external circuitry (e.g., response to the physiological data and/or derivation data output to external circuitry). For example, one or more of the users can activate a service for determining derivation data, a condition or treatment, and/or drug titration by providing a weighted value associated with the respective service. The scale and/or external circuitry can selectively track particular data based on the service and provide the condition or treatment, a physiological status, and/or feedback for drug titration, which can be updated over time, responsive to recognizing a particular user.

The scale can be used in different setting and/or modes, such as a consumer mode, a professional mode, and a combination mode. A consumer mode includes or refers to a scale as used and/or operated in a consumer setting, such as a dwelling. As a specific example, a scale is located in a dwelling with five different people. Each of the five different people use the scale, and three of the five people have previously provided inputs to the scale that activates a service corresponding to determining or providing the user with identification of a condition or treatment, a physiological status, and/or feedback for drug titration. Prior to providing the service to the user, the identity of the respective user is verified via the scale using scale-based biometric. Responsive to identifying the user, the scale and/or external circuitry perform the service. For example, the scale outputs physiological data and/or derivation data to the external circuitry. The external circuitry compares the output data to reference information and identifies the condition or treatment, the physiological status, and/or adjustment to the dosage of a drug, which is output to the scale and/or a portal for access by a physician. As users in a consumer mode may be familiar with one another (e.g., live together), the identification of the user by the scale can be based on weight, body-mass-index, and/or other data. Although embodiments are not so limited and the identification can be based on other biometrics and/or passcodes.

Biometrics, as used herein, are metrics related to human characteristics and used as a form of identification and access control. Scale-based biometrics includes biometrics that are obtained using signals collected by the data-procurement circuitry of the scale (e.g., using electrodes and/or force sensors). Example scale-based biometrics include foot length, foot width, weight, voice recognition, facial recognition, a passcode tapped and/or picture drawn with a foot of the user on the FUI/GUI of the user display, among other biometrics. In some specific embodiments, a scale-based biometric includes a toe-print (e.g., similar to a finger print) that is recognized using a toe-print reader on the FUI/GUI of the scale. The toe print can be used as a secure identification of the user. In other embodiments, the scale-based biometric includes a finger print captured using external circuitry in communication with the scale (e.g., a cellphone or tablet having finger print recognition technology).

In other instances the scale is used in a professional setting, such as a medical office, and/or in a professional mode. A professional mode includes or refers to an operation of the scale as used and/or operated in a professional setting, such as a doctor's office, exercise facility, nursing home, etc. In a professional mode, the scale is used by different users that may not be familiar with one another. The different users may have services with the professional to track and/or aggregate data from the peripheral device and/or to provide the physician with additional information. In some instances, a user can be provided additional health information as service while waiting for the professional, such as while waiting to see a doctor. The scale receives the additional health information from the external circuitry and either displays the additional health information using a user interface of the scale and/or via direct communication (e.g., WiFi, Bluetooth, NFC) with a user device (e.g., cellphone, tablet) that is within a threshold distance of the scale. Similar to the consumer mode, the scale can selectively provide the services by verifying the identity of the user using a biometric. The identification can include higher-level biometric and/or identification than the consumer mode.

As used herein, a user device includes processing circuitry and output circuitry to collect various data (e.g., signals) and communicate the data to the scale and/or other circuitry. Example user devices include cellphones, tablets, standalone server, among other devices. The user device can be a wearable device that is worn by a user, such as on a user's wrist, head, or chest. Example wearable devices include smartwatches and fitness bands, smart glasses, chest heart monitors, etc. In other aspects, the user device further includes sensor circuitry or other circuit to collect physiologic data from the user, and, can optionally be in secured communication with the scale or other circuitry. For example, the user device includes smartwatches or fitness bands that collect heart rate and/or ECG and/or body temperature, medical devices, implanted medical devices, smart beds, among other devices. Example physiologic data collected by user devices includes glucose measurements, blood pressure, ECG or other cardio-related data, body temperature, among other data. The terms "user device" and "wearable device", can be interchangeably used.

As a specific professional mode example, a scale is located at a doctor's office and is used to obtain data from multiple patients (e.g., 10 in a day, 500 in a year). When a patient checks-in, they stand on the scale and the scale-obtained data is output to external circuitry for document retention and/or other purposes. A subset (or all) of the patients have activated a service with doctor that corresponds with and/or includes providing additional health information while the user is waiting and/or based on categories of interest. For example, a user indicates an interest in learning more about atrial fibrillation (AFIB), which the scale outputs to external circuitry along with user data obtained by the scale. The external circuitry generates additional health information correlated with AFIB and the user data. For example, the additional health information includes various risks factors for AFIB and identifies lifestyle changes that can reduce the risk factors. The external circuitry communicates the additional health information to the scale via an Internet (or direct communication) connection and the scale outputs the additional health information to a cellphone of the user via an NFC or Bluetooth communication. The scale, in the professional mode, may be used to obtain data from more users than a scale used in a consumer setting.

The scale can also be in a combination consumer/professional mode. A combination consumer/professional mode includes or refers to a scale as used and/or operated in a consumer setting for purposes and/or uses by a professional, and/or in a professional setting for purposes and/or uses by the consumer (e.g., use by the consumer outside of the professional setting and/or in addition to). As a specific example, a scale is located at a user's dwelling and used by multiple family members. A first user of the family is diagnosed with a heart-related condition and the doctor may offer a service to perform drug titration using the scale (and optionally another user device). When the other family members stand on the scale, the scale operates in the consumer mode (which may include assessing a physiological status of the user). When the first user that is diagnosed with heart-related condition stands on the scale, the scale recognizes the user, outputs aggregated data from the scale to external circuitry that is accessible by the doctor of the first user, and the external circuitry identifies a suggested adjustment to the dosage. The scale can be used to obtain additional information related to symptoms and side effects and to further refine the drug titration.

Data provided to the user and/or the professional can default to be displayed on the user interface of the scale, the GUI of the user device, and/or a GUI of other external circuitry depending on the use of the scale. In a consumer mode and/or combination consumer/professional mode, data can default to display on the user interface of the scale. The defaulted display of data can be revised by the user providing inputs to display the data on the GUI of a user device or a GUI of another external circuitry (e.g., a standalone CPU) and/or automatically by the scale based on past scale-based actions of the user. As a specific example, a first user provides a user input to the scale to display data on the GUI of the user device multiple times (e.g., more than a threshold number of times, such as five times). In response, the scale adjusts the defaulted display and outputs data to the GUI of the user device. The display of data on the user interface of the scale and/or GUI of the user device (or other external circuitry) can include an indication of available additional health information, requests for categories of interest, and/or the additional health information, among other displays. In a professional mode, the scale is not owned by the user. The user may be uninterested in synchronizing their user device with the professional's scale. The display of data may default to the GUI of the user device to display an option to synchronize, and/or to override the synchrony. Alternatively, the display of data may default to the user interface of the scale to display an option to synchronize and, responsive to user verification or authority to synchronize, defaults to display on the GUI of the user device. During the combination consumer/professional mode, portions of scale-obtained data for a particular user may default to display on external circuitry, such as a standalone or server CPU that is accessible by the professional.

Figure 1C:
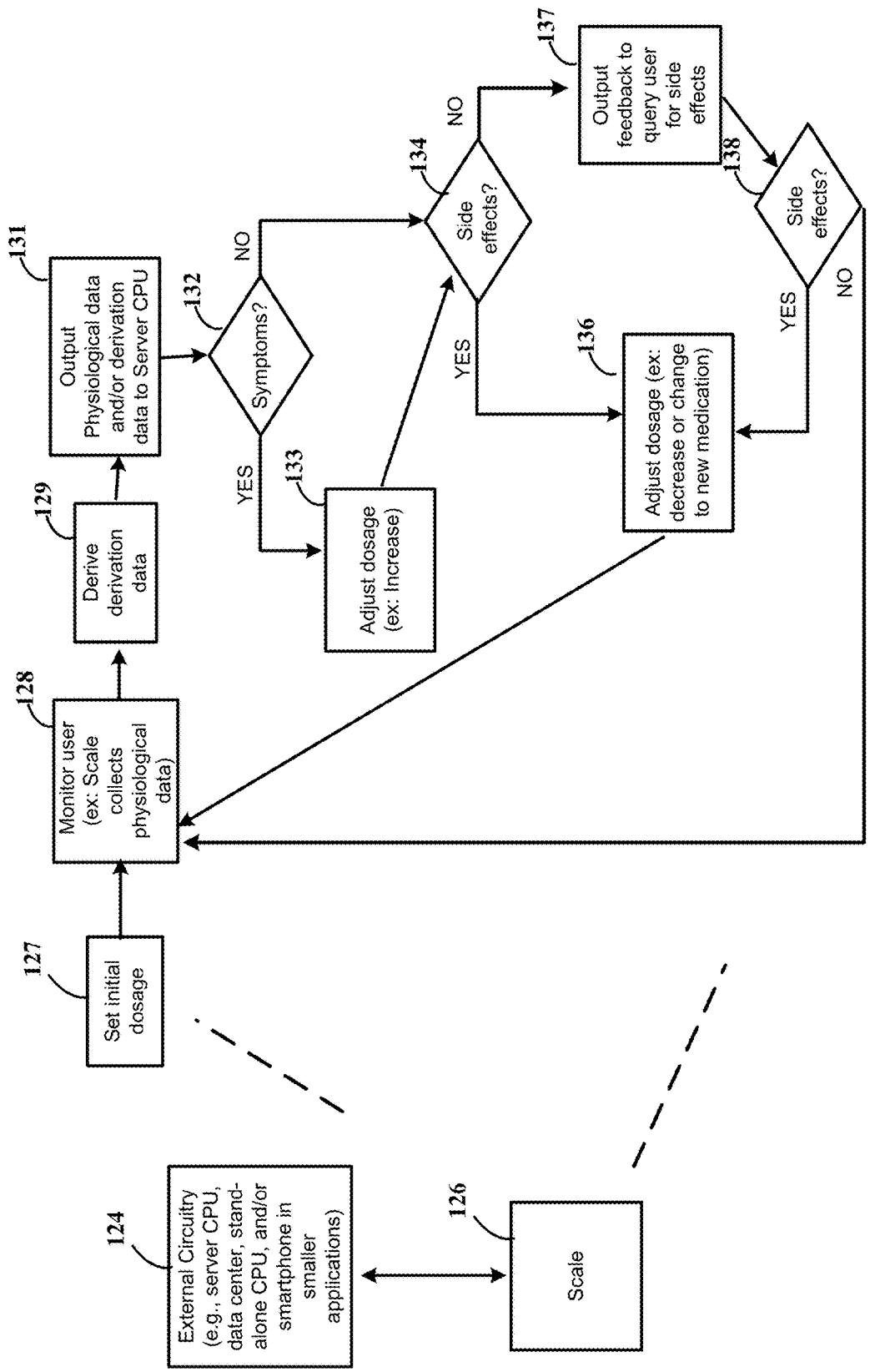
FIG. 1c shows an example process of drug titration using an apparatus consistent with aspects of the present disclosure.

FIG. 1c shows an example process of drug titration using an apparatus consistent with aspects of the present disclosure. Drug titration includes or refers to a process of identifying a dose (e.g., amount) and/or type of drug that controls or mitigates symptoms for a user. In specific embodiments, the drug titration can be used to mitigate symptoms (or signs) for a user while minimizing or controlling side-effects. In some embodiments, the apparatus includes a scale 126 and external circuitry 124. The scale 126 and external circuitry 124 can be used to perform drug titration based on and/or considering a dose of the drug that controls or mitigates symptoms with the fewest side effects. A symptom (e.g., felt or observed by the user) includes or refers to a subjective or objective sign or evidence of a disease or health condition. Example symptoms include anxiety, lower back pain, fatigue, skin rash, headache, blood cell counts, blood pressure, fever, weight loss, clubbing of fingers, bruising, skin color (e.g., yellowing of skin), anemic, among others. A side effect includes or refers to a secondary or peripheral effect of a drug. Side effects can be adverse or am undesirable secondary effect of a drug and/or treatment. Example side effects include fatigue, vomiting, decreased blood counts, hair loss, mouth sores, etc. Side effects can be mitigated or avoided by adjusting the dosage of the drug, changing drugs, adding a secondary drug to control or mitigate the side effects, dietary and/or other lifestyle changes, among other changes. The scale 126 is used to provide feedback to the external circuitry 124 for prescription drug titration, as described herein.

As illustrated by FIG. 1c, the user is given an initial dose of a prescription drug at 127. The initial dose can be set by a physician and based on demographics of the user (e.g., user weight, sex, height, age). Prior to the initial dose and/or prior to taking the initial dose, the scale is used to obtain pre-drug baseline values. For example, the scale monitors various physiological parameters to establish the pre-drug baselines. In response to the initial dose, the scale 126 is used to monitor various physiological parameters, and other data, over a period of time at 128. The scale 126 can be located at a dwelling of the user and/or at another location that the user can periodically access. Such tracked physiological parameters can include weight, PWV, heartrate, BCG, tremors, balance, respiratory, among other parameters. Using the monitored physiological data, the scale 126 can derive derivation data at 129. The derivation data is indicative of a physiological status of the user for assessment of a condition or treatment of the user that corresponds with the physiologic status. A physiologic status is or refers to a status of cardio-health of the user, and can include risk factors and/or indicators. Example derivation data includes time-stamped raw signals obtained using the electrodes, physiological parameters determined using the physiological data, and/or time-stamped physiological parameters, among other data that is correlated with various user-corresponding data. Example user-corresponding data includes age, weight, height, gender, exercise habits, cholesterol levels, etc. In various embodiments, the scale 126 obtains the user-corresponding data by querying the user using a user interface of the scale 126 and/or an external user interface (e.g., a GUI of another device in communication with the scale 126) that is in communication with the scale 126. For example, the output derivation data can include physiological parameters related to a symptom the user is being treated for with a prescription drug or side effects of the prescription drug.

As previously discussed, drug titration includes identifying a dose (or amount) of the drug that controls or effects optimization of symptoms and side effect minimization. For example, the dosage can be controlled to effect or mitigate symptoms with the fewest side effects. The scale 126 outputs the physiological data and/or derivation data to external circuitry 124, at 131. The external circuitry 124, using reference information, identifies if the user is experiencing symptoms. The identification can include identifying particular symptoms (or signs) and/or comparing to a threshold and can be based on the pre-drug baseline parameters. For example, certain medical conditions and/or diseases are associated with causing headaches and stomachaches. The scale queries the user to identify if the user is experiencing headaches and/or stomachaches. In response to the user indicating they are experience one or both symptoms, the scale can additional (and optionally) query the user to identify a rating (e.g., 1-10, with 1 being a low value and 10 being high) indicative of the severity of the symptoms. In other embodiments, the symptoms are a part of the derivation data. For example, the physiological data may indicate that the user is shaking (e.g., has higher balance movement and/or tremors as compared to pre-drug baseline balance movement and/or tremors) and/or has an increased heart rate (e.g., as compared to a pre-drug baseline heart rate). A symptom of the medical condition and/or disease may include tremors and/or causes heart issues. The scale may be used to verify the symptom by querying the user. In response to determining the user is experiencing symptoms, the external circuitry provides a message to adjust the dosage, at 133. The message can be provided via a portal that is accessible by the physician and/or other healthcare staff. The adjustment can include suggestion to increase the dosage and/or change prescriptions to a new prescription drug. Although not illustrated, the scale 126 may continue to monitor after the provided message to adjust the dosage. For example, a physician may view the message and, in response, contact the user to adjust the dosage. In other embodiments, the user may contact the physician and/or output a message suggesting to adjust the dosage to the physician, as previously described.

In response to determining the user is not experiencing symptoms (and/or experiencing below a threshold value) and/or after providing a message to adjust the dosage (at 133), the external circuitry 124 may determine if the user is experiencing side-effects at 134. The identification can include identifying particular side-effects and/or comparing the experience of the side-effect to a threshold. For example, certain medication are associated with causing headaches and stomachaches. The scale queries the user to identify if the user is experiencing headaches and/or stomachaches. In response to the user indicating they are experience one or both symptoms, the scale can additionally (and/or optionally) query the user to identify a rating (e.g., 1-10, with 1 being a low value and 10 being high) indicative of the severity of the side effect. In other embodiments, the presents of the side effect is a part of the derivation data. For example, the physiological data may indicate that the user is shaking (e.g., has higher balance movement and/or tremors)

and/or has an increased heart rate. A side effect of the drug may include tremors and causes heart issues. The scale 126 may be used to verify the side effect by querying the user. In response to determining the user is experiencing side effect, the external circuitry provides a message to adjust the dosage, at 136. The message can be provided via a portal that is accessible by the physician and/or other healthcare staff. The adjustment can include a suggestion to decrease the dosage, change prescriptions to a new prescription drug, and/or add a secondary prescription to control and/or mitigate the side effects.

In response to determining the derivation data is indicative of the user not experiencing side effects and/or experiencing side effects below a threshold, the external circuitry 124 can output a message, as feedback, to the scale 126 to query the user for potential side effects and/or a severity of the side effects. As described above, some side effects may be subjective and/or may otherwise not be measured using the scale 126. Using the headaches and/or stomachaches as an example, physiological data obtained by the scale (alone) does not indicate the present of the side effect. The external circuitry 124 may include or otherwise have access to a database containing reference information, which includes expected side effects of drugs. The scale 126 is used to query the user to identify the presents or not of the side effect and/or to qualify the severity of the side effect. The scale 126 outputs the user's responses to the query to the external circuitry 124 and the external circuitry, at 138, can again determine if the user is experiencing side effects and/or if the experience of one or more side effects is above a threshold. In response, at 136 and as described above, the external circuitry provides a message to adjust the dosage. In response to the adjustment and/or no identified side effects (or below threshold level), the scale 126 continues to monitor the user over time.

Although the present example illustrates titration of a single prescription drug, in various embodiments, the process and apparatus can be used to titrate a plurality of prescription drugs and/or identify side effects due to drug interactions between two or more of the plurality of drugs (which may or may not be prescription drugs). For example, certain diseases and/or health conditions can require a user to be prescribed multiple drugs. As a particular example, a user may have a heart condition and be on dialysis. The drugs used for dialysis may impact the user's heart and/or vice versa, and/or the combination may cause new side effects, such as confusion and disorientation. The apparatus and process described by FIG. 1c can be used to titrate multiple prescription drugs and potential identifying interactions between respective drugs. Further, in various embodiments, the external circuitry can be used for research purposes such as to identify new side effects of one or more drugs and/or between multiple drugs. Such side effects, in some instances, may not be detrimental to a user's health and can be used to identify new uses for drugs. For example, a first drug that is used for the above-describe heart condition may have a beneficial impacts on the user's kidney functions (e.g., dialysis related).

The remaining figures illustrate various ways to collect the physiologic data from the user, electrode configurations, and alternative modes of the processing circuitry 104. For general and specific information regarding the collection of physiologic data, electrode configurations, and alternative modes, reference is made to U.S. patent application Ser. No. 14/338,266 filed on Oct. 7, 2015, which is hereby fully incorporated by references for its teachings.

Figure 1D:
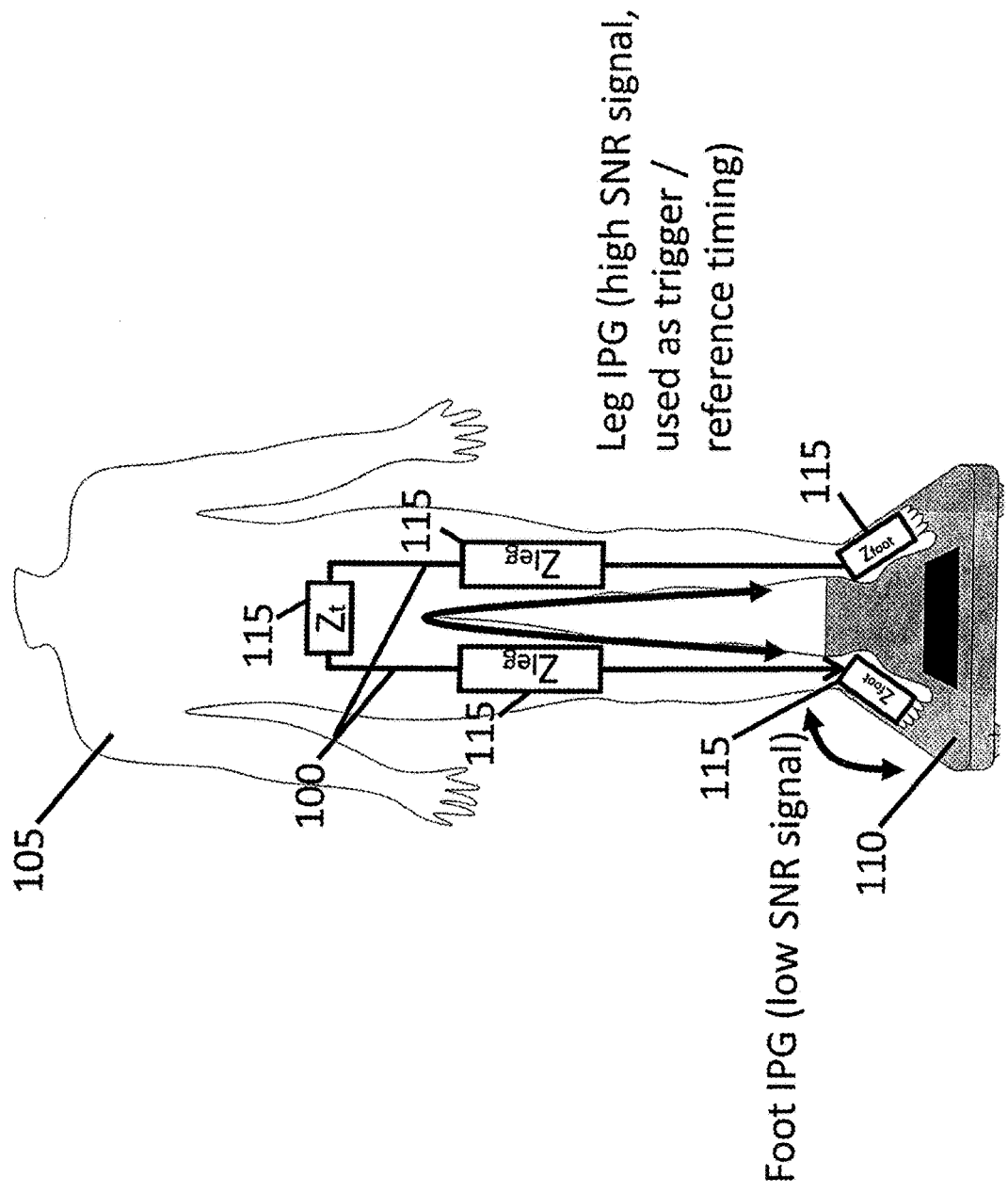
FIG. 1d shows current paths through the body for the IPG trigger pulse and Foot IPG, consistent with various aspects of the present disclosure.

FIG. 1d shows current paths 100 through the body of a user 105 standing on a scale 110 for the IPG trigger pulse and Foot IPG, consistent with various aspects of the present disclosure. Impedance measurements 115 are measured when the user 105 is standing and wearing coverings over the feet (e.g., socks or shoes), within the practical limitations of capacitive-based impedance sensing, with energy limits considered safe for human use. The measurements 115 can be made with non-clothing material placed between the user's bare feet and contact electrodes, such as thin films or sheets of plastic, glass, paper or wax paper, whereby the electrodes operate within energy limits considered safe for human use. The IPG measurements can be sensed in the presence of callouses on the user's feet that normally diminish the quality of the signal.

As shown in FIG. 1d, the user 105 is standing on a scale 110, where the tissues of the user's body will be modeled as a series of impedance elements, and where the time-varying impedance elements change in response to cardiovascular and non-cardiovascular movements of the user. ECG and IPG measurements sensed through the feet can be challenging to take due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals require a stable and high quality synchronous timing reference, to segment individual heartbeat-related signals for signal averaging to yield an averaged signal with higher SNR versus respective individual measurements.

The ECG can be used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noise from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scales is also influenced by measurement time. The number of beats obtained from heartbeats for signal averaging is a function of measurement time and heart rate. Typically, a resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S. The following is an example SE for uncorrelated noise:

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can require multiple solutions for SNR improvements for the signal being averaged. Longer measurement times increase the number of beats lost to truncation, false missed triggering, and excessive motion. Longer measurement times also reduce variability from cardiorespiratory effects. If shorter measurement times (e.g., less than 30 seconds) are desired for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure oxygen availability and is often the limiting factor for cell survival. The heart normally pumps five to six liters of blood every minute during rest and maximum cardiac output during exercise increases up to seven-fold, by modulating heart rate and stroke volume. The factors that affect heart rate include autonomic innervation, fitness level, age and hormones. Factors affecting stroke volume include heart size, fitness level, contractility or pre-ejection period, ejection duration, preload or end-diastolic volume, afterload or systemic resistance. The cardiovascular system is constantly adapting to maintain a homeostasis (set point) that minimizes the work done by the heart to maintain cardiac output. As such, blood pressure is continually adjusting to minimize work demands during rest. Cardiovascular disease encompasses a variety of abnormalities in (or that affect) the cardiovascular system that degrade the efficiency of the system, which include but are not limited to chronically elevated blood pressure, elevated cholesterol levels, edema, endothelial dysfunction, arrhythmias, arterial stiffening, atherosclerosis, vascular wall thickening, stenosis, coronary artery disease, heart attack, stroke, renal dysfunction, enlarged heart, heart failure, diabetes, obesity and pulmonary disorders.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracting the atria, the ventricles are filled with more blood and the depolarization then reaches the atrioventricular node and enters the ventricular side beginning the systole phase. The ventricles contract and the blood is pumped from the ventricles to arteries.

The ECG is the measurement of the heart's electrical activity and is described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as a timing reference for the cardiovascular cycle. Atrial repolarization is masked by the QRS complex. The ST interval represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases during the systole phase due to the high compliance (low stiffness) of the aortic wall. Blood traveling in the descending aorta bifurcates in the iliac branch which transitions into a stiffer arterial region due to the muscular artery composition of the leg arteries. The blood pulsation continues down the leg and foot. Along the way, the arteries branch into arteries of smaller diameter until reaching the capillary beds where the pulsatile blood flow turns into steady blood flow, delivering oxygen to the tissues. The blood returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and can be used to obtain reliable trigger fiducial timings from the Leg IPG signal. This acquisition can be far less sensitive to motion-induced noise from the Leg EMG that often compromises Leg ECG measurements. Furthermore, it has been discovered that interleaving the two Kelvin electrode pairs for a single foot, result in a design that is insensitive to foot placement within the boundaries of the overall electrode area. As such, the user is not constrained to comply with accurate foot placement on conventional single foot Kelvin arrangements, which are highly prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

Figure 1E:
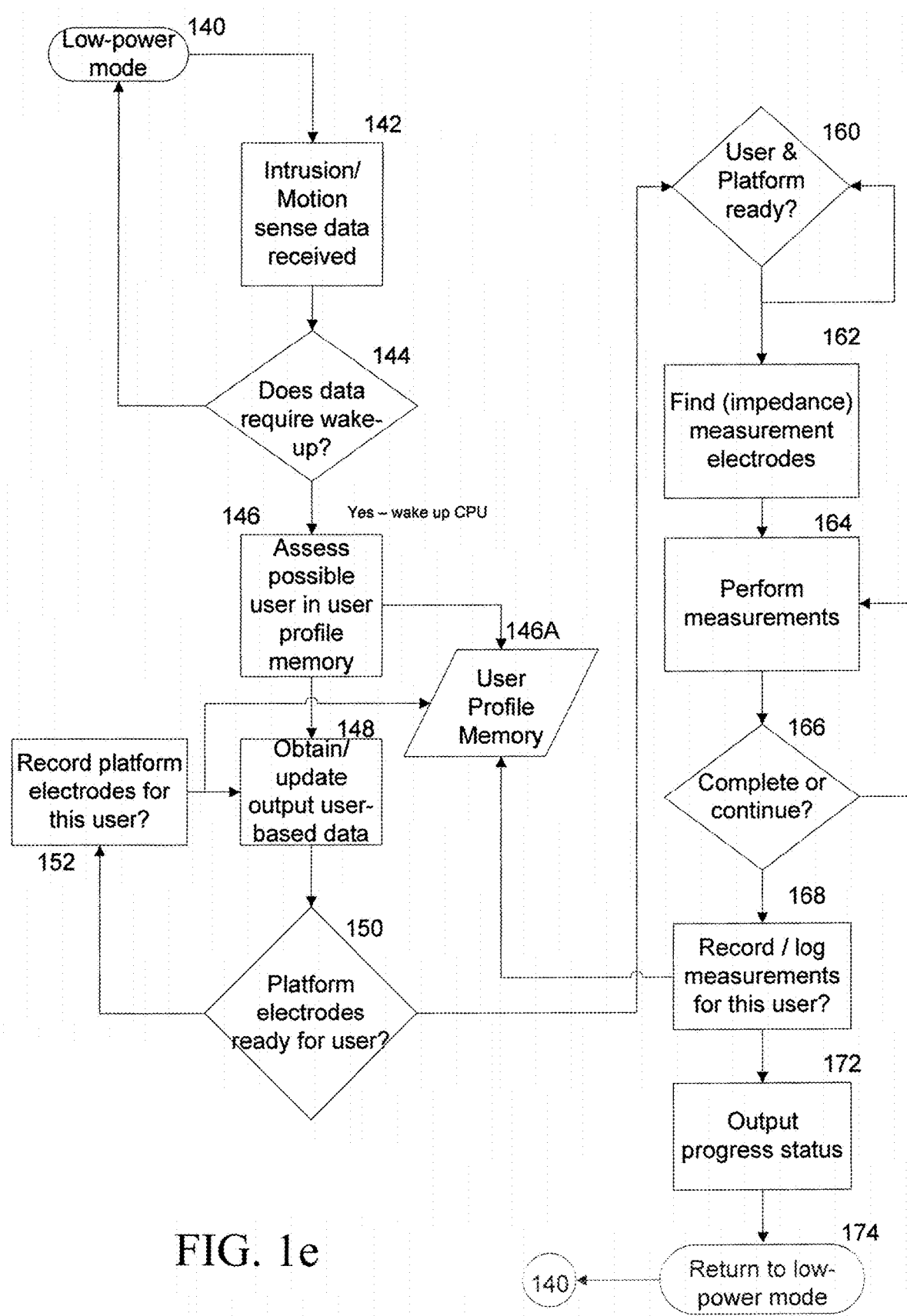
FIG. 1e is a flow chart illustrating an example manner in which a user-specific physiologic meter/scale may be programmed to provide features consistent with aspects of the present disclosure.

FIG. 1e is a flow chart depicting an example manner in which a user-specific physiologic meter or scale may be programmed in accordance with the present disclosure. This flow chart uses a computer processor circuit (or CPU) along with a memory circuit shown herein as user profile memory 146a. The CPU operates in a low-power consumption mode, which may be in off mode or a low-power sleep mode, and at least one other higher power consumption mode of operation.

The CPU can be integrated with presence and/or motion sense circuits, such as a passive infrared (PIR) circuit and/or pyroelectric PIR circuit. In a typical application, the PIR circuit provides a constant flow of data indicative of amounts of radiation sensed in a field of view directed by the PIR circuit. For instance, the PIR circuit can be installed behind an upper surface which is transparent to infrared light (and/or other visible light) of the platform and installed at an angle so that the motion of the user approaching the platform apparatus is sensed. Radiation from the user, upon reaching a certain detectable level, wakes up the CPU which then transitions from the low-power mode, as depicted in block 140, to a regular mode of operation. Alternatively, the low-power mode of operation is transitioned from a response to another remote/wireless input used as a presence to awaken the CPU. In other embodiments, user motion can be detected by an accelerometer integrated in the scale or the motion is sensed with a single integrated microphone or microphone array, to detect the sounds of a user approaching.

Accordingly, from block 140, flow proceeds to block 142 where the user or other intrusion is sensed as data received at the platform apparatus. At block 144, the circuitry assesses whether the received data qualifies as requiring a wake up. If not, flow turns to block 140. If however, wake up is required, flow proceeds from block 144 to block 146 where the CPU assesses whether a possible previous user has approached the platform apparatus. This assessment is performed by the CPU accessing the user profile memory 146A and comparing data stored therein for one or more such previous users with criteria corresponding to the received data that caused the wake up. Such criteria includes, for example, the time of the day, the pace at which the user approached the platform apparatus as sensed by the motion detection circuitry, the height of the user as indicated by the motion sensing circuitry and/or a camera installed and integrated with the CPU, and/or more sophisticated biometric data provided by the user and/or automatically by the circuitry in the platform apparatus.

As discussed herein, such sophisticated circuitry can include one or more of the following user-specific attributes: foot length, type of foot arch, weight of user, and/or manner and speed at which the user steps onto the platform apparatus, or sounds made by the user's motion or by user speech (e.g., voice). In some embodiments, facial or body-feature recognition may also be used in connection with the camera and comparisons of images therefrom to images in the user profile memory.

From block 146, flow proceeds to block 148 where the CPU obtains and/or updates user corresponding data in the user profile memory. As a learning program is developed in the user profile memory, each access and use of the platform apparatus is used to expand on the data and profile for each such user. From block 148, flow proceeds to block 150 where a decision is made regarding whether the set of electrodes at the upper surface of the platform are ready for the user, such as may be based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user has stepped over the user-display. If the electrodes are not ready for the user, flow proceeds from block 150 to block 152 to accommodate this delay.

Once the CPU determines that the electrodes are ready for use while the user is standing on the platform surface, flow proceeds to block 160. Stabilization of the user on the platform surface may be ascertained by injecting current through the electrodes via the interleaved arrangement thereof. Where such current is returned via other electrodes for a particular foot and/or foot size, and is consistent for a relatively brief period of time, for example, a few seconds, the CPU can assume that the user is standing still and ready to use the electrodes and related circuitry. At block 160, a decision is made that both the user and the platform apparatus are ready for measuring impedance and certain segments of the user's body, including at least one foot.

The remaining flow of FIG. 1e includes the application and sensing of current through the electrodes for finding the optimal electrodes (162) and for performing impedance measurements (block 164). These measurements are continued until completed at block 166 and all such useful measurements are recorded and are logged in the user profile memory for this specific user, at block 168. At block 172, the CPU generates output data to provide feedback as to the completion of the measurements and, as can be indicated as a request via the user profile for this user, as an overall report on the progress for the user and relative to previous measurements made for this user has stored in the user profile memory. Such feedback may be shown on the user-display, through a speaker with co-located apertures in the platform for audible reception by the user, and/or by vibration circuitry which, upon vibration under control of the CPU, the user can sense through one or both feet while standing on the scale. From this output at block 172, flow returns to the low power mode as indicated at block 174 with the return to the beginning of the flow at the block 140.

FIG. 2a shows an example of the insensitivity to foot placement 200 on scale electrode pairs 205/210 with multiple excitation paths 220 and sensing current paths 215, consistent with various aspects of the present disclosure. An aspect of the platform is that it has a thickness and strength to support a human adult of at least 200 pounds without fracturing, and another aspect of the device platform is comprised of at least six electrodes, where the first electrode pair 205 is solid and the second electrode pair 210 are interleaved. Another aspect is the first and second interleaved electrode pairs 205/210 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. The resistivity can be below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which can be rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales.

Figure 3A:
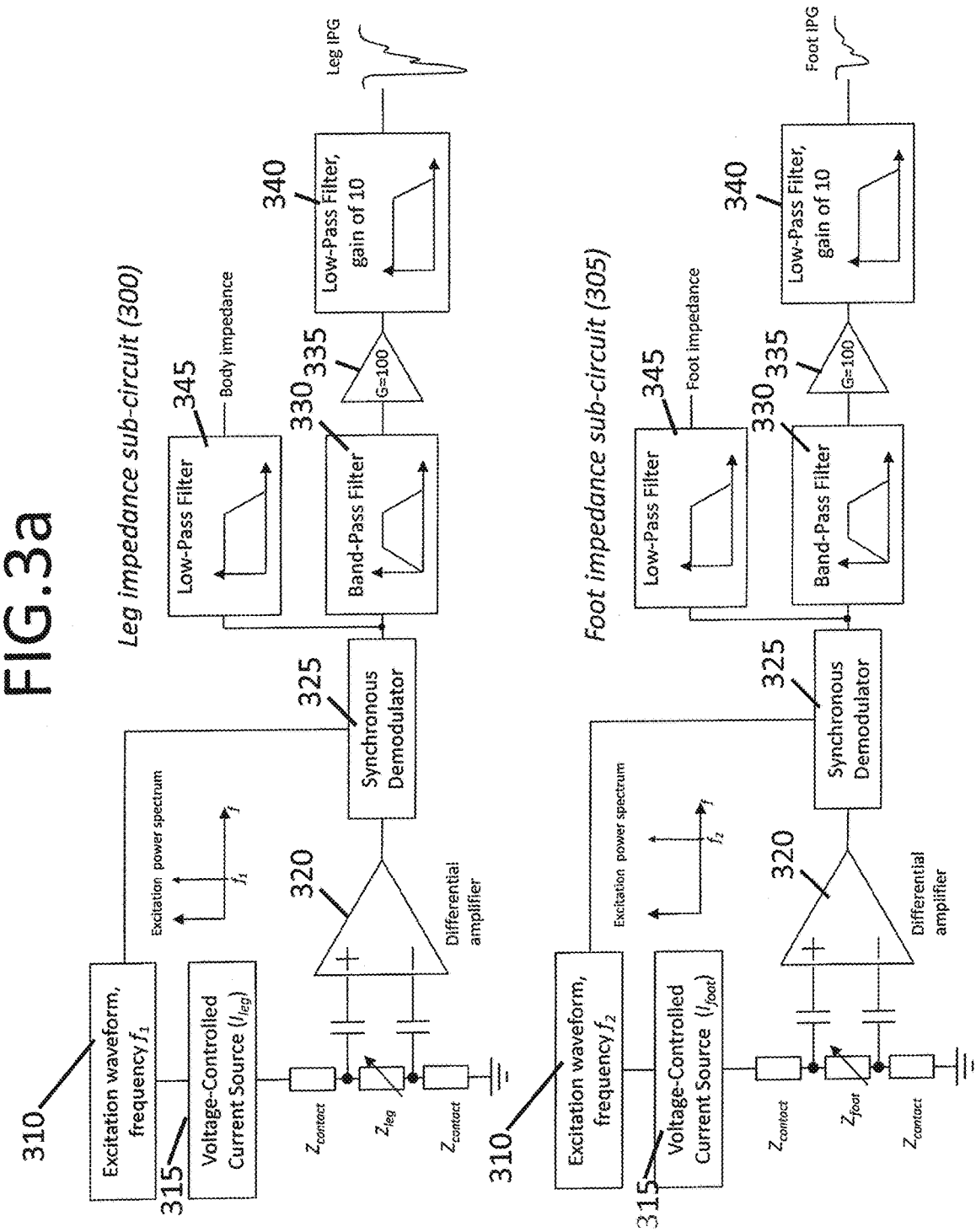
FIGS. 3a-3b show example block diagrams depicting circuitry for sensing and measuring the cardiovascular time-varying IPG raw signals and steps to obtain a filtered IPG waveform, consistent with various aspects of the present disclosure.

In the present disclosure, the leg and foot impedance measurements can be simultaneously carried out using a multi-frequency approach, in which the leg and foot impedances are excited by currents modulated at two or more different frequencies, and the resulting voltages are selectively measured using a synchronous demodulator as shown in FIG. 3a. This homodyning approach can be used to separate signals (in this case, the voltage drop due to the imposed current) with very high accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example. Other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespectively of the foot position, as already explained.

FIG. 2b shows an example of electrode configurations, consistent with various aspects of the disclosure. As shown by the electrode connections, in some embodiments, ground is coupled to the heel of one foot of the user (e.g., the right foot) and the foot current injection (e.g., excitation paths 220) is coupled to the toes of the respective one foot (e.g., toes of the right foot). The leg current injection is coupled to the toes of the other foot (e.g., toes of the left foot).

Figure 2C:
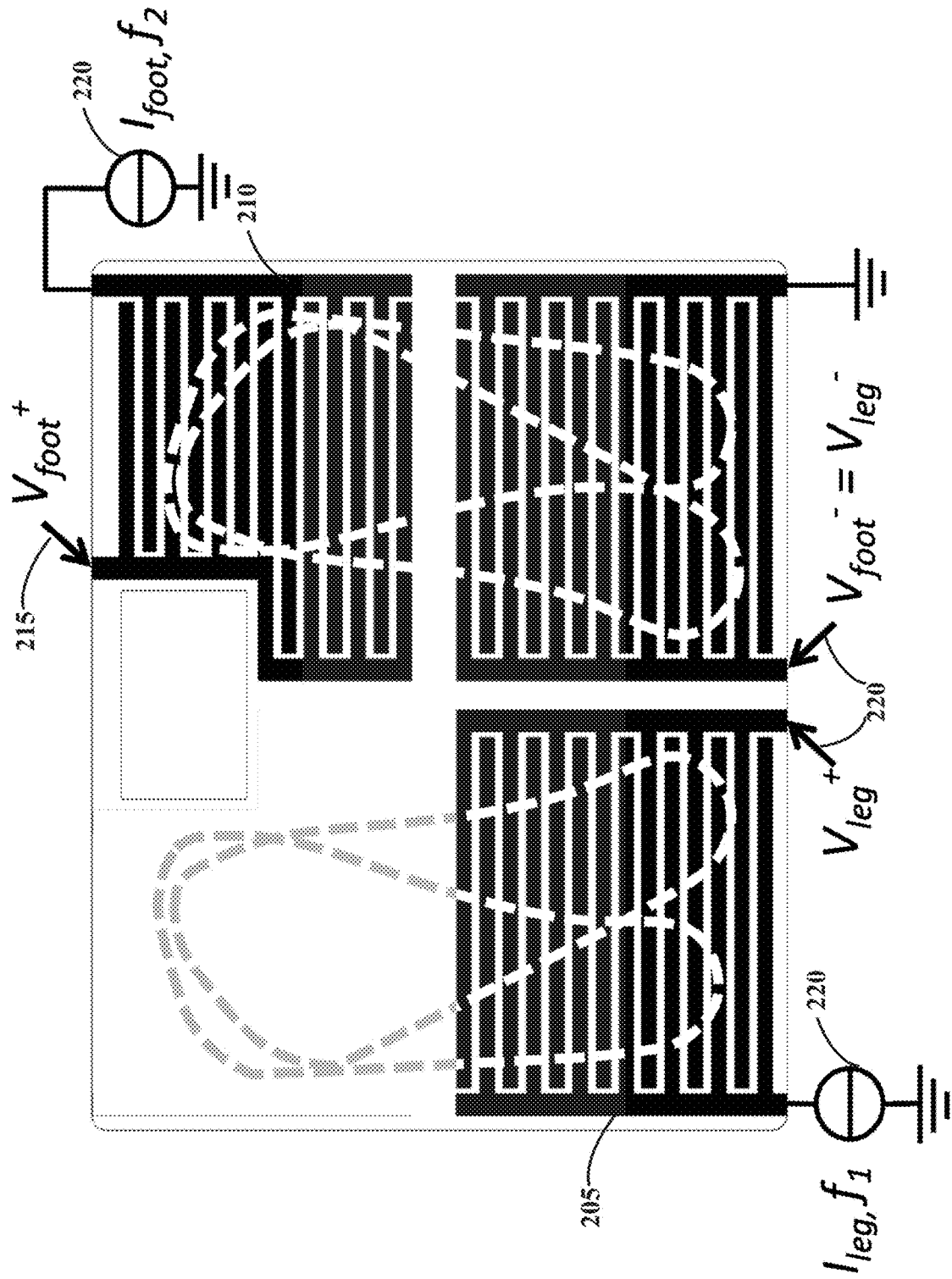

FIG. 2c shows an example of electrode configurations, consistent with various aspects of the disclosure. As shown by the electrode connections, in some embodiments, ground is coupled to the heel of one foot of the user (e.g., the right foot) and the foot current injection (e.g., excitation paths 220) is coupled to the toes of the one foot (e.g., toes of the right foot). The leg current injection is coupled to the heels of the other foot of the user (e.g., heels of the left foot).

Figure 3B:
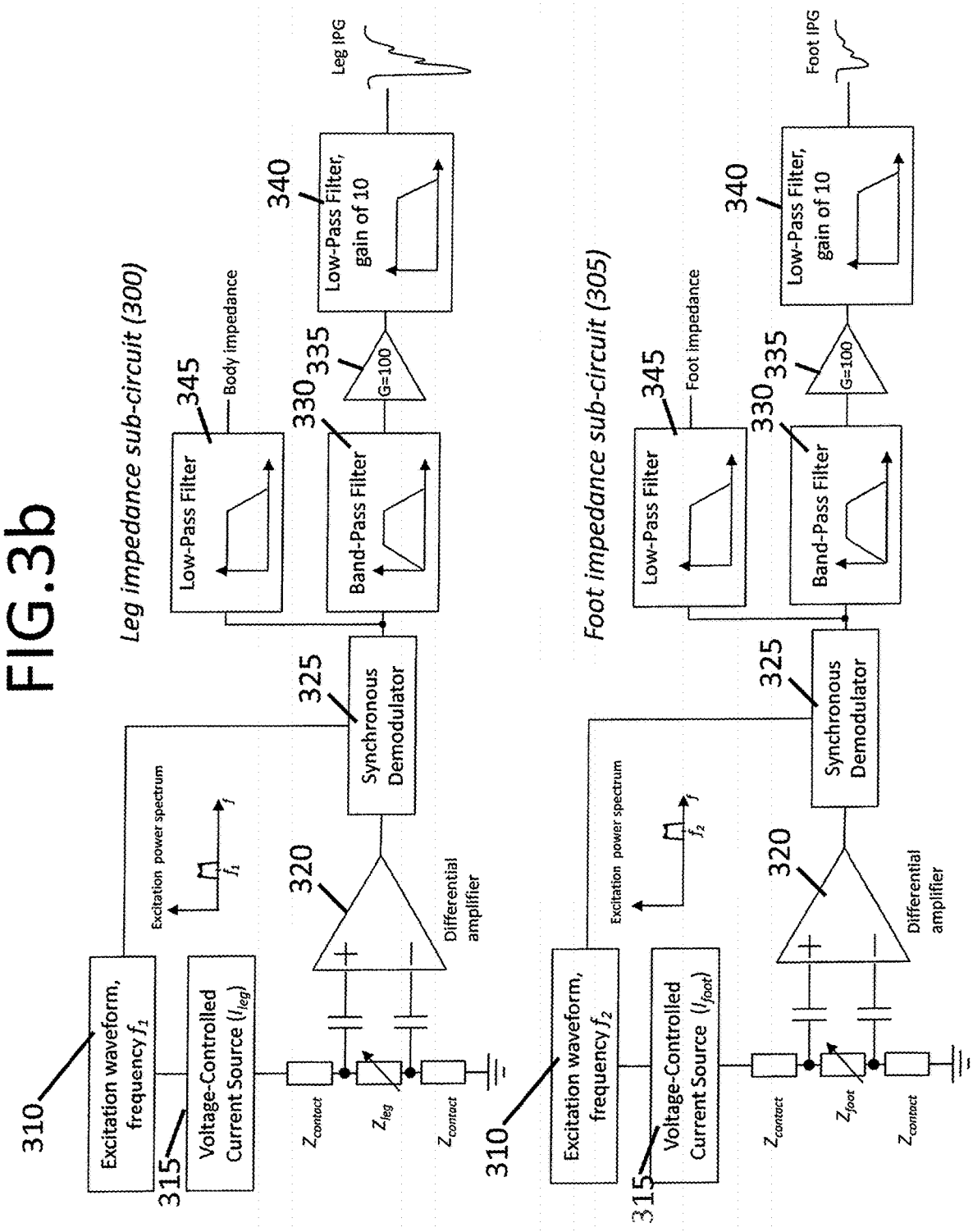

FIGS. 3a-3b show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 3a-3b are separated in to a leg impedance sub-circuit 300 and a foot impedance sub-circuit 305.

Excitation is provided by way of an excitation waveform circuit 310. The excitation waveform circuit 310 provides a stable amplitude excitation signal by way of various wave shapes of various, frequencies, such as more specifically, a sine wave signal (as is shown in FIG. 3a) or, more specifically, a square wave signal (as shown in FIG. 3b). This excitation waveform (of sine, square, or other wave shape) is fed to a voltage-controlled current source circuit 315 which scales the signal to the desired current amplitude. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively.

The voltage drop across the segment of interest (legs or foot) is sensed using an instrumentation differential amplifier (e.g., Analog Devices AD8421) 320. The sense electrodes on the scale are AC-coupled to the inputs of the differential amplifier 320 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet). Alternatively, a fully differential input amplification stage can be used which eliminates the need for DC restoration.

The signal is then demodulated with a phase-sensitive synchronous demodulator circuit 325. The demodulation is achieved in this example by multiplying the signal by 1 or −1 synchronously in-phase with the current excitation. Such alternating gain is provided by an operational amplifier (op amp) and an analog switch (SPST), such as an ADG442 from Analog Devices). More specifically, the signal is connected to both positive and negative inputs through 10 kOhm resistors. The output is connected to the negative input with a 10 kOhm resistor as well, and the switch is connected between the ground and the positive input of the op amp. When open, the gain of the stage is unity. When closed (positive input grounded), the stage acts as an inverting amplifier with a gain of −1. Further, fully differential demodulators can alternatively be used which employ pairs of DPST analog switches whose configuration can provide the benefits of balanced signals and cancellation of charge injection artifacts. Alternatively, other demodulators such as analog multipliers or mixers can be used. The in-phase synchronous detection allows the demodulator to be sensitive to only the real, resistive component of the leg or foot impedance, thereby rejecting any imaginary, capacitive components which may arise from parasitic elements associated with the foot to electrode contacts.

Once demodulated, the signal is band-pass filtered (0.4-80 Hz) with a band-pass filter circuit 330 before being amplified with a gain of 100 with a non-inverting amplifier circuit 335 (e.g., using an LT1058 operational amplifier from Linear Technology Inc.). The amplified signal is further amplified by 10 and low-pass filtered (cut-off at 20 Hz) using a low-pass filter circuit 340 such as 2-pole Sallen-Key filter stage with gain. The signal is then ready for digitization and further processing. In certain embodiments, the signal from the demodulator circuit 325 can be passed through an additional low-pass filter circuit 345 to determine body or foot impedance.

In certain embodiments, the generation of the excitation voltage signal, of appropriate frequency and amplitude, is carried out by a microcontroller, such as an MSP430 (Texas Instruments, Inc.) or a PIC18Fxx series (Microchip Technology, Inc.). The voltage waveform can be generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. In certain embodiments, the generation of the excitation frequency signal can be accomplished by an independent quartz crystal oscillator whose output is frequency divided down by a series of toggle flip-flops (such as an ECS-100AC from ECS International, Inc., and a CD4024 from Texas Instruments, Inc.). In certain embodiments, the generation of the wave shape and frequency can be accomplished by a direct digital synthesis (DDS) integrated circuit (such as an AD9838 from Analog Devices, Inc.). In certain embodiments, the generation of the wave shape (either sine or square) and frequency can be accomplished by a voltage-controlled oscillator (VCO) which is controlled by a digital microcontroller, or which is part of a phase-locked loop (PLL) frequency control circuit. Alternatively, the waveforms and frequencies can be directly generated by on- or off-chip digital-to-analog converters (DACs).

In certain embodiments, the shape of the excitation is not square, but sinusoidal. Such configuration would reduce the requirements on bandwidth and slew rate for the current source and instrumentation amplifier. Harmonics, potentially leading to higher electromagnetic interference (EMI), would also be reduced. Such excitation may also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation could also be more power-efficient. In certain embodiments, the shape of the excitation is not square, but trapezoidal. Alternatively, raised cosine pulses (RCPs) could be used as the excitation wave shape, providing an intermediate between sine and square waves. RCPs could provide higher excitation energy content for a given amplitude, but with greatly reduced higher harmonics.

To further reduce potential electromagnetic interference (EMI), other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). Because of the synchronous demodulation scheme, phase-to-phase variability introduced by spread-spectrum techniques will not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot can be used for standard Body Impedance Analysis (BIA), aiming at extracting the relative content of total water, free-water, fat mass and other body composition measures. Impedance measurements for BIA are typically done at frequencies ranging from kilohertz up to several megahertz. The multi-frequency synchronous detection measurement methods described above can readily be used for such BIA, provided that low-pass filtering (345, FIGS. 3a and 3b) instead of band-pass filtering (330, FIGS. 3a and 3b) is performed following the demodulation. In certain embodiments, a separate demodulator channel may be driven by the quadrature phase of the excitation signal to allow the imaginary component of the body impedance to be extracted in addition to the real component. A more accurate BIA can be achieved by measuring both the real and imaginary components of the impedance. This multi-frequency technique can be combined with traditional sequential measurements used for BIA, in which the impedance is measured at several frequencies sequentially. These measurements are repeated in several body segments for segmental BIAs, using a switch matrix to drive the current into the desired body segments.

Figure 14A:
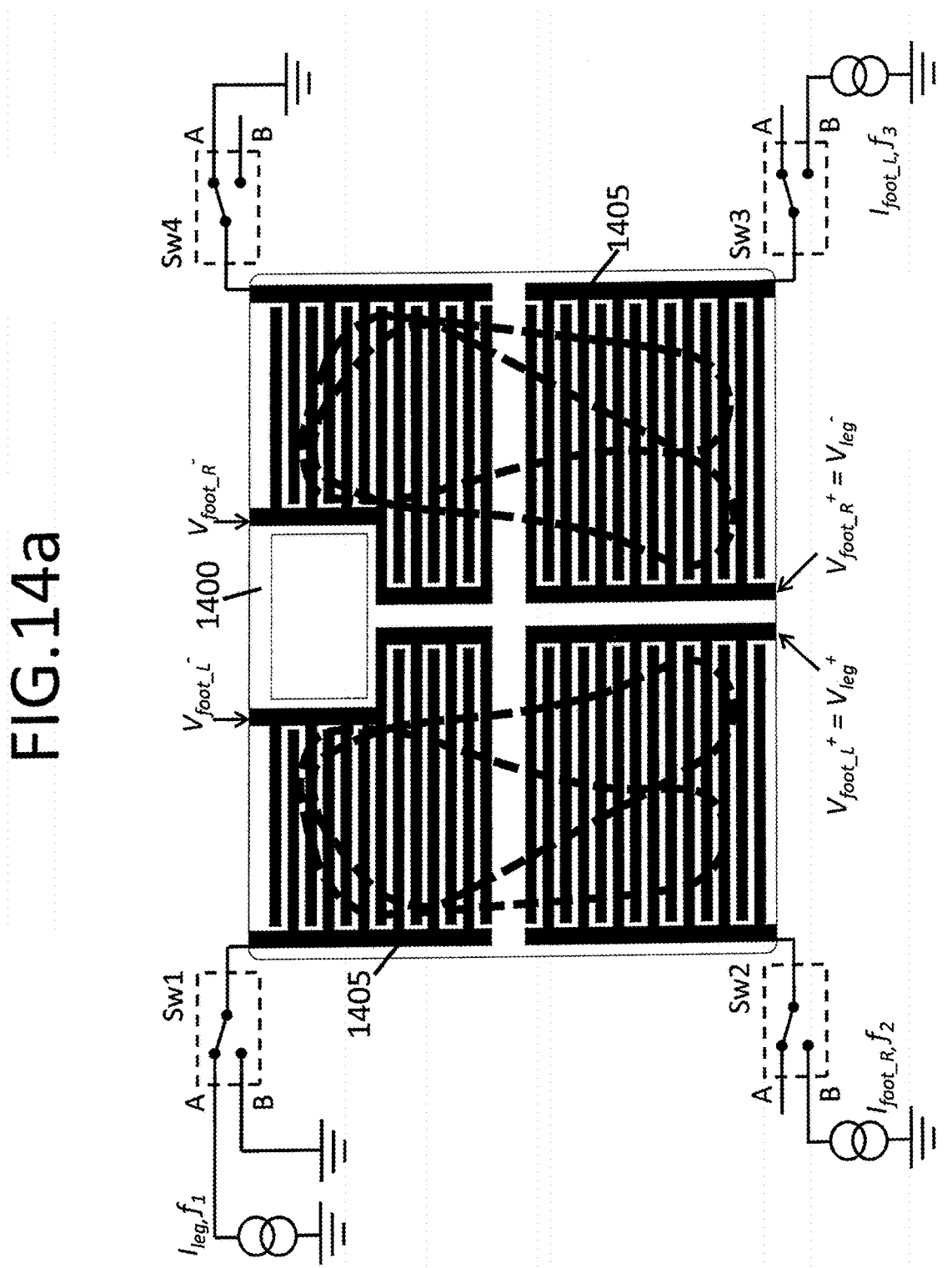
FIG. 14a shows another example of a scale with interleaved foot electrodes to inject and sense current from one foot to another foot, and measure Foot IPG signals in both feet, consistent with various aspects of the present disclosure.

While FIG. 2a shows a circuit and electrode configuration suitable to measure two different segments (legs and one foot), this approach is not readily extendable to more segments due to the shared current return electrode (ground). To overcome this limitation, and provide simultaneous measurements in both feet, the system can be augmented with analog switches to provide time-multiplexing of the impedance measurements in the different segments. This multiplexing can be a one-time sequencing (each segment is measured once), or interleaved at a high-enough frequency that the signal can be simultaneously measured on each segment. The minimum multiplexing rate for proper reconstruction is twice the bandwidth of the measured signal, based on signal processing theory (the Nyquist rate), which equals to about 100 Hz for the impedance signal considered here. The rate must also allow for the signal path to settle in between switching, which usually limits the maximum multiplexing rate. Referring to FIG. 14a, one cycle might start the measurement of the leg impedance and left foot impedances (similarly to previously described, sharing a common return electrode), but then follow with a measurement of the right foot after reconfiguring the switches. For specific information regarding typical switch configurations, reference to U.S. patent application Ser. No. 14/338,266 filed on Oct. 7, 2015, which is fully incorporated for its specific and general teaching of switch configurations.

Since right and left feet are measured sequentially, one should note that a unique current source (at the same frequency) may be used to measure both, providing that the current source is not connected to the two feet simultaneously through the switches, in which case the current would be divided between two paths. One should also note that a fully-sequential measurement, using a single current source (at a single frequency) successively connected to the three different injection electrodes, could be used as well, with the proper switch configuration sequence (no splitting of the current path).

In certain embodiments, the measurement of various body segments, and in particular the legs, right foot and left foot, is achieved simultaneously due to as many floating current sources as segments to be measured, running at separate frequencies so they can individually be demodulated. Such configuration is exemplified in FIG. 14b for three segments (legs, right and left feet). Such configuration has the advantage to provide true simultaneous measurements without the added complexity of time-multiplexing/demultiplexing, and associated switching circuitry. An example of such a floating current source is found in Plickett, et al., Physiological Measurement, 32 (2011). Another approach to floating current sources is the use of transformer-coupled current sources (as depicted in FIG. 14c). Using transformers to inject current into the electrodes enables the use of simpler, grounded-load current sources on the primary, while the electrodes are connected to the secondary. The transformer turns ratio can typically be 1:1, and since frequencies of interest for impedance measurement are typically in the 10-1000 kHz (occasionally 1 kHz for BIA), relatively small pulse transformers can be used. In order to limit the common mode voltage of the body, one of the electrodes in contact with the foot can be grounded.

While certain embodiments presented in the above specification have used current sources for excitation, the excitation can also be performed by a voltage source, where the resulting injection current is monitored by a current sense circuit so that impedance can still be derived by the ratio of the sensed voltage (on the sense electrodes) over the sensed current (injected in the excitation electrodes). It should be noted that broadband spectroscopy methods could also be used for measuring impedances at several frequencies. Combined with time-multiplexing and current switching described above, multi-segment broadband spectroscopy can be achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG.

Figure 3C:
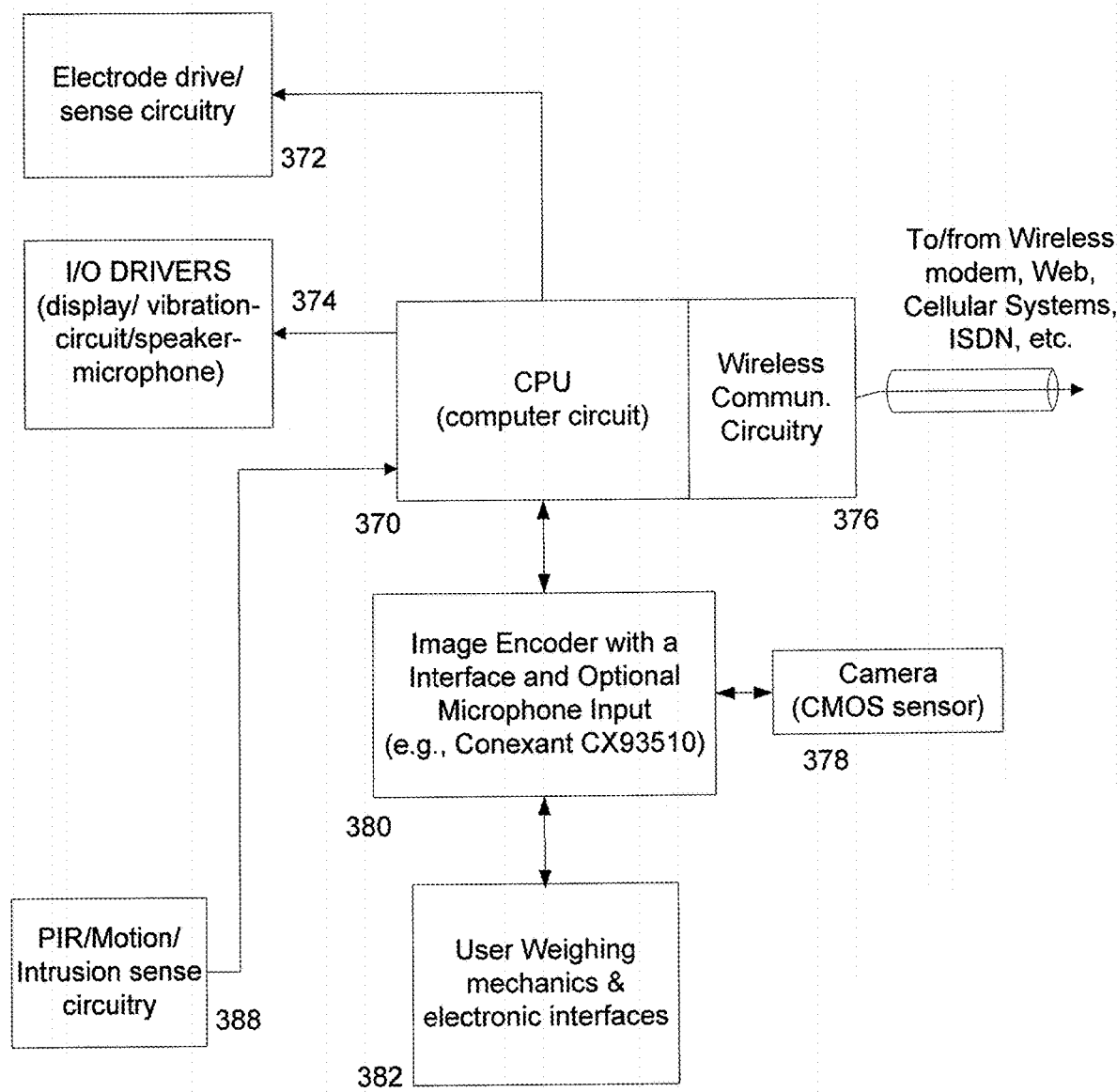
FIG. 3c depicts an example block diagram of circuitry for operating core circuits and modules, including for example those of FIGS. 3a-3b, used in various specific embodiments of the present disclosure.

Consistent with yet further embodiments of the present disclosure, FIG. 3c depicts an example block diagram of circuitry for operating core circuits and modules, including, for example, the operation of the CPU as in FIG. 1a with the related more specific circuit blocks/modules in FIGS. 3A-3B. As shown in the center of FIG. 3c, the computer circuit 370 is shown with other previously-mentioned circuitry in a generalized manner without showing some of the detailed circuitry (e.g., amplification and current injection/sensing (372)). The computer circuit 370 can be used as a control circuit with an internal memory circuit (or as integrated with the memory circuit for the user profile memory 146A of FIG. 1a) for causing, processing and/or receiving sensed input signals as at block 372. As discussed, these sensed signals can be responsive to injection current and/or these signals can be sensed by less complex grid-based sense circuitry surrounding the platform as is convention in capacitive touch-screen surfaces which, in certain embodiments, the platform includes.

As noted, the memory circuit can be used not only for the user profile memory, but also as to provide configuration and/or program code and/or other data such as user-specific data from another authorized source such as from a user monitoring his/her logged data and/or profile from a remote desk-top. The remote device or desk-top can communicate with and access such data via a wireless communication circuit 376. For example, the wireless communication circuit 376 provides an interface between an app on the user's cellular telephone/tablet and the apparatus, wherefrom the IPhone is the output/input interface for the platform (scale) apparatus including, for example, an output display, speaker and/or microphone, and vibration circuitry; each of these I/O aspects and components being discussed herein in connection with other example embodiments.

A camera 378 and image encoder circuit 380 (with compression and related features) can also be incorporated as an option. As discussed above, the weighing scale components, as in block 382, are also optionally included in the housing which encloses and/or surrounds the platform.

For long-lasting battery life in the platform apparatus (batteries not shown), at least the CPU 370, the wireless communication circuit 376, and other current draining circuits are inactive unless and until activated in response to the intrusion/sense circuitry 388. As shown, one specific implementation employs a Conexant chip (e.g., CX93510) to assist in the low-power operation. This type of circuitry is designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) to alleviate the necessity of external memory. The chip uses a simple register set via the microprocessor interface and allows for wide flexibility in terms of compatible operation with another microprocessor.

In one specific embodiment, a method of using the platform with the plurality of electrodes are concurrently contacting a limb of the user, includes operating such to automatically obtain measurement signals from the plurality of electrodes. As noted above, these measurement signals might initially be through less complex (e.g., capacitive grid-type) sense circuitry. Before or while obtaining a plurality of measurement signals by operating the circuitry, the signal-sense circuitry 388 is used to sense wireless-signals indicative of the user approaching the platform and, in response, causing the CPU circuitry 370 to transition from a reduced power-consumption mode of operation and at least one higher power-consumption mode of operation. After the circuitry is operating in the higher power-consumption mode of operation, the CPU accesses the user-corresponding data stored in the memory circuit and causes a plurality of impedance-measurement signals to be obtained by using the plurality of electrodes while they are contacting the user via the platform; therefrom, the CPU generates signals corresponding to cardiovascular timings of the user.

The signal-sense circuit can be employed as a passive infrared detector and with the CPU programmed (as a separate module) to evaluate whether radiation from the passive infrared detector is indicative of a human. For example, sensed levels of radiation that corresponds to a live being, such as a dog, that is less than a three-foot height, and/or has not moved for more than a couple seconds, can be assessed as being a non-human.

Accordingly, as the user is recognized as being human, the CPU is activated and begins to attempt the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU can also select one of a plurality of different types of user-discernible visual/audible/tactile information and for presenting the discerned user with visual/audible/tactile information that was retrieved from the memory as being specific to the user. For example, user-selected visual/audible data can be outputted for the user. Also, responsive to the motion detection indication, the camera can be activated to capture at least one image of the user while the user is approaching the platform (and/or while the user is on the platform to log confirmation of the same user with the measured impedance information). As shown in block 374 of FIG. 3c, where a speaker is also integrated with the CPU, the user can simply command the platform apparatus to start the process and activation proceeds. As previously discussed, the scale can include voice input/output circuitry to receive the user commands via voice commands.

In another method, the circuitry of FIG. 3c is used with the electrodes being interleaved and engaging the user, as a combination weighing scale (via block 382) and a physiologic user-specific impedance-measurement device. By using the impedance-measurement signals and obtaining at least two impedance-measurement signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed in the memory circuit and identified as being specific to the user. This information can be later retrieved by the user, medical and/or security personnel, according to a data-access authorization protocol as might be established upon initial configuration for the user.

Figure 3D:
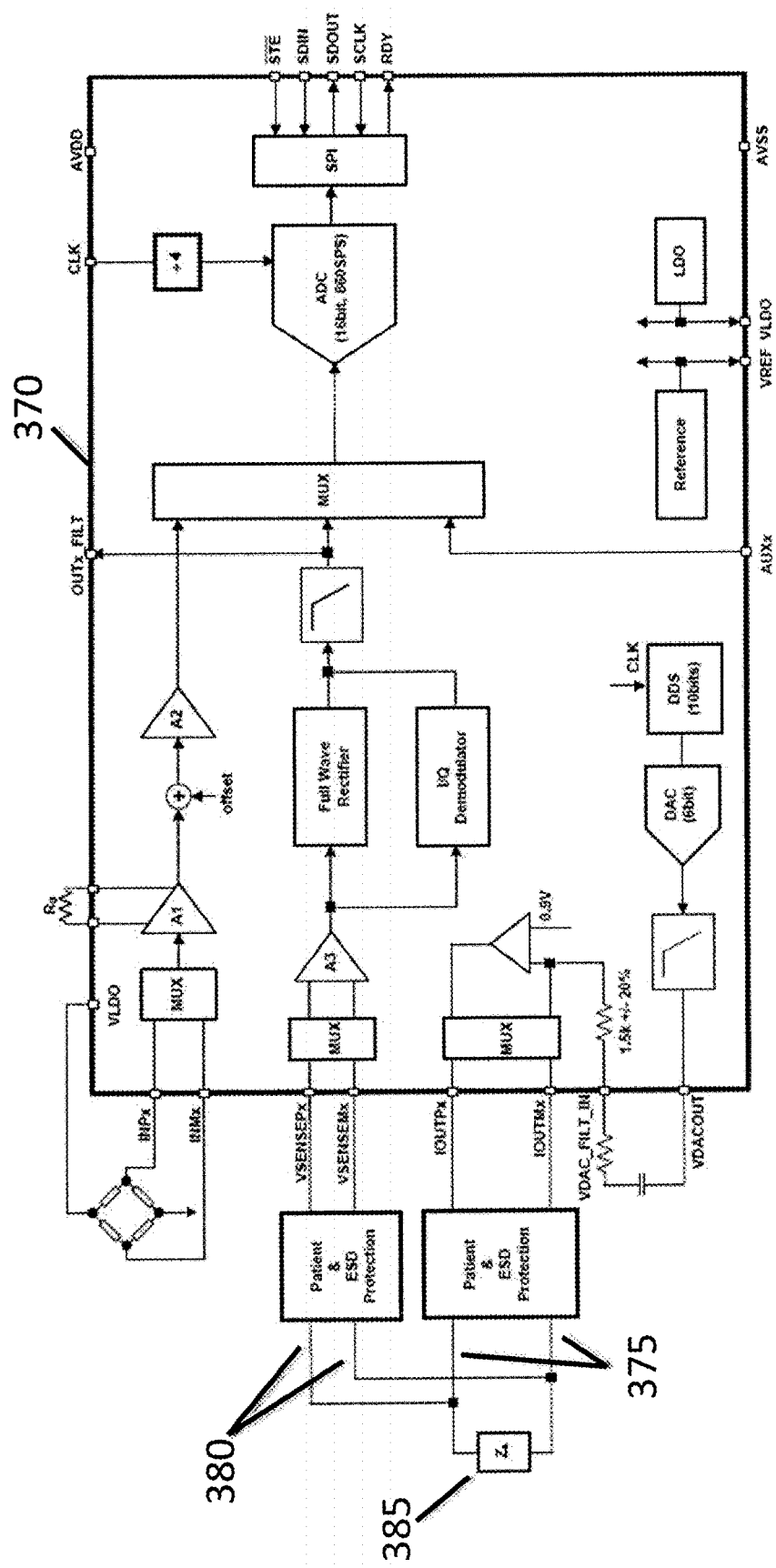
FIG. 3d shows an exemplary block diagram depicting the circuitry for interpreting signals received from electrodes.

FIG. 3d shows an exemplary block diagram depicting the circuitry for interpreting signals received from electrodes (e.g., 372 of FIG. 3c), and/or CPU 370 of FIG. 3c. The input electrodes 375 transmit electrical signals through the patient's body (depending on the desired biometric and physiological test to be conducted) and output electrodes 380 receive the modified signal as affected by a user's electrical impedance 385. Once received by the output electrodes 380, the modified signal is processed by processor circuitry 370 based on the selected test. Signal processing conducted by the processor circuitry 370 is discussed in more detail above (with regard to FIGS. 3a-b). In certain embodiments of the present disclosure, the circuitry within 370 is provided by Texas Instruments part #AFE4300.

Figure 4:
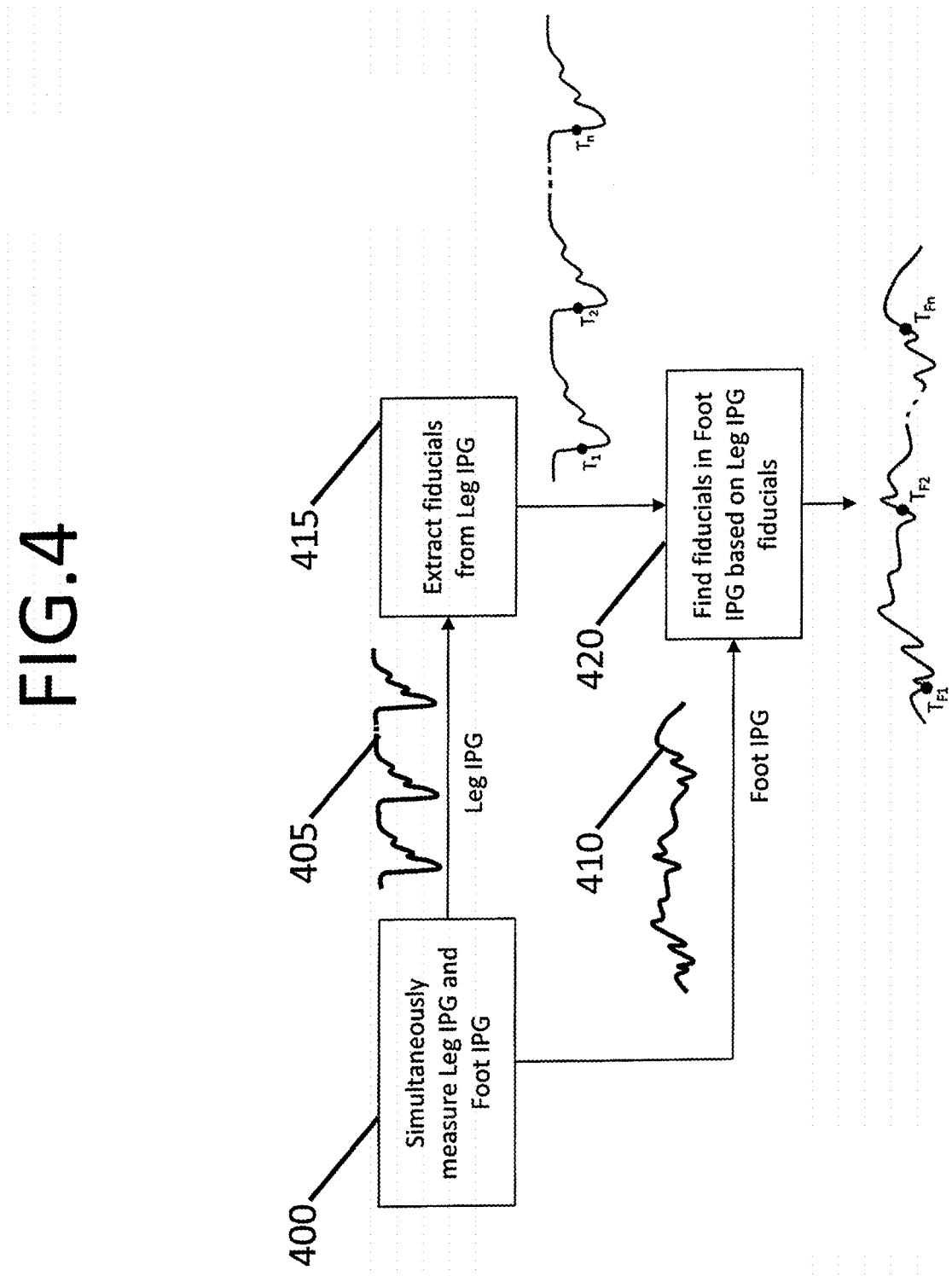
FIG. 4 shows an example block diagram depicting signal processing steps to obtain fiducial references from the individual Leg IPG "beats," which are subsequently used to obtain fiducials in the Foot IPG, consistent with various aspects of the present disclosure.

FIG. 4 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 400, the Leg IP and the Foot IPG are simultaneously measured. As shown at 405, the Leg IPG is low-pass filtered at 20 Hz with an 8-pole Butterworth filter, and inverted so that pulses have an upward peak. The location of the pulses is then determined by taking the derivative of this signal, integrating over a 100 ms moving window, zeroing the negative values, removing the large artifacts by zeroing values beyond 15× the median of the signal, zeroing the values below a threshold defined by the mean of the signal, and then searching for local maxima. Local maxima closer than a defined refractory period of 300 ms to the preceding ones are dismissed. The result is a time series of pulse reference timings.

As is shown in 410, the foot IPG is low-pass filtered at 25 Hz with an 8-pole Butterworth filter and inverted (so that pulses have an upward peak). Segments starting from the timings extracted (415) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is then computed using an intersecting tangent method, where the fiducial (420) is defined by the intersection between a first tangent to the IPG at the point of maximum positive derivative and a second tangent to the minimum of the IPG on the left of the maximum positive derivative within the segment.

The time series resulting from this two-step extraction is used with another signal to facilitate further processing. These timings are used as reference timings to improve the SNR of BCG signals to extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings are extracted, either in Leg IPG or Foot IPG. Following the computation of the SNRs, pulses with a SNR below a threshold value are eliminated from the time series, to prevent propagating noise. The individual SNRs may be computed in a variety of methods known to one skilled in the art. For instance, an estimated pulse can be computed by ensemble averaging segments of signal around the pulse reference timing. The noise associated with each pulse is defined as the difference between the pulse and the estimated pulse. The SNR is the ratio of the root-mean-square (RMS) value of the estimated pulse over the RMS value of the noise for that pulse.

In certain embodiments, the time interval between the Leg IPG pulses, and the Foot IPG pulses, also detected by the above-mentioned methods, is extracted. The Leg IPG measuring a pulse occurring earlier in the legs compared to the pulse from the Foot IPG, the interval between these two is related to the propagation speed in the lower body, i.e., the peripheral vasculature. This provides complementary information to the interval extracted between the BCG and the Foot IPG for instance, and is used to decouple central versus peripheral vascular properties. It is also complementary to information derived from timings between the BCG and the Leg ICG.

Figure 5:
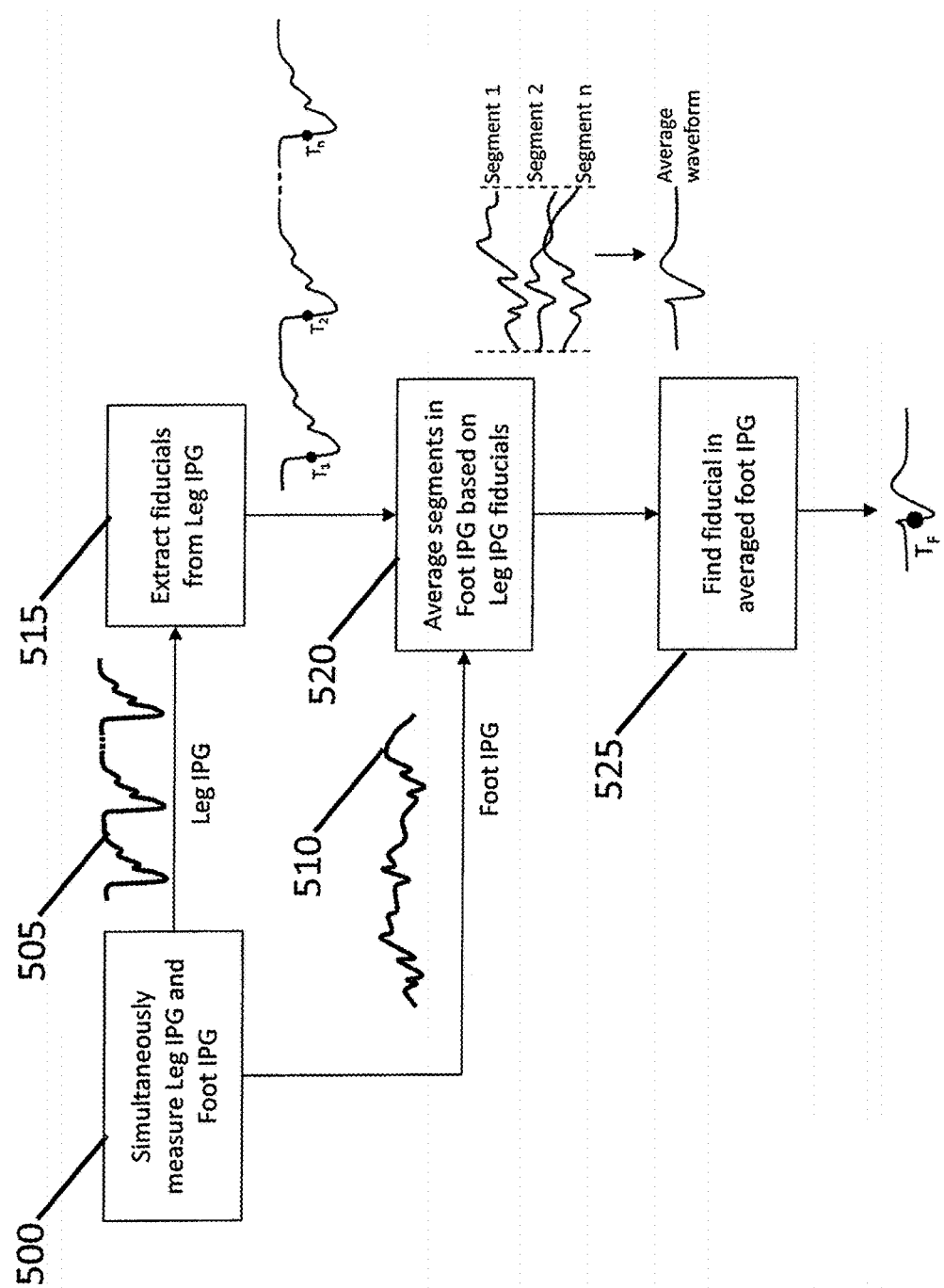
FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure.

FIG. 5 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure. Similar to the method shown in FIG. 4, the Leg IP and the Foot IPG are simultaneously measured (500), the Leg IPG is low-pass filtered (505), the foot IPG is low-pass filtered (510), and segments starting from the timings extracted (515) from the Leg IPG (reference timings). The segments of the Foot IPG extracted based on the Leg IPG timings are ensemble-averaged (520) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise, as shown in FIG. 7b. These timings are used together with timings extracted from the BCG for the purpose of computing the PTT and (PWV). Timings derived from ensemble-averaged waveforms and individual waveforms can also be both extracted, for the purpose of comparison, averaging and error-detection.

Specific timings extracted from the IPG pulses (from either leg or foot) are related (but not limited) to the peak of the pulse, the minimum preceding the peak, or the maximum second derivative (maximum rate of acceleration) preceding the point of maximum derivative. An IPG pulse and the extraction of a fiducial (525) in the IPG can be performed by other signal processing methods, including (but not limited to) template matching, cross-correlation, wavelet-decomposition, or short window Fourier transform.

FIG. 6a shows examples of the Leg IPG signal with fiducials (plot 600); the segmented Leg IPG into beats (plot 605); and the ensemble-averaged Leg IPG beat with fiducials and calculated SNR (plot 610), for an exemplary high-quality recording, consistent with various aspects of the present disclosure. FIG. 6b shows examples of the Foot IPG signal with fiducials derived from the Leg IPG fiducials (plot 600); the segmented Foot IPG into beats (plot 605); and the ensemble-averaged Foot IPG beat with fiducials and calculated SNR (plot 610), for an exemplary high-quality recording, consistent with various aspects of the present disclosure. FIG. 7a shows examples of the Leg IPG signal with fiducials (plot 700); the segmented Leg IPG into beats (plot 705); and the ensemble averaged Leg IPG beat with fiducials and calculated SNR (plot 710), for an exemplary low-quality recording, consistent with various aspects of the present disclosure. FIG. 7b shows examples of the Foot IPG signal with fiducials derived from the Leg IPG fiducials (plot 700); the segmented Foot IPG into beats (plot 705); and the ensemble-averaged Foot IPG beat with fiducials and calculated SNR (plot 710), for an exemplary low-quality recording, consistent with aspects of the present disclosure.

FIG. 8 shows an example correlation plot 800 for the reliability in obtaining the low SNR Foot IPG pulse for a 30-second recording, using the first impedance signal as the trigger pulse, from a study including 61 test subjects with various heart rates, consistent with various aspects of the present disclosure.

In certain embodiments, a dual-Foot IPG is measured, allowing the detection of blood pressure pulses in both feet. Such information can be used for diagnostic of peripheral arterial diseases (PAD) by comparing the relative PATs in both feet to look for asymmetries. It can also increase the robustness of the measurement by allowing one foot to have poor contact with electrodes (or no contact at all). SNR measurements can be used to assess the quality of the signal in each foot, and to select the best one for downstream analysis. Timings extracted from each foot can be compared and set to flag potentially inaccurate PWV measurements due to arterial peripheral disease, in the event these timings are different by more than a threshold. Alternatively, timings from both feet are pooled to increase the overall SNR if their difference is below the threshold.

In certain embodiments, the disclosure is used to measure a PWV, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

FIGS. 9a-b show example configurations to obtain the PTT, using the first IPG as the triggering pulse for the Foot IPG and BCG, consistent with various aspects of the present disclosure. The I-wave of the BCG 900 normally depicts the headward force due to cardiac ejection of blood into the ascending aorta which is used as a timing fiducial indicative of the pressure pulse initiation of the user's proximal aorta relative to the user's heart. The J-wave is indicative of timings in the systole phase and also incorporates information related to the strength of cardiac ejection and the ejection duration. The K-Wave provides systolic and vascular information of the user's aorta. The characteristic timings of these and other BCG waves are used as fiducials that can be related to fiducials of the IPG signals of the present disclosure. FIG. 10 shows nomenclature and relationships of various cardiovascular timings, consistent with various aspects of the present disclosure.

Figure 11:
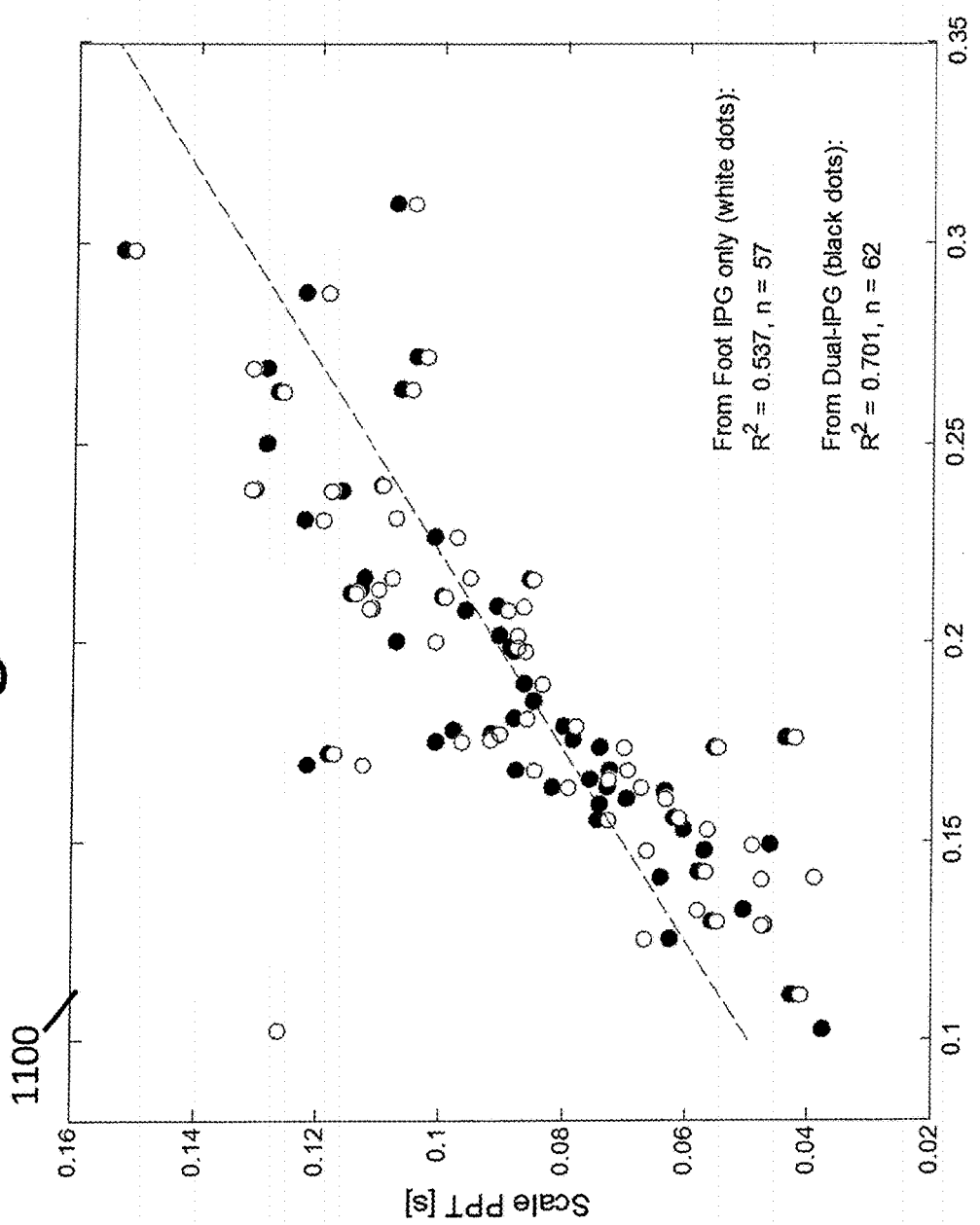
FIG. 11 shows an example graph of PTT correlations for two detection methods (white dots) Foot IPG only, and (black dots) Dual-IPG method, consistent with various aspects of the present disclosure.
Figure 12:
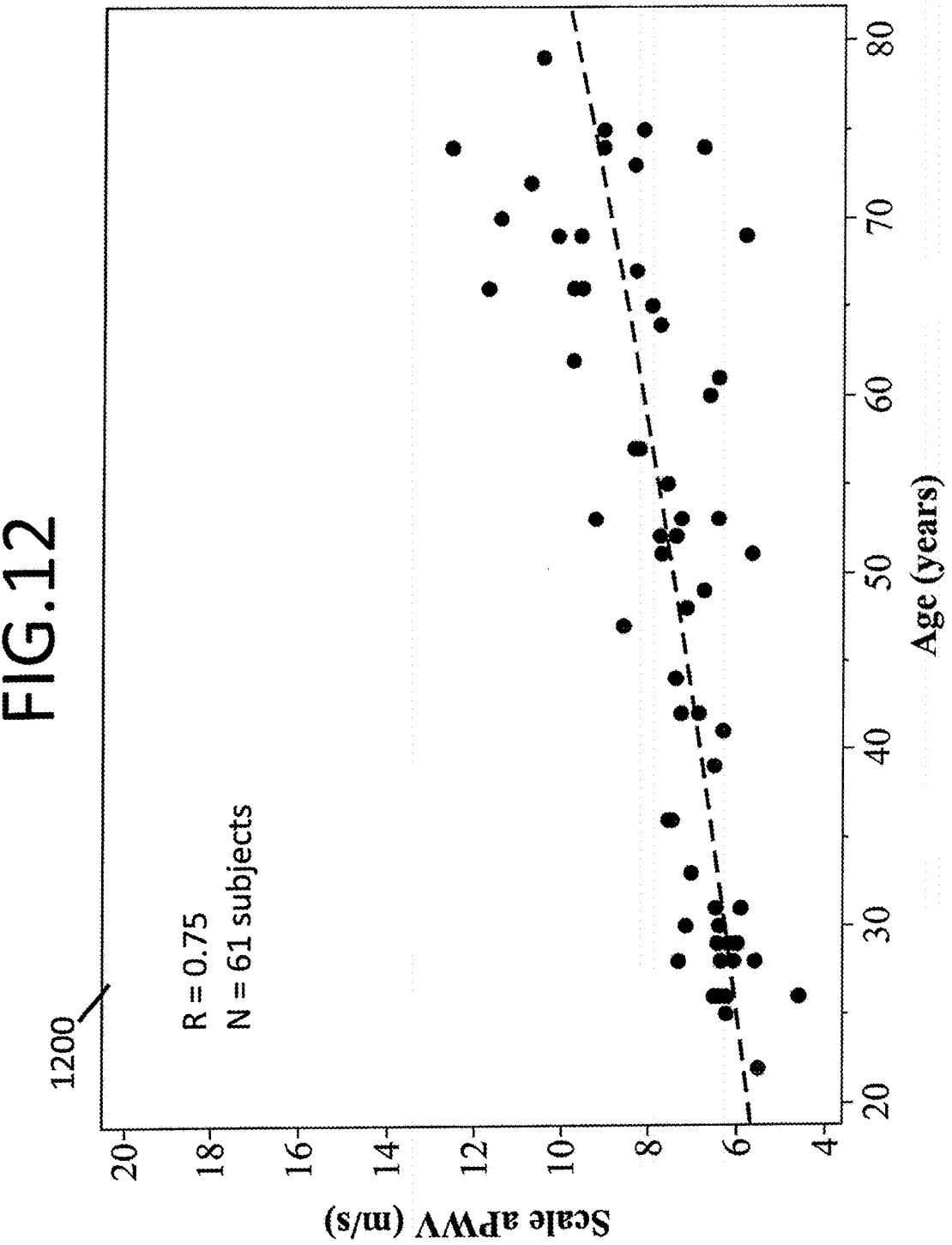
FIG. 12 shows an example graph of pulse wave velocity (PWV) obtained from the present disclosure compared to the ages of 61 human test subjects, consistent with various aspects of the present disclosure.

FIG. 11 shows an example graph 1100 of PTT correlations for two detection methods (white dots) Foot IPG only, and (black dots) Dual-IPG method; and FIG. 12 shows an example graph 1200 of PWV obtained from the present disclosure compared to the ages of 61 human test subjects, consistent with various aspects of the present disclosure.

Figure 13:
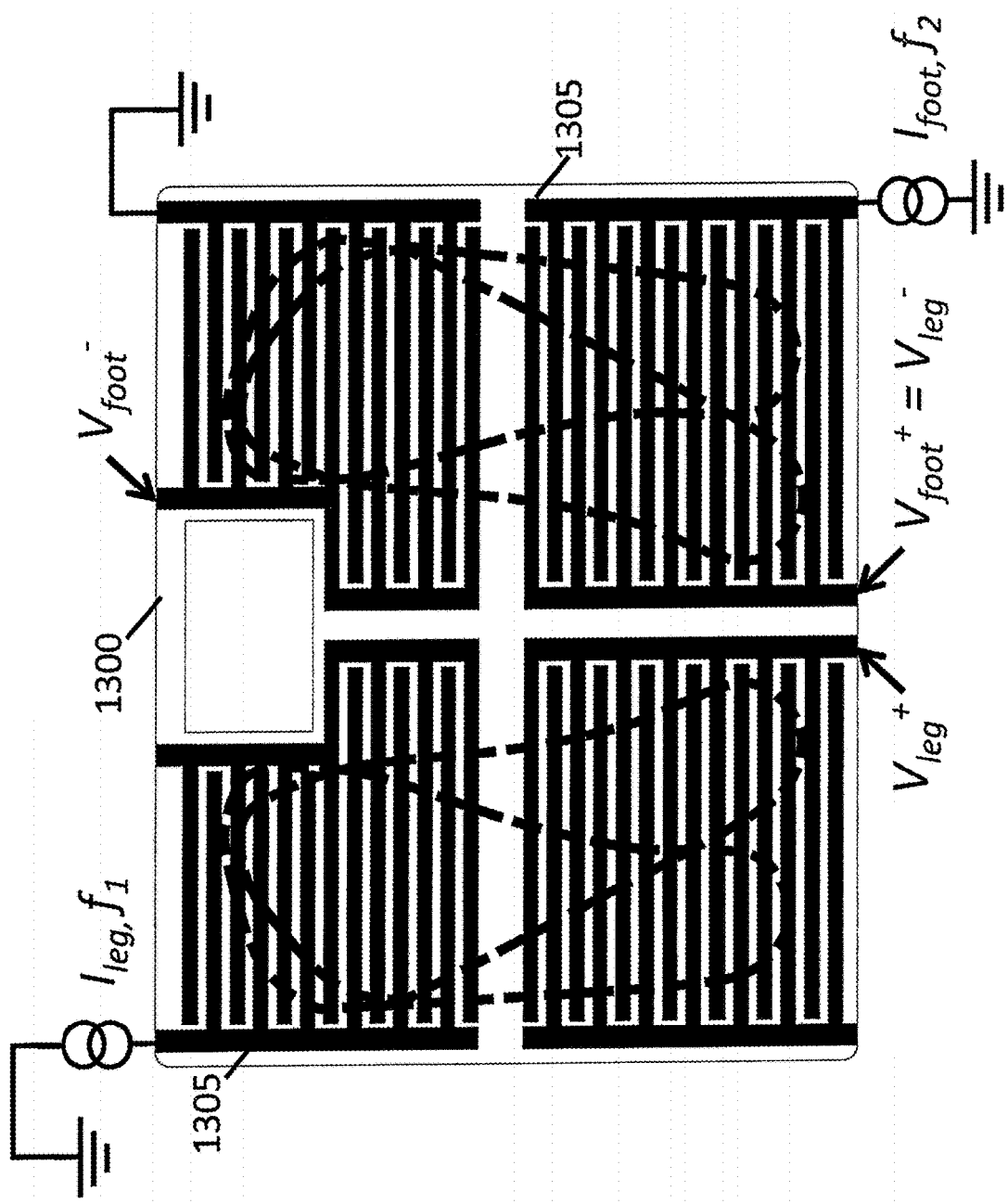
FIG. 13 shows another example of a scale with interleaved foot electrodes to inject and sense current from one foot to another foot, and within one foot, consistent with various aspects of the present disclosure.

FIG. 13 shows an example of a scale 1300 with integrated foot electrodes 1305 to inject and sense current from one foot to another foot, and within one foot.

FIG. 14a-c shows various examples of a scale 1400 with interleaved foot electrodes 1405 to inject/sense current from one foot to another foot, and measure Foot IPG signals in both feet.

FIGS. 15a-d shows an example breakdown of a scale 1500 with interleaved foot electrodes 1505 to inject and sense current from one foot to another foot, and within one foot.

Figure 16:
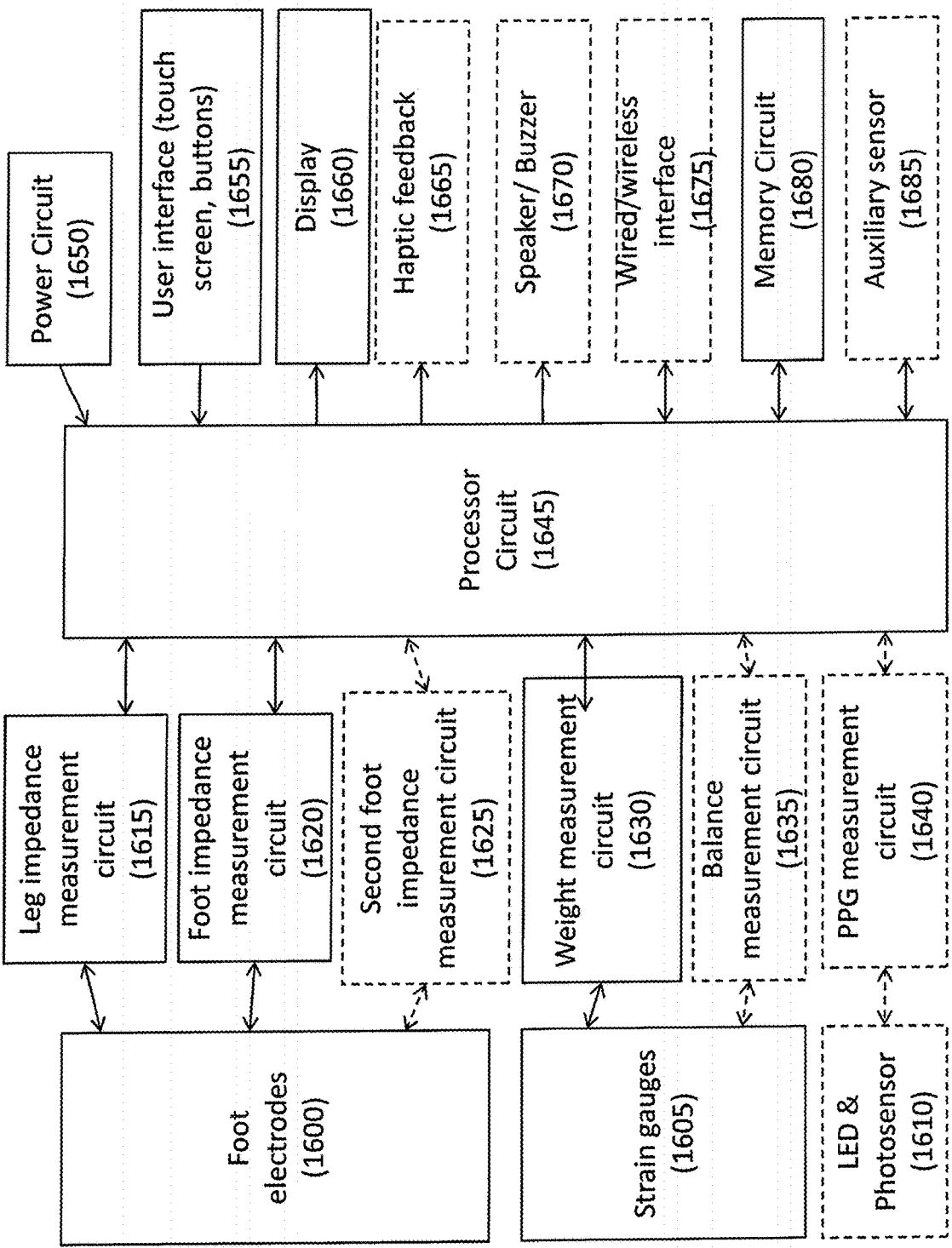
FIG. 16 shows an example block diagram of circuit-based building blocks, consistent with various aspects of the present disclosure.

FIG. 16 shows an example block diagram of circuit-based building blocks, consistent with various aspects of the present disclosure. The various circuit-based building blocks shown in FIG. 16 can be implemented in connection with the various aspects discussed herein. In the example shown, the block diagram includes foot electrodes 1600 that can collect the IPG signals. Further, the block diagram includes strain gauges 1605, and an LED/photosensor 1610. The foot electrodes 1600 is configured with a leg impedance measurement circuit 1615, a foot impedance measurement circuit 1620, and an optional second foot impedance measurement circuit 1625. The leg impedance measurement circuit 1615, the foot impedance measurement circuit 1620, and the optional second foot impedance measurement circuit 1625 report the measurements collected to a processor circuitry 1645.

The processor circuitry 1645 collects data from a weight measurement circuit 1630 and an optional balance measurement circuit 1635 that are configured with the strain gauges 1605. Further, an optional photoplethysmogram (PPG) measurement circuit 1640, which collects data from the LED/photosensor 1610, provides data to the processor circuitry 1645.

The processor circuitry 1645 is powered via a power circuit 1650. Further, the processor circuitry 1645 collects user input data from a user interface 1655 (e.g., iPad®, smart phone and/or other remote user handy/CPU with a touch screen and/or buttons). The data collected/measured by the processor circuitry 1645 is shown to the user via a display 1660. Additionally, the data collected/measured by the processor circuitry 1645 can be stored in a memory circuit 1680. Further, the processor circuitry 1645 can optionally control a haptic feedback circuit 1665, a speaker or buzzer 1670, a wired/wireless interface 1675, and an auxiliary sensor 1685 for one-way or two-way communication between the scale and the user.

Figure 17:
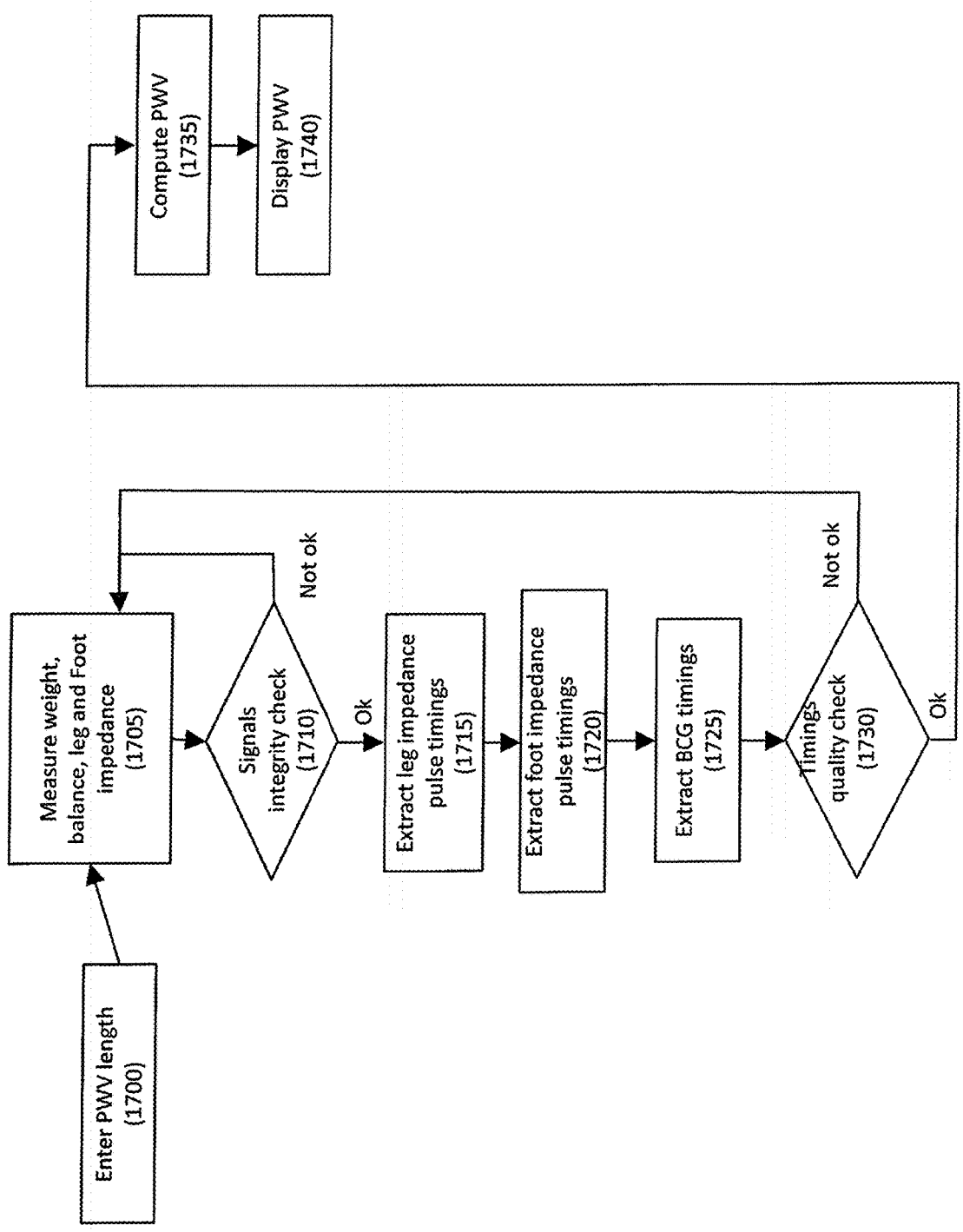
FIG. 17 shows an example flow diagram, consistent with various aspects of the present disclosure.

FIG. 17 shows an example flow diagram, consistent with various aspects of the present disclosure. At block 1700, a PWV length is entered. At block 1705, a user's weight, balance, leg, and foot impedance are measured. At 1710, the integrity of signals is checked (e.g., SNR). If the signal integrity check is not met, the user's weight, balance, leg, and foot impedance are measured again (block 1705), if the signals integrity check is met, the leg impedance pulse timings are extracted (as is shown at block 1715). At block 1720, foot impedance and pulse timings are extracted, and at block 1725, BCG timings are extracted. At block 1730, a timings quality check is performed. If the timings quality check is not validated, the user's weight, balance, leg and foot impedance are again measured (block 1705). If the timings quality check is validated, the PWV is calculated (as is shown at block 1735). At block 1740, the PWV is displayed to the user.

Figure 18:
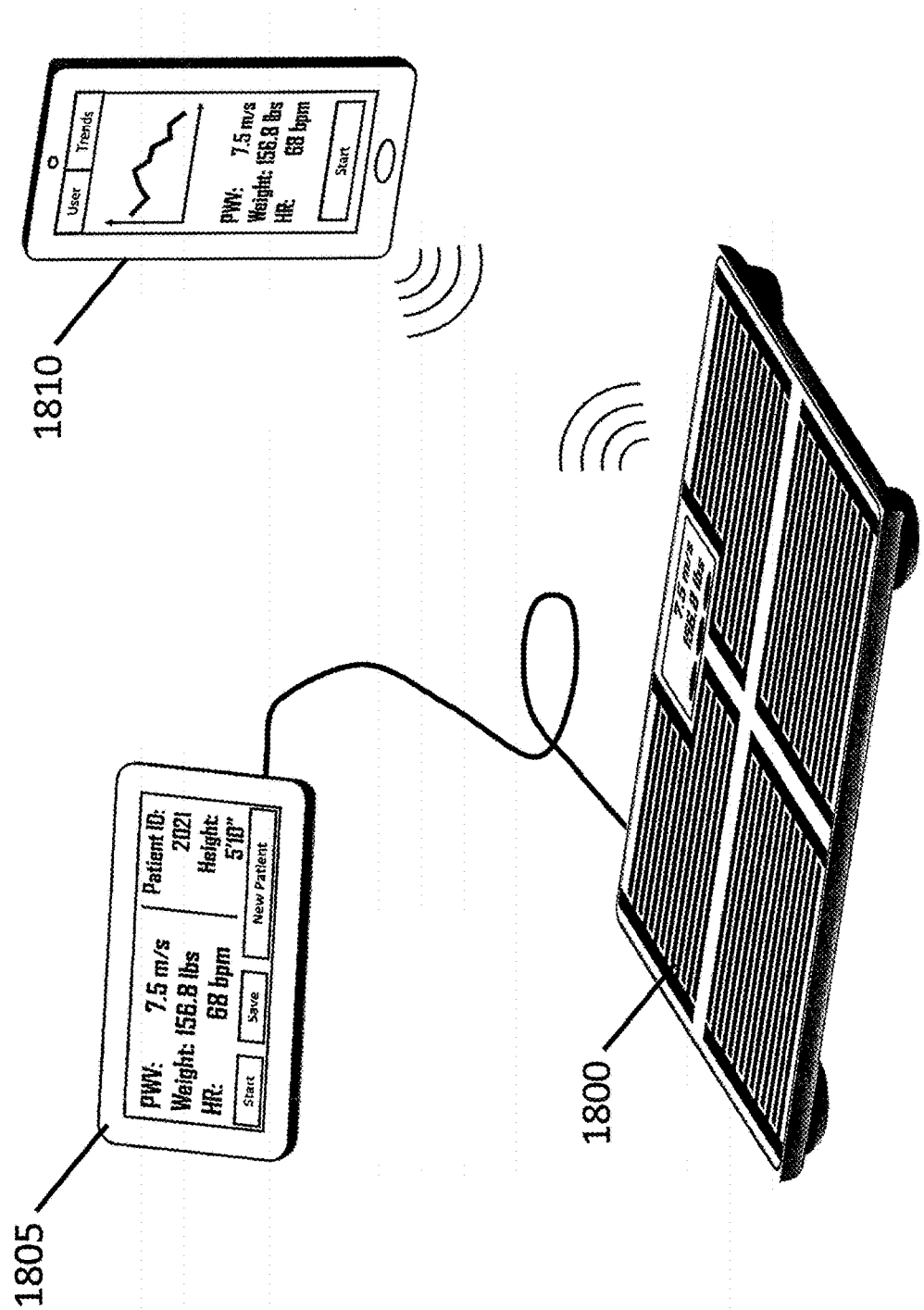
FIG. 18 shows an example scale communicatively coupled to a wireless device, consistent with various aspects of the present disclosure.

FIG. 18 shows an example scale 1800 communicatively coupled to a wireless device, consistent with various aspects of the present disclosure. As described herein, a display 1805 displays the various aspects measured by the scale 1800. The scale can also wirelessly broadcast the measurements to a wireless device 1810. The wireless device 1810 can also be implemented as an iPad®, smart phone or other CPU to provide input data for configuring and operating the scale.

As an alternative or complementary user interface, the scale can include a FUI which can be enabled/implementable by one or more foot-based biometrics (for example, with the user being correlated to previously-entered user weight, and/or foot size/shape). The user foot-based biometric can also be implemented by the user manually entering data (e.g., a password) on the upper surface or display area of the scale. In implementations in which the scale is configured with a haptic, capacitive or flexible pressure-sensing upper surface, the (upper surface/tapping) touching from or by the user is sensed in the region of the surface and processed according to conventional X-Y grid Signal processing in the logic circuitry/CPU that is within the scale. By using one or more of the accelerometers located within the scale at its corners, such user data entry can be sensed by each such accelerometer so long as the user's toe, heel or foot pressure associated with each tap provides sufficient force. Although the present discussion refers to a FUI, embodiments are not so limited. Various embodiments include internal or external GUIs that are in communication with the scale and used to obtain a biometric and that can be in place of the FUI and/or in combination with a FUI. For example, a user device having a GUI, such as tablet, is in communication with the scale via a wired or wireless connection. The user device obtains a biometric, such a finger print, and communicates the biometric to the scale.

In various embodiments, the above discussed user-interface can be used with other features described herein for the purpose of storing and securing user data that is sensitive to the user such as: the configuration data input by the user, the biometric and/or passwords entered by the user, and the user-specific health related data which might include less sensitive data (e.g., the user's weight) and more sensitive data (e.g., the user's scale obtains cardiograms and other data generated by or provided to the scale and associated with the user's symptoms and/or diagnoses). For such user data, the above described biometrics are used as directed by the user for indicating and defining protocol to permit such data to be exported from the scale to other remote devices indoor locations. In more specific embodiments, the scale operates in different modes of data security including, for example: a default mode in which the user's body mass and/or weight is displayed regardless of any biometric which would associate with the specific user standing on the scale; another mode in which complicated data (or data reviewed infrequently) is only exported from the scale under specific manual commands provided to the scale under specific protocols; and another mode or modes in which the user-specific data that is collected from the scale is processed and accessed based on the type of data. Such data categories include categories of different level of importance and/or sensitivities such as the above-discussed high and low level data and other data that might be very specific to a symptom and/or degrees of likelihood for diagnoses. Optionally, the CPU in the scale is also configured to provide encryption of various levels of the user's sensitive data.

FIGS. 19*a-c* show example impedance as measured through different parts of the foot based on the foot position, consistent with various aspects of the present disclosure. For instance, example impedance measurement configurations may be implemented using a dynamic electrode configuration for measurement of foot impedance and related timings. Dynamic electrode configuration may be implemented using independently-configurable electrodes to optimize the impedance measurement. As shown in FIG. 19*a*, interleaved electrodes 1900 are connected to an impedance processor circuit 1905 to determine foot length, foot position, and/or foot impedance. As is shown in FIG. 19*b*, an impedance measurement is determined regardless of foot position 1910 based on measurement of the placement of the foot across the electrodes 1900. This is based in part in the electrodes 1900 that are engaged (blackened) and in contact with the foot (based on the foot position 1910), which is shown in FIG. 19*c*.

More specifically regarding FIG. 19*a*, configuration includes connection/de-connection of the individual electrodes 1900 to the impedance processor circuit 1905, their configuration as current-carrying electrodes (injection or return), sense electrodes (positive or negative), or both. The configuration is preset based on user information, or updated at each measurement (dynamic reconfiguration) to optimize a given parameter (impedance SNR, measurement location). The system algorithmically determines which electrodes under the foot to use in order to obtain the highest SNR in the pulse impedance signal. Such optimization algorithm may include iteratively switching configurations and measuring the impedance, and selecting the best suited configuration. Alternatively, the system first, through a sequential impedance measurement between each individual electrode 1900 and another electrode in contact with the body (such as an electrode in electrode pair 205 on the other foot), determine which electrodes are in contact with the foot. By determining the two most apart electrodes, the foot size is determined. Heel location can be determined in this manner, as can other characteristics such as foot arch type. These parameters are used to determine programmatically (in an automated manner by CPU/logic circuitry) which electrodes are selected for current injection and return (and sensing if a Kelvin connection issued) to obtain the best foot IPG.

In various embodiments involving the dynamically reconfigurable electrode array 1900/1905, an electrode array set is selected to measure the same portion/segment of the foot, irrespective of the foot location on the array. FIG. 19*b* illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume/segment of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) can introduce an error in the calculation of the interval. With respect to FIG. 19*b*, the timing of the peak of the IPG from the foot placement on the right (sensing the toe/plantar region) is later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 19*c* shows an example embodiment involving dynamic reconfiguration of the electrodes to reduce such foot placement-induced variations. As an example, by sensing the location of the heel first (as described above), it is possible to activate a subset of electrodes under the heel, and another subset of electrodes separated by a fixed distance (1900). The other electrodes (e.g., unused electrodes) are left disconnected. The sensed volume will therefore be the same, producing consistent timings. The electrode configuration leading to the most consistent results may be informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale).

In certain embodiments, the apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary because the user placed the one foot at a slightly different position on the platform or scale. In FIG. 19*a*, the foot-to-electrode locations for the heel are different locations than that shown in FIGS. 19*b* and 19*c*. As this different foot placement can occur from day to day for the user, the timing and related impedance measurements are for the same (internal) segment of the foot. By having the processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system can be used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments may be suitable for determining the arterial stiffness (or arterial compliance) and/or cardiovascular risk of the user regardless of the position of the user's feet within the bounds of the interleaved electrodes. In certain embodiments, the weighing scale system incorporated the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are stored in the memory on the scale and displayed to the user via a display on the scale, audible communication from the scale, and/or the data is communicated to a peripheral device such as a computer, smart phone, tablet computing device. The communication occurs to the peripheral device with a wired connection, or can be sent to the peripheral device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contacts feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

Various embodiments are implemented in accordance with, and fully incorporating by reference for their general teachings, the above-identified PCT Applications and U.S. Provisional Applications (including PCT Ser. No. PCT/US2016/062484 and PCT Ser. No. PCT/US2016/062505), which teachings are also incorporated by reference specifically concerning physiological scales and related measurements and communications such as exemplified by disclosure in connection with FIGS. 1a, 1b, 1e, 1f, and 2b-e in PCT Ser. No. PCT/US2016/062484 and FIGS. 1a, 1k, and 1m in PCT. Ser. No. PCT/US2016/062505, and related disclosure in the above-identified U.S. Provisional Applications. For example, above-identified U.S. Provisional Application (Ser. No. 62/258,238), which teachings are also incorporated by reference specifically concerning obtaining derivation data, assessing a condition or treatment of the user, and drug titration features and aspects as exemplified by disclosure in connection with FIGS. 1a-1b of the underlying provisional; U.S. Provisional Application (Ser. No. 62/258,253), which teachings are also incorporated by reference specifically to using a scale to instruct a user to have a particular posture while obtaining scale-data features and aspects as described in connection with FIGS. 1a-1b in the underlying provisional; and U.S. Provisional Application (Ser. No. 62/266,523), which teachings are also incorporated by reference specifically concerning grouping users into inter and intra scale social groups based on aggregated user data sets, and providing normalized user data to other users in the social group aspects as exemplified by disclosure in connection with FIGS. 1a-1c of the underlying provisional. For instance, embodiments herein and/or in the PCT and/or provisional applications may be combined in varying degrees (including wholly). Reference may also be made to the experimental teachings and underlying references provided in the PCT and/or provisional applications. Embodiments discussed in the provisional applicants are not intended, in any way, to be limiting to the overall technical disclosure, or to any part of the claimed invention unless specifically noted.

Reference may also be made to published patent documents U.S. Patent Publication 2010/0094147 and U.S. Patent Publication 2013/0310700, which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

As illustrated herein, various circuit-based building blocks and/or modules may be implemented to carry out one or more of the operations/activities described herein shown in the block-diagram-type figures. In such contexts, these building blocks and/or modules represent circuits that carry out these or related operations/activities. For example, in certain embodiments discussed above (such as the pulse circuitry modularized as shown in FIGS. 3a-b), one or more blocks/modules are discrete logic circuits or programmable logic circuits for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible from a memory circuit. As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. An apparatus comprising:
a platform in which a plurality of electrodes are integrated and configured and arranged for engaging a user;
processing circuitry, including a CPU and a memory circuit with user-corresponding data stored in the memory circuit, configured and arranged under the platform upon which the user stands, the processing circuitry being electrically integrated with the plurality of electrodes and being configured to collect physiologic parameter data from the user while the user is standing on the platform using signals obtained by the plurality of electrodes and force sensor circuitry and to further:
  process the user-corresponding data with physiologic parameter data obtained while the user is standing on the platform and therefrom derive and output derivation data indicative of a physiologic status of the user for assessment of a condition or treatment of the user that corresponds with the physiologic status;
  send the output derivation data indicative of the physiologic status to external circuitry, that includes a computer processor, for assessment of a condition or treatment of the user that corresponds with the physiologic status;
  receive user-directed data indicative of a new dosage for a prescription drug prescribed for the user and associated with or in response to the output derivation data; and
  collect or track, via the platform, further physiologic parameter data obtained while the user is standing on the platform for assessing if the new dosage for a prescription drug controls symptoms or mitigates side effects associated with the condition or treatment.

2. The apparatus of claim 1, wherein the user-corresponding data includes statistical data based on demographics of a sample census pertinent to the user, and wherein the processing circuitry is configured and arranged to:
process the user-corresponding data and store, in response to the derived derivation data, additional data with a time stamp indicating a time at about when the physiological parameter data is obtained; and
repeat the acts of processing the user-corresponding data and storing, in response to the derived derivation data at another subsequent time, and therefrom generate a refined set of derived derivation data to supplement the user-corresponding data with information corresponding to the physiologic parameter data.

3. The apparatus of claim 1, wherein the output derivation data indicative of the physiologic status of the user for assessment of a condition or treatment includes physiological parameters related to a symptom being treated with the prescription drug or a side effect of the prescription drug.

4. The apparatus of claim 1, wherein the apparatus further includes the external circuitry, wherein the external circuitry is at a remote location and that is not integrated with the platform.

5. The apparatus of claim 4, wherein the external circuitry is configured and arranged to determine additional physiologic parameter data of the user using the derivation data.

6. The apparatus of claim 4, wherein the external circuitry is configured and arranged to correlate the user with a condition or treatment by comparing the physiologic parameter data of the user to reference information.

7. The apparatus of claim 6, wherein the reference information includes information selected from the group consisting of a lookup table, rules, an index, a graph, a plurality of operations, and a combination thereof.

8. The apparatus of claim 6, wherein the reference information includes a range of values for the physiological parameter data for other users having corresponding condition or treatment indicators and wherein the other users are of a demographic background of the user.

9. The apparatus of claim 8, wherein the external circuitry is configured to determine the reference information using received user-corresponding data that is indicative of the demographic background of the user.

10. The apparatus of claim 6, wherein the external circuitry is configured and arranged to correlate the user with the condition or treatment by using a pulse wave velocity (PWV) of the user as an indicator for arterial stiffness by referring to the reference information that reveals an appropriate range of arterial stiffness for other users having corresponding arterial-stiffness indicators.

11. The apparatus of claim 6, wherein the external circuitry is configured to correlate the user with the condition or treatment by using a PWV of the user as an indicator for fluid retention levels by referring to a reference table that reveals an appropriate range of fluid retention level for other users having corresponding fluid retention level indicators.

12. The apparatus of claim 4, wherein the external circuitry is configured to determine an adjusted dose for the prescription drug in response to the output derivation data.

13. The apparatus of claim 1, further including the external circuitry, wherein the external circuitry is: to be operated by or on behalf of a healthcare professional at a remote location which is remote from where the platform is located; coupled to the processing circuitry under the platform via a wireless connection; and wherein the user-directed data indicative of a new dosage for a prescription drug is to be derived in response to review of the output derivation data indicative of a physiologic status of the user and use of the external circuitry by or on behalf of the healthcare professional.

14. The apparatus of claim 1, wherein the user-directed data indicative of a new dosage is to be conveyed to the user via the processing circuitry under the platform.

15. The apparatus of claim 1, wherein the external circuitry that includes a computer processor: is configured external to the processing circuitry under the platform; and is communicatively integrated with the processing circuitry for processing the output derivation data and in response, using other data indicative of a physiologic status of the user to recommend the user-directed data indicative of a new dosage.

16. The apparatus of claim 1, wherein the external circuitry is to collect at least one of the following types of data from or associated with the user independent of the processing circuitry under the platform: glucose measurement data; blood pressure data; ECG data; cardio-related data other than ECG data; and body temperature data.

17. An apparatus comprising:
a scale including:
a platform in which a plurality of electrodes are integrated and configured and arranged for engaging a user;
processing circuitry, including a CPU and a memory circuit with user-corresponding data stored in the memory circuit, configured and arranged under the platform, the processing circuitry being electrically integrated with the plurality of electrodes and being configured to:
process the user-corresponding data with physiologic parameter data obtained while the user is standing on the platform and therefrom derive derivation data indicative of a physiologic status of the user for assessment of a condition or treatment of the user that corresponds with the physiologic status;
output, to external circuitry that includes a computer processor and that is at a remote location and not integrated with the scale, the derivation data for assessment of a condition or treatment of the user that corresponds with the physiologic status;
receive user-directed data indicative of a new dosage for a prescription drug prescribed for the user and associated with or in response to the output derivation data; and
collect or track, via the scale, further physiologic parameter data obtained while the user is standing on the platform, for assessing if the new dosage for the prescription drug controls symptoms or mitigates side effects associated with the condition or treatment; and
the external circuitry configured and arranged to perform prescription drug titration by:
comparing the derivation data, including the physiologic parameter data, to reference information which correlates to the user; and
determine an adjusted dose for the prescription drug in response to the comparison for providing data corresponding to the user-directed data indicative of the new dosage for use by the processing circuitry of the scale.

18. The apparatus of claim 17, wherein the reference information includes symptoms of a health condition being treated by the prescription drug and potential side effects of the prescription drug and wherein the external circuitry is configured and arranged to determine the adjusted dose in response to identifying at least one of: a symptom above a threshold and a side effect above a threshold.

19. The apparatus of claim 17, wherein the external circuitry is: to be operated by or on behalf of a healthcare professional at a remote location which is remote from where the scale is located; coupled to the processing circuitry under the platform via a wireless connection; and wherein the user-directed data indicative of a new dosage for a prescription drug is to be derived in response to review of the output derivation data indicative of a physiologic status of the user and use of the external circuitry by or on behalf of the healthcare professional.

20. The apparatus of claim 17, wherein the user-directed data indicative of a new dosage is to be conveyed to the user via the processing circuitry under the platform, and
wherein the external circuitry that includes a computer processor: is configured external to the processing circuitry under the platform; and is communicatively integrated with the processing circuitry for processing the output derivation data and in response, uses other data indicative of a physiologic status of the user to recommend the user-directed data indicative of a new dosage.

* * * * *